(12) United States Patent
Hopkins et al.

(10) Patent No.: US 11,477,970 B2
(45) Date of Patent: Oct. 25, 2022

(54) TRANSGENIC ANIMAL PHENOTYPING PLATFORM AND USES THEREOF

(71) Applicant: NemaMetrix Inc., Eugene, OR (US)

(72) Inventors: Christopher E. Hopkins, Murray, UT (US); Trisha J. Brock, Eugene, OR (US); Kathryn McCormick, Eugene, OR (US); Gongping He, Murray, UT (US)

(73) Assignee: NemaMetrix Inc., Eugene, OR (US)

( * ) Notice: Subject to any disclaimer, the term of this patent is extended or adjusted under 35 U.S.C. 154(b) by 505 days.

(21) Appl. No.: 16/281,988

(22) Filed: Feb. 21, 2019

(65) Prior Publication Data

US 2020/0060246 A1  Feb. 27, 2020

Related U.S. Application Data

(60) Provisional application No. 62/653,092, filed on Apr. 5, 2018, provisional application No. 62/633,590, filed on Feb. 21, 2018.

(51) Int. Cl.
| | |
|---|---|
| *A01K 67/033* | (2006.01) |
| *A61K 49/00* | (2006.01) |
| *C12N 15/85* | (2006.01) |
| *G01N 33/50* | (2006.01) |

(52) U.S. Cl.
CPC ...... *A01K 67/0336* (2013.01); *A61K 49/0008* (2013.01); *C12N 15/8509* (2013.01); *G01N 33/5085* (2013.01); *A01K 2207/15* (2013.01); *A01K 2217/077* (2013.01); *A01K 2227/703* (2013.01); *A01K 2267/0318* (2013.01); *A01K 2267/0393* (2013.01); *C12N 2015/859* (2013.01); *C12N 2015/8536* (2013.01); *G01N 2333/43534* (2013.01)

(58) Field of Classification Search
CPC .................................................. A01K 67/0336
See application file for complete search history.

(56) References Cited

U.S. PATENT DOCUMENTS

| | | | |
|---|---|---|---|
| 6,861,256 B2 | 3/2005 | Ruvkun et al. | |
| 8,937,213 B2 | 1/2015 | Hopkins et al. | |
| 2002/0178461 A1 | 11/2002 | Lin | |
| 2003/0134421 A1 | 7/2003 | Harrington et al. | |
| 2012/0192298 A1* | 7/2012 | Weinstein | C12N 15/8509 800/14 |
| 2013/0118411 A1 | 5/2013 | Lockery | |
| 2014/0237683 A1* | 8/2014 | Song | C12N 15/8216 800/278 |
| 2016/0050894 A1 | 2/2016 | Lauth et al. | |
| 2017/0169164 A1 | 6/2017 | Kokel et al. | |
| 2017/0311599 A1 | 11/2017 | Komuniecki et al. | |

FOREIGN PATENT DOCUMENTS

| | | |
|---|---|---|
| WO | 2017066497 A2 | 4/2017 |
| WO | WO-2017066497 A2 * | 4/2017 ............ C12N 15/11 |

OTHER PUBLICATIONS

Frokjaer-Jensen et al. (2016, Cell, vol. 166, pp. 343-357). (Year: 2016).*
International Search Report from related PCT patent Application No. PCT/US2019/019027 dated Jun. 7, 2019.
Frokjaer-Jensen et al., An abundant class of non-coding DNA can prevent stochastic gene silencing in the C. elegans germline., Cell, Jun. 30, 2016, vol. 166, No. 2, pp. 343-357.
Nyamsuren et al., A mutation in CHN-1/CHIP suppresses muscle degeneration in Caenorhabditis elegans, Developmental Biology, Dec. 1, 2007, vol. 312, Issue 1, pp. 193-202.
Giunti P et al, Molecular mechanism of Spinocerebellar Ataxia type 6: glutamine repeat disorder, channelopathy and transcriptional dysregulation, The multifaceted aspects of a single mutation, Front Cell Neurosci, Feb. 16, 2015;9:36.
Prontera P et al., Epilepsy in hemiplegic migraine: Genetic mutations and clinical implications, Cephalalgia, Jan. 1, 2017:333102416686347.
Brashear A et al, ATP1A3-Related Neurologic Disorders. GeneReviews—National Center for Biotechnology Information, Feb. 22, 2018.
Schirinzi T et al, Childhood Rapid-Onset Ataxia: Expanding the Phenotypic Spectrum of ATP1A3 Mutations, Cerebellum, Feb. 3, 2018.
Pavlidis E et al, Alternating hemiplegia of childhood and a pathogenic variant of ATP1A3: a case report and pathophysiological considerations, Epileptic Disord, Jun. 1, 2017;19(2):226-230.
Radman I, Greiss S, Chin JW, Efficient and rapid C. elegans transgenesis by bombardment and hygromycin B selection, PLoS One, Oct. 9, 2013;8(10):e76019.
Hu et al., An integrative approach to ortholog prediction for disease-focused and other functional studies, BMC Bioinformatics, Aug. 12, 2011;357.

(Continued)

*Primary Examiner* — Ram R Shukla
*Assistant Examiner* — David A Montanari
(74) *Attorney, Agent, or Firm* — Koren Anderson

(57) ABSTRACT

The present disclosure provides transgenic nematode systems for assessing function of heterologous genes, their variants and drug discovery. The transgenic nematodes contain a heterologous gene that is inserted via homologous recombination at the native locus replacing and removing the nematode ortholog, wherein expression of the heterologous gene rescues function of the removed nematode ortholog and a transgenic control animal is provided. The heterologous gene may be further modified to provide a variant, such as a human clinical variant, whereby a transgenic test animal is provided. Those transgenic test animals are used in methods to assess function of the heterologous variant and drug screens to find therapeutic candidates reversing deviant activity back to wildtype.

12 Claims, 14 Drawing Sheets

Specification includes a Sequence Listing.

(56) References Cited

OTHER PUBLICATIONS

Hutton M et al. Association of missense and 5'-splice-site mutations in tau with the inherited dementia FTDP-17. Nature. Jun. 18, 1998;393(6686):702-5.
Snowden J et al, Progranulin gene mutations associated with frontotemporal dementia and progressive non-fluent aphasia, Brain, Nov. 2006;129(Pt 11):3091-102.
Huey E et al, Characteristics of frontotemporal dementia patients with a Progranulin mutation, Ann Neurol, Sep. 2006;60(3):374-80.
Restif C et al, CeleST: computer vision software for quantitative analysis of C. elegans swim behavior reveals novel features of locomotion, PLoS Comput Biol, Jul. 17, 2014;10(7):e1003702.
Mitchell P et al, A differential role for neuropeptides in acute and chronic adaptive responses to alcohol: behavioral and genetic analysis in Caenorhabditis elegans, PLoS One, May 3, 2010;5(5):e10422.
Leung, C K, Deonarine, A., Strange, K. & Choe, K.P., High-throughput Screening and Biosensing with Fluorescent C. elegans Strains, J Vis Exp, 2011.
Project Demeter Proposal (Apr. 2017).
Jansen I et al, Establishing the role of rare coding variants in known Parkinson's disease risk loci, Neurobiol Aging, Nov. 2017, 59-220. e11-220 e18.
Hegde M et al, Development and Validation of Clinical Whole-Exome and Whole-Genome Sequencing for Detection of Germline Variants in Inherited Disease, Arch Pathol Lab Med. Jun. 2017;141(6):798-805.
Hu Y et al, An integrative approach to ortholog prediction for disease-focused and other functional studies, BMC Bioinformatics, Aug. 31, 2011;12:357.
Csobonyeiova M et al, Recent Advances in iPSC Technologies Involving Cardiovascular and Neurodegenerative Disease Modeling, General Physiology and Biophysics 35, No. 1, Jan. 2016, 1-12.
Breslin S and O'Driscoll L, Three-Dimensional Cell Culture: The Missing Link in Drug Discovery, Drug Discovery Today 18, No. 5-6, Mar. 2013, 240-49.
Leung C K et al, An ultra high-throughput, whole-animal screen for small molecule modulators of a specific genetic pathway in Caenorhabditis elegans, PLoS One, Apr. 29, 2013;8(4):e62166.
Artal-Sanz M et al., Caenorhabditis elegans: a versatile platform for drug discovery, Biotechnol J, Dec. 2006; 12(1):1405-18.
O'Reilly LP et al, C. elegans in high-throughput drug discovery, Adv Drug Deliv Rev, Apr. 2014, 247;69-70:247-53.
Xiong H et al, An enhanced C. elegans based platform for toxicity assessment. Sci Rep, Aug. 29, 2017, 7(1):9839.
Kim W et al, An update on the use of C. elegans for preclinical drug discovery: screening and identifying anti-infective drugs, Expert Opin Drug Discov, Jun. 2017, 12(6):625-633.
Kim H et al, A co-CRISPR strategy for efficient genome editing in Caenorhabditis elegans, Genetics, Aug. 2014, 197(4):1069-80.
Sugi T et al, Genome Editing in C. elegans and Other Nematode Species, Int J Mol Sci, Feb. 26, 2016,17(3):295.
Farboud B and Meyer BJ, Dramatic enhancement of genome editing by CRISPR/Cas9 through improved guide RNA design. Genetics, Apr. 2015, 199(4):959-71.
Paix A et al, High Efficiency, Homology-Directed Genome Editing in Caenorhabditis elegans Using CRISPR-Cas9 Ribonucleoprotein Complexes, Genetics, Sep. 2015, 201(1):47-54.
Redemann S et al., C. elegans codon Adapter—GGA, Nat Methods, Mar. 2011, 8(3):250-2.
Sorkac A et al., In Vivo Modelling of ATP1A3 G316S-Induced Ataxia in C. elegans Using CRISPR/Cas9-Mediated Homologous Recombination Reveals Dominant Loss of Function Defects, PLoS One, Dec. 9, 2016, 11-12.
Dickinson D and Goldstein B, CRISPR-Based Methods for Caenorhabditis elegans Genome Engineering. Genetics, Mar. 2016, 202(3):885-901.
Van Deerlin V et al., TARDBP mutations in amyotrophic lateral sclerosis with TDP-43 neuropathology: a genetic and histopathological analysis, Lancet Neurol, May 2008;7(5):409-16.
Gibson et al., Enzymatic assembly of DNA molecules up to several hundred kilobases, 2009 Nature Methods, May, 6(5):343-5.
Frokjaer-Jensen C et al, Single-copy insertion of transgenes in Caenorhabditis elegans, Nat Genet, Nov. 2008, 40(11):1375-83.
Agarwala et al., Nucleic Acids Res, Jan. 4, 2018, 46(D1):D8-D13.
Raizen D and Avery L, Electrical activity and behavior in the pharynx of Caenorhabditis elegans, Neuron, Mar. 1994, 12(3):483-95.
Brock T et al., Precision deletion of the entire coding sequence of the mod-5 locus causes increase in pharyngeal pumping frequency, Micropublication: biology, Jul. 6, 2017.
Russell J et al., Electrophysiological measures of aging pharynx function in C. elegans reveal enhanced organ functionality in older, long-lived mutants, J Gerontol A Biol Sci Med Sci, Nov. 18, 2017.
Weeks J et al., Microfluidic EPG Recordings Show Striking Pharyngeal Pumping Phenotype in a C. elegans Alzheimer's Disease Model, Micropublication: biology, 2006.
Liu J and Chin-Sang ID, C. elegans as a model to study PTEN's regulation and function, Methods, May 2015;77-78:180-90.
Bang J et al., Frontotemporal dementia, Lancet, Oct. 24, 2015, 386(10004):1672-82.
Ratnavalli E et al., The prevalence of frontotemporal dementia, Neurology, Jun. 2002, 58(11):1615-21.
Rainero I et al., Recent advances in the molecular genetics of frontotemporal lobar degeneration, Funct Neurol, Jan./Mar. 2017, 32(1):7-16.
Deleon J et al., Frontotemporal dementia, Handb Clin Neurol, 2018 148:409-430.
Kerchner G et al., Abhorring the vacuum: use of Alzheimer's disease medications in frontotemporal dementia. Expert Rev Neurother, May 2011, 11(5):709-17.
Mukerjee O et al., HDDD2 is a familial frontotemporal lobar degeneration with ubiquitin-positive, tau-negative inclusions caused by a missense mutation in the signal peptide of progranulin, Ann Neurol, Sep. 2006, 60(3):314-22.
Gass J et al., Mutations in progranulin are a major cause of ubiquitin-positive frontotemporal lobar degeneration, Hum Mol Genet, Oct. 15, 2006, 15(20):2988-3001.
Van Swieten J and Heutink P, Mutations in progranulin (GRN) within the spectrum of clinical and pathological phenotypes of frontotemporal dementia, Lancet Neurol, Oct. 2008, 7(10):965-74.
Dejesus-Hernandez M et al, Expanded GGGGCC hexanucleotide repeat in noncoding region of C9ORF72 causes chromosome 9p-linked FTD and ALS, Neuron, Oct. 20, 2011, 72(2):245-56.
Renton A et al, A hexanucleotide repeat expansion in C9ORF72 is the cause of chromosome 9p21-linked ALS-FTD, Neuron, Oct. 20, 2011, 72(2):257-68.
Chen-Plotkin A et al., TAR DNA-binding protein 43 in neurodegenerative disease, Nat Rev Neurol, Apr. 2010;6(4):211-20.
Rizzu P et al, High prevalence of mutations in the microtubule-associated protein tau in a population study of frontotemporal dementia in the Netherlands, Am J Hum Genet, Feb. 1999;64(2):414-21.
Caroppo P et al, Defining the spectrum of frontotemporal dementias associated with TARDBP mutations, Neurol Genet, May 26, 2016;2(3).
Borghero G et al, A patient carrying a homozygous p.A382T TARDBP missense mutation shows a syndrome including ALS, extrapyramidal symptoms, and FTD, Neurobiol Aging, Dec. 2011;32(12):2327.
Faber P, Alter J, Macdonald M, Hart A, Polyglutamine-mediated dysfunction and apoptotic death of a Caenorhabditis elegans sensory neuron, Proc Natl Acad Sci U S A, Jan. 5, 1999;96(1):179-84.
Lee A et al, A new Caenorhabditis elegans model of human huntingtin 513 aggregation and toxicity in body wall muscles, PLoS One, Mar. 10, 2017;12(3):e0173644.
Zeineddine R et al, Flow cytometric measurement of the cellular propagation of TDP-43 aggregation, Prion, May 4, 2017; 11(3):195-204.
Moreno, F et al. A novel mutation P112H in the TARDBP gene associated with frontotemporal lobar degeneration without motor neuron disease and abundant neuritic amyloid plaques, Acta Neuropathol Commun, Apr. 3, 2015,3:19.

(56) References Cited

OTHER PUBLICATIONS

Chou C et al. TDP-43 pathology disrupts nuclear pore complexes and nucleocytoplasmic transport in ALS/FTD, Nat Meurosci, Feb. 2018;21(2):228-239.

Zhu J et al, Serotonin Transporter Gene Polymorphisms and Selective Serotonin Reuptake Inhibitor Tolerability: Review of Pharmacogenetic Evidence, Pharmacotherapy, Jun. 27, 2017.

Sugawarah et al., Hypermethylation of serotonin transporter gene in bipolar disorder detected by epigenome analysis of discordant monozygotic twins, Transl Psychiatry, Jul. 26, 2011;1:e24.

Peitl V et al, Depressive symptoms in schizophrenia and dopamine and serotonin gene polymorphisms, Prog Neuropsychopharmacol Biol Psychiatry, Jul. 3, 2017;77:209-215.

* cited by examiner

SEQUENCE LISTING

```
<160> NUMBER OF SEQ ID NOS: 102

<210> SEQ ID NO 1
<211> LENGTH: 1926
<212> TYPE: DNA
<213> ORGANISM: Artificial Sequence
<220> FEATURE:
<223> OTHER INFORMATION: Synthetic oligonucleotide

<400> SEQUENCE: 1
atggctccta taggtttaaa agcagttgtt ggtgaaaaaa tcatgcacga cgtcatcaag      60
aaggtcaaga agaagggaga gtggaaggtc ctcgtcgtcg accaactctc catgcgtatg     120
ctctcctcct gctgcaagat gaccgacatc atgaccgagg gaatcaccat cgtcgaggac     180
atcaacaagc gtcgtgagcc actcccatcc ctcgaggccg tctacctcat cacccatcc     240 gagaagtccg tccactccct catctccgac ttcaaggacc caccaaccgc caagtaccgt     300 gccgccacg tcttcttcac cgactcctgc ccagacgccc tcttcaacga gctcgtcaag     360
tcccgtgccg ccaaggtcat caagaccctc accgagatca acatcgcctt cctcccatac     420
gagtcccaag tctactccct cgactccgcc gactccttcc aatccttcta ctccccacac     480
aaggtacttg agatccttaa acgcagtcga aaattggtaa ttttacaggc ccaaatgaag     540
aacccaatcc tcgagcgtct cgccgagcaa atcgccaccc tctgcgccac cctcaaggag     600
tacccagccg tccgttaccg tggagagtac aaggacaacg ccctcctcgc ccaactcatc     660
caagacaagc tcgacgccta caaggccgac gacccaacca tgggagaggg accagacaag     720
gcccgttccc aactcctcat cctcgaccgt ggattcgacc catcctcccc agtcctccac     780
gagctcacct tccaagccat gtcctacgac ctcctcccaa tcgagaacga cgtctacaag     840
```

```
tacgagacct  ccggaatcgg  agaggcccgt  gtcaaggagg  tcctcctcga  cgaggacgac       900
gacctctgga  tcgccctccg  tcacaagcac  atcgccgagg  tctcccaaga  ggtcacccgt       960
tccctcaagg  taagttcctc  cactagaaat  atcaggtgct  ataattgtgt  tcaggacttc      1020
tcctcctcca  agcgtatgaa  caccggagag  aagaccacca  tgcgtgacct  ctcccaaatg      1080
ctcaagaaga  tgccacaata  ccaaaaggag  ctctccaagt  actccaccca  cctccacctc      1140
gccgaggact  gcatgaagca  ctaccaagga  accgtcgaca  agctctgccg  tgtcgagcaa      1200
gacctcgcca  tgggaaccga  cgccgaggga  gagaagatca  aggacccaat  gcgtgccatc      1260
gtcccaatcc  tcctcgacgc  caacgtctcc  acctacgaca  agatccgtat  catcctcctc      1320
tacatcttcc  tcaagaacgg  aatcaccgag  gagaacctca  acaagctcat  ccaacacgcc      1380
caaatcccac  cagaggactc  cgagatcatc  accaacatgg  cccacctcgg  agtcccaatc      1440
gtcaccgact  ccaccctccg  tcgtcgttcc  aagccagagc  gtaaggtgag  tgattttaaa      1500
cattatctgt  acttaaatta  taaattctct  attcaggagc  gtatctccga  gcaaacctac      1560
caactctccc  gttggacccc  aatcatcaag  gacatcatgg  aggacaccat  cgaggacaag      1620
ctcgacacca  agcactaccc  atacatctcc  acccgttcct  ccgcctcctt  ctccaccacc      1680
gccgtctccg  cccgttacgg  acactggcac  aagaacaagg  ccccaggaga  gtaccgttcc      1740
ggaccacgtc  tcatcatctt  catcctcgga  ggagtctccc  tcaacgagat  gcgttgcgcc      1800
tacgaggtca  cccaagccaa  cggaaagtgg  gaggtcctca  tcggatccac  ccacatcctc      1860
accccacaaa  agctcctcga  caccctcaag  aagctcaaca  agaccgacga  ggagatctcc      1920
tcctaa                                                                     1926

<210> SEQ ID NO 2
<211> LENGTH: 45
<212> TYPE: DNA
<213> ORGANISM: Caenorhabditis elegans

<400> SEQUENCE: 2
gtacttgaga tccttaaacg cagtcgaaaa ttggtaattt tacag                 45

<210> SEQ ID NO 3
<211> LENGTH: 45
<212> TYPE: DNA
<213> ORGANISM: Caenorhabditis elegans

<400> SEQUENCE: 3
gtaagttcct ccactagaaa tatcaggtgc tataattgtg ttcag                 45

<210> SEQ ID NO 4
<211> LENGTH: 51
<212> TYPE: DNA
<213> ORGANISM: Caenorhabditis elegans

<400> SEQUENCE: 4
gtgagtgatt ttaaacatta tctgtactta aattataaat tctctattca g          51

<210> SEQ ID NO 5
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 5
```

```
gagctcggta cctcgcgaat gcatctagat gcatagtacg cagtacagtc cc          52
```

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 6

```
catcgatgca ctcacaatta acctgc                                       26
```

<210> SEQ ID NO 7
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 7

```
ggttgcaggt taattgtgag tgcatcgatg ggaagccccg ggagcacggg tgggatggct   60
cctataggtt taaaagcagt t                                            81
```

<210> SEQ ID NO 8
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 8

```
gaagttatgc ctgcagcgcg acatgtttaa tttattagga ggagatctcc tcgtcg      56
```

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9

```
taattgtgag tgcatcgacg                                              20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10

```
gcactctgtc atatgtcacg                                              20
```

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11

```
gaagctcaac aagaccgacg                                              20
```

<210> SEQ ID NO 12
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 12
actagacata tgacagagtg                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gctaccatag gcaccacgag                                                    20

<210> SEQ ID NO 14
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 14
gctcctcgac accctcaaga agctcaacaa gaccgatgaa gaaatttctt cttagcagag         60
tgcggggtac cgaaaagaat cgacaattga cgaa                                    94

<210> SEQ ID NO 15
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 15
cacttgaact tcaatacggc aagatgagaa tgactggaaa ccgtaccgca tgcggtgcct         60
atggtagcgg agcttcacat ggcttcagac caacagccta t                           101

<210> SEQ ID NO 16
<211> LENGTH: 113
<212> TYPE: DNA
<213> ORGANISM: Artificial Sequence
<220> FEATURE:
<223> OTHER INFORMATION: Synthetic oligonucleotide

<400> SEQUENCE: 16
tcctcgacgc caacgtctcc acctacgaca agatccacat tattcttctt tatattttc         60 ttaaaaatgg tattactgag gagaacctca acaagctcat ccaacacgcc caa              113

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
cctcaagaac ggaatcaccg                                                    20

<210> SEQ ID NO 18
<211> LENGTH: 74
<212> TYPE: DNA
```

```
<213> ORGANISM: Artificial Sequence
<220> FEATURE:
<223> OTHER INFORMATION: Synthetic oligonucleotide

<400> SEQUENCE: 18
ttgattgacc cagccgtgcg gtgtgaagac cgcctgcact tgattctgtt gtacattctt    60
tccaagaatg gaat                                                     74

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
acaacagaat caatctgagg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tgtacaacag aatcaatctg                                               20

<210> SEQ ID NO 21
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 21
tcctcgacga ggacgacgac ctctggatcg ccctccacca taaacatatt gctgaggtct   60
cccaagaggt cacccgttcc ctcaaggta                                     89

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ccgtcacaag cacatcgccg                                               20

<210> SEQ ID NO 23
<211> LENGTH: 95
<212> TYPE: DNA
<213> ORGANISM: Artificial Sequence
<220> FEATURE:
<223> OTHER INFORMATION: Synthetic oligonucleotide

<400> SEQUENCE: 23
ttctgctcga tgagaatgat gatttatggg ttgaaatgca ccataagcac atcgcagtgg   60
tttcacaaga agtcacaaag aacttgaaaa agttc                              95

<210> SEQ ID NO 24
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 24
atgatttatg ggttgaaatg                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tgtgacttct tgtgaaacaa                                               20

<210> SEQ ID NO 26
<211> LENGTH: 118
<212> TYPE: DNA
<213> ORGANISM: Artificial Sequence
<220> FEATURE:
<223> OTHER INFORMATION: Synthetic oligonucleotide

<400> SEQUENCE: 26
ccgtcgacaa gctctgccgt gtcgagcaag acctcgctat gggtactgat gctgaaggtg   60
aaaaaattaa agatccgatg taagccatcg tcccaatcct cctcgacgcc aacgtctc    118

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gccatgggaa ccgacgccga                                               20

<210> SEQ ID NO 28
<211> LENGTH: 117
<212> TYPE: DNA
<213> ORGANISM: Artificial Sequence
<220> FEATURE:
<223> OTHER INFORMATION: Synthetic oligonucleotide

<400> SEQUENCE: 28
aaggttgaac aagatttgag taccggaatc gacgccgagg gagagcgtgt ccgtgacgcc   60
atgtgactca tggtcccact cttgattgac ccagccgtgc ggtgtgaaga ccgcctc     117

<210> SEQ ID NO 29
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 29
aguaccggaa ucgacgcaga                                               20

<210> SEQ ID NO 30
<211> LENGTH: 20
<212> TYPE: RNA
<213> ORGANISM: Artificial Sequence
<220> FEATURE:
<223> OTHER INFORMATION: Synthetic oligonucleotide
```

<400> SEQUENCE: 30
acggcugggu caaucaaaag                                                  20

<210> SEQ ID NO 31
<211> LENGTH: 111
<212> TYPE: DNA
<213> ORGANISM: Artificial Sequence
<220> FEATURE:
<223> OTHER INFORMATION: Synthetic oligonucleotide

<400> SEQUENCE: 31
gcgcgtggaa tgttctcatc gttgacaccc tagccatgcg tatgctccca tcatgttgta    60
agatgcataa catcatggaa ggtaattaca cttgatattt ttaattcctt c             111

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tcgttgacac cctagccatg                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
aaaatgcaca atattatgga                                                  20

<210> SEQ ID NO 34
<211> LENGTH: 104
<212> TYPE: DNA
<213> ORGANISM: Artificial Sequence
<220> FEATURE:
<223> OTHER INFORMATION: Synthetic oligonucleotide

<400> SEQUENCE: 34
atagacgtgt caatttacag accggccgca agaaaacctg gactctcacc aagaaggagc    60
gtccacatga gcaagtttac caatcttccc gctgggttcc agtt                     104

<210> SEQ ID NO 35
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 35
agaccggccg caagaagacg                                                  20

<210> SEQ ID NO 36
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 36
gauugguaaa cuugcucgug                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gcagattaca caatgatggg                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tgcagaggat gctgcagccg                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gtgcttggca catctggagg                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
gtgcccggag ctacatccag                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gtcattgagt gatccgagcg                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ttatgattta ggatcgtgag                                               20

<210> SEQ ID NO 43
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 43
atacccgatt cgcaggacat                                         20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
aattaggcga ttaaaccagg                                         20

<210> SEQ ID NO 45
<211> LENGTH: 1713
<212> TYPE: DNA
<213> ORGANISM: Artifical Sequence
<220> FEATURE:
<223> OTHER INFORMATION: Synthetic oligonucleotide

<400> SEQUENCE: 45

```
atgtcctcct cctcctacgc caagaacgga accgccgacg gaccacactc cccaacctcc        60
caagtcgccc gtggaaccac cacccgtcgt tcccgtctca agcgttccga cggatccacc       120
acctccacct ccttcatcct ccgtcaagga tccgccgact cctacacctc ccgtccatcc       180
gactccgacg tctccctcga ggaggaccgt gaggccatcc gtcaagagcg tgagcaacaa       240
gccgccatcc aactcgagcg tgccaagtcc aagccagtcg ccttcgccgt caagaccaac       300
gtctcctact gcggagccct cgacgaggac gtcccagtcc atccaccgc catctccttc        360
gacgccaagg acttcctcca catcaaggtg agtgatttta acattatct gtacttaaat        420
tataaattct ctattcagga aaatacaac aacgactggt ggatcggacg tctcgtcaag        480
gagggatgcg agatcggatt catcccatcc ccactccgtc tcgagaacat ccgtatccaa       540
caagagcaaa agcgtggacg tttccacgga ggaaagtcct ccggaaactc ctcctcctcc       600
ctcggagaga tggtctccgg aaccttccgt gccaccccaa cctccaccgc caagcaaaag       660
caaaaggtca ccgagcacat cccaccatac gacgtcgtcc catccatgcg tccagtcgtc       720
ctcgtcggac catccctcaa gggatacgag gtcaccgaca tgatgcaaaa ggtaaataat       780
tatacattcg atgataaatt tatgcgtact atttttcagg ccctcttcga cttcctcaag       840
caccgtttcg acgacgtat ctccatcacc cgtgtcaccg ccgacatctc cctcgccaag        900
cgttccgtcc tcaacaaccc atccaagcgt gccatcatcg agcgttccaa cacccgttcc       960
tccctcgccg aggtccaatc cgagatcgag cgtatcttcg agctcgcccg ttccctccaa      1020
ctcgtcgtcc tcgacgccga caccatcaac cacccagccc aactcatcaa gacctccctc      1080
gccccaatca tcgtccatgt caaagtctcc tccccaaagg ttaaatgtac aaacaactat      1140
ttgaaagatt ttctcacccg attttttcag gtcctccaac gtctcatcaa gtcaagaggt      1200
aagtcccagt caaaacacct caacgtccag ctggtcgccg cagataaatt agcccaatgc      1260
ccaccagaga tgttcgacgt catcctcgac gagaaccaac tcgaggacgc ctgcgagcac      1320
ctcggagagt acctcgaggc ctactggcgt gccacccaca ccacctcctc caccccaatg      1380
accccactcc tcggacgtaa cctcggatcc accgccctct ccccatacccc aaccgccatc      1440
tccggactcc aatcccaacg tatgcgtcac tccaaccact ccaccgagaa ctccccaatc      1500
gagcgtcgtt ccctcatgac ctccgacgag aactaccaca acgagcgtgc ccgtaagtcc      1560
```
cgtaaccgtc tctcctcctc ctcccaacac tcccgtgacc actacccact cgtcgaggag      1620
gactacccag actcctacca agacacctac aagccacacc gtaaccgtgg atccccagga      1680
ggatactccc acgactcccg tcaccgtctc taa                                    1713

<210> SEQ ID NO 46
<211> LENGTH: 48
<212> TYPE: DNA
<213> ORGANISM: Caenorhabditis elegans

<400> SEQUENCE: 46
gtaaataatt atacattcga tgataaattt atgcgtacta ttttttcag                   48

<210> SEQ ID NO 47
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 47
gttaaatgta caaacaacta tttgaaagat tttctcaccc gatttttttca g               51

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ctgcggaaag ccatctagcg                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
atgtcacatc aatatgaaag                                                   20

<210> SEQ ID NO 50
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 50
ccagtcgcct tcgccgtcaa gaccaacgtc tcctatttcg gcgctcttga cgaggacgtc      60
ccagtcccat ccaccgccat ctcc                                              84

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
aagaccaacg tctcctactg                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
ctactgcgga gccctcgacg                                              20

<210> SEQ ID NO 53
<211> LENGTH: 119
<212> TYPE: DNA
<213> ORGANISM: Artificial Sequence
<220> FEATURE:
<223> OTHER INFORMATION: Synthetic oligonucleotide

<400> SEQUENCE: 53
cggagagatg gtctccggaa ccttccgtgc caccccgact tctactgcta aacagaagaa    60
aaagtaacgg agtacattcc tccttacgac gtcgtcccat ccatgcgtcc agtcgtcct   119

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
cttggcggtg gaggttgggg                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
gatgggacga cgtcgtatgg                                              20

<210> SEQ ID NO 56
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 56
agcaaaagca aaaggtcacc gagcacatcc caccatatga tgttgttcct tctgtccgcc    60
ctgttgttct tgttggacca tccctcaagg gatacgaggt caccgaca              108

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
ccttgaggga tggtccgacg                                              20

<210> SEQ ID NO 58
<211> LENGTH: 94

```
<212> TYPE: DNA
<213> ORGANISM: Artificial Sequence
<220> FEATURE:
<223> OTHER INFORMATION: Synthetic oligonucleotide

<400> SEQUENCE: 58
ccgtaagtcc cgtaaccgtc tctcctcctc ctcccagcat tctcgcgatc gtctagttga    60
ggaggactac ccagactcct accaagacac ctac                                94

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
gtggtcacgg gagtgttggg                                                20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
ccactaccca ctcgtcgagg                                                20

<210> SEQ ID NO 61
<211> LENGTH: 2769
<212> TYPE: DNA
<213> ORGANISM: Artificial Sequence
<220> FEATURE:
<223> OTHER INFORMATION: Synthetic oligonucleotide

<400> SEQUENCE: 61
atggtacaaa agtccagaaa tggtggagtt tacccgggtc catctggtga aaaaaaattg    60
aaagtaggat ttgtcggcct cgaccctgga gcgccggaca gtaccagaga tggcgcgctg   120
ttgatcgctg gttcggaggc accgaaacga ggaagtattc tcagtaagcc tcgtgcggga   180
ggtgccggcg ctggaaaacc gcctaaaaga atgccttttt acagaaagct gcagaacttc   240
ttgtataatg tgctggaacg accgagaggc tgggcattta tttatcacgc ctacgttttc   300
ttgcttgttt tctcctgcct tgtgttgagt gttttctcca ccataaaaga atacgaaaaa   360
agttccgagg gtgctcttta catcctcgaa attgtcacca tcgtggtgtt cggagtggaa   420
tactttgtta gaatttgggc cgctggctgc tgctgccgat accgaggctg gcgaggtcgt   480
ctgaaatttg ctcgaaaacc gttctgtgtc atcgacatta tggttctgat cgcaagtatt   540
gctgtcttgg cggcgggatc tcagggcaat gtgtttgcaa cctcggccct tagatccctc   600
cgatttttac aaatcctccg tatgatccgt atggaccgac gtggtggaac ttggaaactt   660
cttggatccg tcgtctacgc ccactccaag gtgagtgatt ttaaacatta tctgtactta   720
aattataaat tctctattca ggaactcgtc accgcctggt acatcggatt cttgtgtctt   780
atcctggcat cgtttcttgt ttacttggcc gaaaagggtg aaaacgatca ctttgacaca   840
tatgccgatg cgttgtggtg gggcttgatc actcttacga caattggata tggtgacaag   900
tatccgcaga catggaatgg tagacttctt gctgccacct tcaccctgat cggtgtcagt   960
ttcttcgccc tcccagctgg catcctgggc tcaggttttg cgctgaaggt ccaagagcag  1020
```

```
caccgacaaa aacactttga aaagcgacgt aaccctgccg ctggtttgat tcaatccgct    1080
tggagattct acgctacgaa cttgtctcgt accgatctgc actctacctg gcaatactac    1140
gaaagaacgg taacagtgcc gatgtattcg tcccaaactc aaacttacgg agcttcaaga    1200
ctgattccac cgctgaacca gctggagctg ttgcgaaacc ttaaatcaaa atctggcctg    1260
gctttccgaa aggatcctcc tccggagcct tcgccttcta agggaagtcc ttgcagaggc    1320
ccgctttgcg gttgctgccc aggacgttcc tcccaaaagg taataatta tacattcgat    1380 gataaattta tgcgtactat ttttcaggtc tccctcaagg accgtgtctt ctcctccccg    1440
agaggcgtag cagccaaggg aaagggaagt ccacaagcac aaactgttcg aagatcgcct    1500
tcagcggacc aatcattgga agactcgcca tcaaggtgc ctaaatcctg gtcctttggt    1560
gaccgttcga gagcaagaca ggccttccgt atcaagggtg cggcatctcg acagaattcg    1620
gaagaagctt cactcccagg cgaggacatc gtggacgaca atcttgtcc gtgtgaattt    1680 gtgaccgaag acctcactcc gggtttgaaa gtgtctatca gagcggtgtg cgtgatgaga    1740
ttcctcgtct ccaagcgtaa attcaaggaa tccttgcgac cgtatgacgt tatggacgtt    1800
atcgaacaat actcagctgg acatttggat atgctttcgc gtatcaagtc cctccaaagt    1860
agagtggacc aaaattgttgg cagaggacct gcaataccg acaaggacag aacgaagggt    1920
cctgcggaag ccgagctgcc tgaggaccca tcaatgatgg gtagattggg caaggttgaa    1980
aaacaagttt tgagtatgga gaaagaactg gactttcttg tcaatatcta tatgcaagaa    2040
atgggaatcc ctcctacgga gaccgaggcc tacttcggag ccaaggttaa atgtacaaac    2100
aactatttga agatttttct cacccgattt tttcaggagc ccgagccagc ccctccatac    2160
cactcaccag aagactcacg tgaacacgtt gacagacacg gttgcattgt gaaaattgtt    2220
cgttcttcgt cctcgacggg tcagaaaaac ttctcagcac cacctgctgc ccctcctgtc    2280
caatgccctc cgtcaactag ttggcaaccg caaagtcatc cgcgtcaggg ccatggtacg    2340
agtccagtag gcgatcacgg ctcgttggtg cgaatcccgc ctcctcctgc ccacgagaga    2400
tcattgtctg cctacggtgg cggcaatcga gcatctatgg agttcctgag acaagaagac    2460
accccaggat gcagaccgcc agagggtaac cttcgtgact ctgacacgtc catttcaatc    2520
ccttcagttg accacgaaga actcgagaga tccttcagtg gatttttccat ctctcaatct    2580 aaagaaaatc tggatgccct caactcatgt tatgcggcgg tcgcaccgtg tgcaaaggtt    2640
cgtccttaca tcgcggaggg agagagtgac acagacagtg acctgtgcac gccttgcgga    2700
ccgccgccac gatcagctac cggagaaggc cctttcggtg atgtgggatg ggcaggccct    2760
cgaaaataa                                                            2769
```

```
<210> SEQ ID NO 62
<211> LENGTH: 104
<212> TYPE: DNA
<213> ORGANISM: Artificial Sequence
<220> FEATURE:
<223> OTHER INFORMATION: Synthetic oligonucleotide

<400> SEQUENCE: 62
ggcgggatct cagggcaatg tgtttgcaac ctcggctctc caatctcttc gtttcctcca    60
gattcttcgt atgatccgta tggaccgacg tggtggaact tgga                     104

<210> SEQ ID NO 63
<211> LENGTH: 20
<212> TYPE: DNA
<213> ORGANISM: Artificial Sequence
```

<220> FEATURE:
<223> OTHER INFORMATION: Synthetic oligonucleotide

<400> SEQUENCE: 63
tcggagggat ctaagggccg                                                  20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
ggtccatacg gatcatacgg                                                  20

<210> SEQ ID NO 65
<211> LENGTH: 104
<212> TYPE: DNA
<213> ORGANISM: Artificial Sequence
<220> FEATURE:
<223> OTHER INFORMATION: Synthetic oligonucleotide

<400> SEQUENCE: 65
ggcgggatct cagggcaatg tgtttgcaac ctcggctctc cgttctcttt gcttcctcca     60
gattcttcgt atgatccgta tggaccgacg tggtggaact tgga                     104

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tcggagggat ctaagggccg                                                  20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
ggtccatacg gatcatacgg                                                  20

<210> SEQ ID NO 68
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 68
ttataaattc tctattcagg aactcgtcac cgcctggtat attggctttc tctgcgtcat     60
tctcgcatcg tttcttgttt acttggccga aaagggtgaa a                        101

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
caagaatccg atgtaccagg					20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
agtaaacaag aaacgatgcc					20

<210> SEQ ID NO 71
<211> LENGTH: 129
<212> TYPE: DNA
<213> ORGANISM: Artificial Sequence
<220> FEATURE:
<223> OTHER INFORMATION: Synthetic oligonucleotide

<400> SEQUENCE: 71
gggtgaaaac gatcactttg acacatatgc cgatgccctt tggtggggac ttatcatgct		60 cactactatc ggatacggag ataagtaccc acaaacatgg aatggtagac ttcttgctgc		120 caccttcac						129

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
agtctaccat tccatgtctg					20

<210> SEQ ID NO 73
<211> LENGTH: 20
<212> TYPE: DNA
<213> ORGANISM: Artificial Sequence
<220> FEATURE:
<223> OTHER INFORMATION: peptide

<400> SEQUENCE: 73
caagccccac cacaacgcat					20

<210> SEQ ID NO 74
<211> LENGTH: 102
<212> TYPE: DNA
<213> ORGANISM: Artificial Sequence
<220> FEATURE:
<223> OTHER INFORMATION: peptide

<400> SEQUENCE: 74
cttacgacaa ttggatatgg tgacaagtat ccgcagactt ggaactcccg tctcttggcc		60 gcgacattca ccctgatcgg tgtcagtttc ttcgccctcc ca				102

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
agtctaccat tccatgtctg                                                  20

<210> SEQ ID NO 76
<211> LENGTH: 20
<212> TYPE: DNA
<213> ORGANISM: Artificial Sequence
<220> FEATURE:
<223> OTHER INFORMATION: peptide

<400> SEQUENCE: 76
gacaccgatc agggtgaagg                                                  20

<210> SEQ ID NO 77
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 77
cttacgacaa ttggatatgg tgacaagtat ccgcagactt ggaacggccg tctcttggtc      60
gcgacattca ccctgatcgg tgtcagtttc ttcgccctcc ca                        102

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
agtctaccat tccatgtctg                                                  20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
gacaccgatc agggtgaagg                                                  20

<210> SEQ ID NO 80
<211> LENGTH: 106
<212> TYPE: DNA
<213> ORGANISM: Artificial Sequence
<220> FEATURE:
<223> OTHER INFORMATION: Synthetic oligonucleotide

<400> SEQUENCE: 80
acgtaaccct gccgctggtt tgattcaatc cgcttggcgt ttttatgcca ccaatgtctc      60
ccgcactgac ctgcactcta cctggcaata ctacgaaaga acggta                    106

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
cgtagcgtag aatctccaag                                                  20

```
<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
ttgccaggta gagtgcagat                                                     20

<210> SEQ ID NO 83
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 83
tgagacaaga agacacccca ggatgcagac cgccagaagg aactctccgt gactctgaca         60
cgtccatttc aatcccttca gttg                                                84

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tcacgaaggt taccctctgg                                                     20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
tggacgtgtc agagtcacga                                                     20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
agtctaccat tccatgtctg                                                     20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
gacaccgatc agggtgaagg                                                     20

<210> SEQ ID NO 88
<211> LENGTH: 101
<212> TYPE: DNA
<213> ORGANISM: Artificial Sequence
```

```
<220> FEATURE:
<223> OTHER INFORMATION: Synthetic oligonucleotide

<400> SEQUENCE: 88
ttacgacaat tggatatggt gacaagtatc cgcagacgtg aacggaagg ttgtttgggag      60 ctacgttcac cctgatcggt gtcagtttct tcgccctccc a                         101

<210> SEQ ID NO 89
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 89
ttacgacaat tggatatggt gacaagtatc cgcagacgtg aacggatca ttgttggcag      60 cgacgttcac cctgatcggt gtcagtttct tcgccctccc a                         101

<210> SEQ ID NO 90
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 90
ttacgacaat tggatatggt gacaagtatc cgcagacgtg aacgtgcgt ttgttggcag      60 cgacgttcac cctgatcggt gtcagtttct tcgccctccc a                         101

<210> SEQ ID NO 91
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 91
ttacgacaat tggatatggt gacaagtatc cgcagacgtg aacgaccgt ttgttggcag      60 cgacgttcac cctgatcggt gtcagtttct tcgccctccc a                         101

<210> SEQ ID NO 92
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 92
ttacgacaat tggatatggt gacaagtatc cgcagaactg aacggacgt ttgttggcag      60 cgacgttcac cctgatcggt gtcagtttct tcgccctccc a                         101

<210> SEQ ID NO 93
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 93
ttacgacaat tggatatggt gacaagtatc cgcagatctg aacggacgt ttgttggcag      60 cgacgttcac cctgatcggt gtcagtttct tcgccctccc a                         101
```

<210> SEQ ID NO 94
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 94
cttacgacaa ttggatatgg tgacaagtat ccgcagactt ggaactcccg tctcttggcc    60
gcgacattca ccctgatcgg tgtcagtttc ttcgccctcc ca    102

<210> SEQ ID NO 95
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 95
cttacgacaa ttggatatgg tgacaagtat ccgcagactt ggaacggccg tctcttggtc    60
gcgacattca ccctgatcgg tgtcagtttc ttcgccctcc ca    102

<210> SEQ ID NO 96
<211> LENGTH: 101
<212> TYPE: DNA
<213> ORGANISM: Artificial Sequence
<220> FEATURE:
<223> OTHER INFORMATION: Synthetic oligonucleotide

<400> SEQUENCE: 96
ttacgacaat tggatatggt gacaagtatc cgcagacttg gaacggccgt ccattggccg    60
cgacattcac cctgatcggt gtcagtttct tcgccctccc a    101

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
actagacata tgacagagtg    20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
caacaatgaa gatggactgg    20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
gattctactc cattgaacaa    20

```
<210> SEQ ID NO 100
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 100
aaaataagcg gccgccctc cccagaagtc ctccaacaat ggtcccggta cttcaagttg    60
ttaaaacata t                                                        71

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
tagtggacca gctcagcatg                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
gatatcagtc attttgcagc                                               20
```

TRANSGENIC ANIMAL PHENOTYPING PLATFORM AND USES THEREOF

CROSS-REFERENCE TO RELATED APPLICATIONS

This application claims the benefit of U.S. Provisional Patent Application Nos. 62/633,590, filed on 21 Feb. 2018, and 62/653,092 filed on 5 Apr. 2018, the contents of which are incorporated herein by reference in their entirety.

SEQUENCE LISTING

The instant application contains a Sequence Listing which has been submitted electronically in ASCII format via EFS-Web and hereby incorporated by reference in its entirety. Said ASCII copy, created on 8 Nov. 2019, is named NEMA006_SEQListing Corrected November 2019.TXT and is 31,354 bytes in size.

FIELD OF THE INVENTION

This application pertains generally to transgenic animals comprising a chimeric heterologous gene, such as human exon coding sequences and host animal intron sequences, replacing the animal ortholog and their use in assessing function of the expressed heterologous gene which can be used as system to assess pathogenicity in variants of the heterologous gene suspected to be cause or risk factor for disease and to discover therapeutic approaches leading to restoration of normal activity.

BACKGROUND OF THE INVENTION

Clinical genomics is revealing genetic variation occurs at high prevalence in the human population. Accumulated genomic data reveals each person has about 500 sequence variants that create mis sense or indel mutations in the coding regions of their genome (Jansen I et al. Establishing the role of rare coding variants in known Parkinson's disease risk loci. Neurobiol Aging. 2017 November; 59:220.e11-220.e18). With estimates as high as 30% of the genes in the human genome being involved in disease biology (Hegde M et al. Development and Validation of Clinical Whole-Exome and Whole-Genome Sequencing for Detection of Germline Variants in Inherited Disease. Arch Pathol Lab Med. 2017 June; 141(6):798-805.), any one individual harbors over 100 codon-changing variations in their important "disease" genes. Surprisingly, frameshifting indels with a high likelihood of pathogenicity account for only 7% of these variants. As a result, there remains a significant number of questionable alleles that are part of the background of anyone's personal genome. The challenge to the physician is to determine if a suspect allele is contributing to the disease as a pathogenic variant or if the clinical variant is not consequential and can be classified as a benign variant. For many of the genetic differences seen in a patient's genome, the benign or pathogenic status remains undefined and the variant is a Variant of Uncertain Significance (VUS). As a result, variant interpretation is the major bottleneck now that large scale sequencing is increasingly being used in clinical settings.

A significant proportion of clinical variants seen in patients with genetic disease are caused missense changes resulting in altered amino acid usage. Unlike the rarer frameshift and stop-codon mutations and some intra-/inter-genic variants, the functional consequence of missense amino acid changes can remain elusive. Change of function due to missense can result in partial loss of gene activities or gain-of-function changes that are highly pathogenic. There is an emergent need for the functional analysis of variant pathogenicity that occurs as a result of these amino acid changes.

A variety of technologies from bioinformatics to biochemical assays can be deployed to assess functional consequence of mis sense changes. Yet the most reliable are the in vivo systems. Most commonly used are cell culture assays to animal model studies. The lack of intact animal biology occurring cell culture systems renders this technique intractable to many transcellular pathogenicities. As a result, transgenic animal models are favored for capturing the nuances of intra- and inter-cellular pathogenicity in native contexts.

Transgenic mice are the traditional animal model for probing functional consequence of genomic variation. Yet their high expense and low throughput leave their use as intractable to address the 100,000,000's of coding altering variants predicted to occur in human populations. Many groups are now focusing on using alternative model organisms (Zebrafish, *Drosophila* and *C. elegans*) as a more affordable and timely approach to assessing variant specific effects on gene function, for example, the Undiagnosed Disease Network). Yet current design compositions and features of the transgenics used in these studies are not as efficient or appropriate as they could be for accurate assessment of variant function.

As one of the five classical model organisms for genetic studies (worm, fly, yeast, zebrafish and mice) the *C. elegans* nematode worm has a unique set of attributes that make it highly optimal for high-throughput clinical variant phenotyping. At the genetic level, the *C. elegans* nematode rivals the *Drosophila* fly for having orthologs to 80% of human disease genes, wherein 6460 genes detected in ClinVar Miner database as human disease genes were queried for homologs using the DIOPT database (Hu Y et al. An integrative approach to ortholog prediction for disease-focused and other functional studies. BMC Bioinformatics. 2011 Aug. 31; 12:357). Of the multicellular models, the *C. elegans* animal model has the fastest life cycle (3 days). It has optical transparency for easy tissue and organ system expression observation. Finally, in a unique advantage of interpretability, the *C. elegans* animals are easy to breed as self-fertilizing hermaphrodites, which allow rapid population expansion of nearly identical animals with very minimal polymorphism load in the genetic background. This allows transgenesis and subsequent population phenotyping to be performed in a matter of a few weeks instead of years.

Transgenic *C. elegans* are optimal for drug screening capacity. Of the five animal models, only yeast provides higher diversity screening per meter of bench space in comparison to *C. elegans*. Yet, yeast exist in a single cellular context and it becomes challenging to accurately model human biology where variant function (or disfunction) operates in a 3-dimensional tissue-based architecture. The advent of iPSC (Csobonyeiova, M et al. Recent Advances in iPSC Technologies Involving Cardiovascular and Neurodegenerative Disease Modeling. General Physiology and Biophysics 35, no. 1 (January 2016): 1-12) and organoid (Breslin S and O'Driscoll L. Three-Dimensional Cell Culture: The Missing Link in Drug Discovery. Drug Discovery Today 18, no. 5-6 (March 2013): 240-49) technologies bring more biological-context relevance, yet they remain undemonstrated for capacity to deploy in robust high-throughput formats. The *C. elegans* animal model, on the other hand, is robust and fast for high density screens of biological alterations. For instance, a recent screen for SKN-1 inhibitors as anthelmintic therapeutics found promising hits in few weeks screen of 340,000 compounds (Leung C K et al. An ultra high-throughput, whole-animal screen for small molecule modulators of a specific genetic pathway in *Caenorhabditis elegans*. PLoS One. 2013 Apr. 29; 8(4):e62166). Many other groups have used transgenic *C. elegans* for medium- to high-throughput drug discovery (Artal-Sanz M et al. *Caenorhabditis elegans*: a versatile platform for drug discovery. Biotechnol J. 2006 December; 1(12):1405-18; O'Reilly L P et al. *C. elegans* in high-throughput drug discovery. Adv Drug Deliv Rev. 2014 April; 69-70:247-53; Xiong H et al. An enhanced *C. elegans* based platform for toxicity assessment. Sci Rep. 2017 Aug. 29; 7(1):9839; Kim W et al. An update on the use of *C. elegans* for preclinical drug discovery: screening and identifying anti-infective drugs. Expert Opin Drug Discov. 2017 June; 12(6):625-633; and, Kim H et al. A co-CRISPR strategy for efficient genome editing in *Caenorhabditis elegans*. Genetics. 2014 August; 197(4): 1069-80).

*C. elegans* are a microscopic organism, with intact nervous system capable of learned behavior, where the animal can pack into 96 well, 384 well and even 1536 well assays (Leung, C. K., Deonarine, A., Strange, K. & Choe, K. P. High-throughput Screening and Biosensing with Fluorescent *C. elegans* Strains. *J Vis Exp* (2011. It has complex tissue structure (nervous system, muscles, germ line, intestine, mouth-like pharynx, periodic excretion through anal sphincter, macrophage-like celomocytes, and a tough skin-like hypodermis). As a result, the *C. elegans* nematode provides complex tissue biology in an intact, easy-to-culture animal model.

Zebrafish have developed into a popular animal model platform for drug discovery with a fast-growing conference support (Zebrafish Disease Modeling Society) now in its 12$^{th}$ year. Advantages of the use of zebrafish as animal model are its inclusion in the vertebrate phylum which results in a high degree of homologous gene structures and organ systems in relation to humans. Breeds of zebrafish are available with high transparency (e.g. CASPER) which enabled direct in vivo monitoring of gene activity and organ variability in live animals. Like the liquid format used in *C. elegans*, animal growth and handling of zebrafish is easily automated with a variety of fluidic systems.

Current variant modeling systems in zebrafish, *C. elegans*, and other animals are predominantly done as site directed mutagenesis to insert a variant at the native ortholog locus. Only a few groups have tried expression of human transgenes in these animal models to varying levels of success. A simple and robust approach to create ideal transgenic compositions is lacking. As a result, there remains a need for a ubiquitous transgenics platform that can be used to assess function of broad categories of clinical variants and screen for drug discovery in the treatment of pathogenic clinical variants. Herein we provide an animal model transgenic platform wherein the animal model configuration frequently has the animal's ortholog replaced by a chimeric heterologous transgene, such as human disease exon coding sequences paired with a host animal (e.g. nematode) intron sequences, that can be used to increase understanding of variants (clinical and biological) as well as classify the presence of pathogenicity in Variants of Unknown Significance which can be used to increase diagnostic yield of genome sequence analysis in patients. Furthermore, the resulting transgenic animal systems can be used to provide highly-personalized (variant-specific) discovery of therapeutic approaches.

SUMMARY OF THE INVENTION

Herein are provided transgenic animal (e.g. zebrafish or *C. elegans* nematode) systems comprising chimeric heterologous genes, modified chimeric heterologous genes (e.g. clinical variants), methods of generating the transgenic animal systems, methods for assessing function of the clinical variants and methods for screening therapeutic agents for treatment of a subject with a certain clinical variant.

In embodiments provided herein is a transgenic animal system for assessing function of a heterologous gene comprising a host animal comprising a chimeric heterologous gene comprising heterologous exon coding sequences interspersed with artificial host animal intron sequences optimized for expression in the host animal wherein the chimeric heterologous gene replaced an entire host animal gene ortholog at a native locus and expression of the heterologous gene at least partially restores function of the replaced host animal ortholog providing a validated transgenic animal, wherein the heterologous gene is a eukaryotic gene.

In embodiments, the animal is a vertebrate selected from an avian, a fish, a reptile, a mammal, or an amphibian. In other embodiments, the animal is an invertebrate selected from a Porifera, a Cnidaria, a Platyhelmintes, a Nematoda, an Annelida, a Mollusca, an Arthropoda, or an Echinodermata. In certain embodiments, the animal is a nematode (e.g. *C. elegans*), a fruit fly, a zebrafish or a frog (e.g., *Xenopus*). In further embodiments, the animal is a metazoan. In other embodiments, the animal is a primate, mammal, rodent or fly. In embodiments, the animal is a parasite species. In other embodiments, the animal is a Chordata, Actinopterygii or Nematoda. In specific embodiments, the animal is *Danio rerio* zebrafish or *C elegans* nematode.

Provided herein is a transgenic zebrafish system for assessing function of a heterologous gene, wherein the heterologous gene is wild type, or a variant thereof. In embodiments, the system comprises a host zebrafish comprising a chimeric heterologous gene comprising heterologous exon coding sequences interspersed with artificial host zebrafish intron sequences optimized for expression in the host zebrafish wherein the chimeric heterologous gene replaced an entire host zebrafish gene ortholog at a native locus and expression of the heterologous gene at least partially restores function of the replaced zebrafish ortholog providing a validated transgenic zebrafish, and wherein the heterologous gene is a eukaryotic gene.

In embodiments, the system comprises a test transgenic zebrafish comprising a chimeric variant heterologous gene, comprising human exon coding sequences interspersed with artificial host zebrafish intron sequences optimized for expression in the host zebrafish, wherein the exon coding sequences comprise one or more mutations resulting in an amino acid change as compared to a wildtype reference sequence, wherein the chimeric variant heterologous gene replaced a host zebrafish gene ortholog at a native locus.

Also provided herein is a method of preparing a transgenic zebrafish comprising a chimeric heterologous gene. In embodiments, the methods comprise optimizing a heterologous gene coding sequence for expression in a host zebrafish comprising selecting host optimized codons, adding artificial host zebrafish intron sequences between exon coding sequences of the heterologous gene, and removing aberrant splice donor and/or acceptor sites to provide a chimeric heterologous gene sequence and inserting the chimeric heterologous gene sequence via homologous recombination into a native locus of the host zebrafish wherein the chimeric heterologous gene replaces an entire zebrafish ortholog gene at the native locus, and wherein expression of the heterologous gene at least partially restores function of the replaced zebrafish ortholog, wherein the heterologous gene is a eukaryotic gene.

In embodiments, the exon coding sequences of the heterologous gene may be wild type, or a variant thereof.

In embodiments provided herein is a transgenic nematode system for assessing function of a heterologous gene. In embodiments the system comprises a chimeric heterologous gene comprising heterologous exon coding sequences interspersed with artificial host nematode intron sequences optimized for expression in the host nematode wherein the chimeric heterologous gene replaced an entire host nematode gene ortholog at a native locus and expression of the heterologous gene at least partially restores function of the replaced nematode ortholog providing a validated transgenic nematode, and wherein the heterologous gene is a eukaryotic gene. In embodiments, the heterologous gene replaces the animal ortholog using gene swap techniques involving removing the native coding sequence of the host animal ortholog and replacing with modified cDNA coding sequence from a heterologous gene.

The choice of introduced transgene sequence can vary widely but in one embodiment the sequence is a modified cDNA coding sequence from any eukaryotic organism. In embodiments, Applicants found that using modified intron sequences from a highly expressed gene of the host animal, paired with or interspersed with the heterologous exon coding sequences—a chimeric heterologous gene—improved expression of the heterologous gene in the host animal.

In embodiments provided herein is a transgenic nematode comprising and expressing a heterologous gene wherein the host nematode comprises a chimeric heterologous gene comprising heterologous exon coding sequences interspersed with artificial host nematode intron sequences optimized for expression in the host nematode selected from SEQ ID NO: 2, SEQ ID NO: 3, SEQ ID NO: 4, SEQ ID NO: 46 or SEQ ID NO: 47, with the proviso the heterologous exon coding sequences are not from reporter protein coding sequences or fluorescent protein coding sequences. See FIG. 1.

In embodiments, the heterologous exon coding sequences are from a human gene. In certain embodiments, the human genes are selected from those listed in Table 1, Table 4 or Table 5. In embodiments, the chimeric heterologous gene is integrated in the nematode genome. In certain embodiments, the chimeric heterologous gene is inserted into a native locus of the host nematode. In alternative embodiments, the chimeric heterologous gene is inserted into a non-native locus of the host nematode or is inserted into a random site of the host nematode genome, or the chimeric heterologous gene is present in an expression vector wherein the heterologous gene is not integrated into the host nematode genome.

In embodiments, provided herein is transgenic nematode system for assessing function of a heterologous gene, wherein the host nematode comprises a chimeric heterologous gene comprising heterologous exon coding sequences interspersed with artificial host nematode intron sequences optimized for expression in the host nematode wherein the chimeric heterologous gene replaced an entire host nematode gene ortholog at a native locus and expression of the heterologous gene at least partially restores function of the replaced nematode ortholog providing a validated transgenic nematode, wherein the heterologous exon coding sequences are selected from human genes of Table 1, Table 4, or Table 5.

In embodiments, the heterologous gene is a human gene, and in certain embodiments, the heterologous gene is a human disease gene.

In other embodiments, a host nematode comprises a chimeric heterologous gene comprising heterologous exon coding sequences interspersed with artificial host nematode intron sequences optimized for expression in the host nematode wherein the chimeric heterologous gene replaced an entire host nematode gene ortholog at a native locus and expression of the heterologous gene at least partially restores function of the replaced nematode ortholog providing a validated transgenic nematode, wherein the chimeric heterologous gene sequence is selected from SEQ ID NO: 1, SEQ ID NO: 45, or SEQ ID NO: 61.

In certain other embodiments, the heterologous gene is from a parasitic nematode. In embodiments, the parasitic nematode is selected from *Trichuris muris, Ascaris lumbricoides, Ancylostoma duodenale, Necator americanus, Trichuris trichiura, Enterobius vermicularis, Strongyloides stercoralis, Trichinella spiralis, Wuchereria bancrofti, Brugia malayi, Brugia timori, Loa loa, Mansonella streptocerca, Onchocerca volvulus, Mansonella perstans, Mansonella ozzardi, Cooperia punctata, Cooperia oncophora, Ostertagia ostertagi, Haemonchus contortus, Ascaris suum, Aphelenchoides, Ditylenchus, Globodera, Heterodera, Longidorus, Meloidogyne, Nacobbus, Pratylenchus, Trichodorus, Xiphinema, Bursaphelenchus, Dirofilaria immitis, Toxocara canis, Toxocara cati, Ancylostoma braziliense, Ancylostoma tubaeforme, Ancylostoma caninum, Dirofilaria repens*, and *Uncinaria stenocephala*.

In embodiments, the heterologous gene is present as a single copy providing a heterozygote transgenic nematode. In certain embodiments, the heterozygote is maintained by labeling each chromosome with a marker.

In certain embodiments, the heterologous exon coding sequences are wildtype reference sequences providing a transgenic control nematode. In certain other embodiments, the heterologous gene is a variant of the wild type reference sequence wherein the variant heterologous gene comprises one or more mutations in the heterologous exon coding sequences as compared to a wildtype reference sequence resulting in at least one amino acid change providing a test transgenic animal. In embodiments, the mutation corresponds to a human disease gene clinical variant. In other embodiments, the heterologous gene is a variant of the wild type reference sequence wherein the variant heterologous gene comprises two or more mutations in the heterologous exon coding sequences as compared to a wildtype reference sequence resulting in at least two amino acid changes providing a test transgenic animal. In embodiments, the mutations correspond to one or more human disease gene clinical variants.

In other embodiments, the heterologous gene is followed by a host 3'UTR. In certain embodiments, the host 3'UTR is non-native.

The degree of homology (e.g., sequence similarity or identity) is important for creating systems where one can rely on the gene function being highly conserved between the host animal and the source of the transgene. In one embodiment, the cDNA of the heterologous gene is chosen to have between 100 to 60% sequence similarity to a host animal ortholog. In other certain embodiments, the cDNA of the heterologous gene is chosen to have between 59 to 40% sequence similarity to a host animal ortholog. In other certain embodiments, the cDNA of the heterologous gene is chosen to have between 39 to 20% sequence similarity to a host animal ortholog.

Occasionally the gene of interest is not conserved. An alternative embodiment is to choose the transgene sequence to be a non-conserved sequence. For instance, cDNA sequence not conserved in the host animal is inserted and driven by a promoter for selective tissue expression (global, specific, and or temporal). In some instances, genomic integration is not favorable. In one embodiment, the heterologous gene is not encoded by the genome but instead is epigenetic (extrachromosomal arrays or mRNA).

In addition to introduction of artificial host intron sequences into the cDNA sequence from the heterologous gene, the chimeric heterologous gene may be optimized for expression in the host animal wherein the heterologous gene is codon optimized for the host animal (e.g. nematode) and aberrant splice donor and/or acceptor sites removed.

In embodiments, the transgenic animal system further comprises an inducible promoter operably linked to a reporter gene wherein the promoter is from a gene expressed in response to expression of the heterologous gene. In other embodiments, the transgenic animal system further comprises an inducible promoter operably linked to a reporter gene wherein the promoter is from a gene inhibited in response to expression of the heterologous gene.

In embodiments provided herein is a method for preparing a transgenic nematode system comprising optimizing a heterologous gene coding sequence for expression in a host nematode comprising selecting host optimized codons, adding artificial host nematode intron sequences between exon coding sequences of the heterologous gene, and removing aberrant splice donor and/or acceptor sites to provide a chimeric heterologous gene sequence and, inserting the chimeric heterologous gene sequence via homologous recombination into a native locus of the host nematode wherein the chimeric heterologous gene replaces an entire nematode ortholog gene at the native locus, and wherein expression of the heterologous gene at least partially restores function of the replaced nematode ortholog, wherein the heterologous gene is a eukaryotic gene. See Example 1.

In alternative embodiments, the optimized heterologous gene is inserted using anyone of the following methods, inserting the optimized heterologous gene into a non-native locus of the nematode, or inserting the optimized heterologous gene into a random site of the nematode genome, or adding the optimized heterologous gene as an expression vector wherein the optimized heterologous gene is not integrated into the nematode genome.

In embodiments, the at least partially restored function can be measured or observed in phenotypic assay wherein a phenotype profile of the transgenic nematode is generated. See Example 3. Rescue, or at least partial restoration, of function validates the transgenic animals (e.g. nematode or zebrafish) for use as a platform for assessing function of clinical variants and drug discovery.

In embodiments provided herein are test transgenic nematodes (which can be used for assessing function of clinical variants and drug discovery) wherein the heterologous gene has been modified to correspond to a clinical variant. Those heterologous genes, present in the validated transgenic nematode, may be modified via amino acid substitution (wherein only those amino acids that are different in the clinical variant as compared to the heterologous gene are changed) or via gene swap (similar as performed for preparing the validated transgenic nematode), wherein the entire cDNA of the clinical variant is inserted in place of the heterologous gene. See Example 2. In embodiments, the clinical variant is classified as variants of uncertain significance (VUS), unassigned, pathogenic, likely pathogenic, likely benign, or benign.

In embodiments, the mutations are created from a pool of DNA repair templates each containing one or more mutations. In other embodiments, the mutations are created from a pool of DNA repair templates each containing two or more mutations In embodiments provided herein is a transgenic animal system for assessing function of an expressed variant heterologous gene, comprising a test transgenic animal (e.g. nematode or zebrafish) comprising a chimeric variant heterologous gene, comprising heterologous exon coding sequences interspersed with artificial host animal intron sequences optimized for expression in the host animal, wherein the exon coding sequences comprise one or more mutations resulting in an amino acid change as compared to a wildtype reference sequence, and wherein the chimeric variant heterologous gene replaced an entire host animal gene ortholog at a native locus, and wherein the heterologous gene is a eukaryotic gene.

Provided herein is a humanized transgenic nematode system for assessing function of an expressed human variant protein, comprising a test transgenic nematode comprising a chimeric variant heterologous gene, comprising human exon coding sequences interspersed with artificial host nematode intron sequences optimized for expression in the host nematode, wherein the exon coding sequences comprise one or more mutations resulting in an amino acid change as compared to a wildtype reference sequence, wherein the chimeric variant heterologous gene replaced a host nematode gene ortholog at a native locus.

In embodiments, the test transgenic animals (e.g., nematode or zebrafish) are used to assess function of the clinical variants and as a screen for therapeutic agents to identify drugs that may be used to treat individuals with those clinical variants. In certain embodiments, the method comprises culturing a test transgenic animal (e.g., animals comprising clinical variant of the heterologous gene), wherein the variant heterologous gene is a human clinical variant; and, performing a phenotypic screen to identify a phenotype of the test transgenic animal, wherein a change in phenotype as compared to a control transgenic animal (validated transgenic animal) comprising a wildtype heterologous gene indicates an altered function of the clinical variant in the test transgenic animal.

In embodiments, the phenotypic screen is selected a measurement of electrophysiology of pharynx pumping, a food race, lifespan extension and contraction assay, movement assay, fecundity assay with egg lay or population expansion, apoptotic body formation, chemotaxis, lipid metabolism assay, body morphology changes, fluorescence changes, drug sensitivity and resistance assays, oxidative stress assay, endoplasmic reticulum stress assay, nuclear stress assay, response to vibration, response to electric shock, or a combination thereof. In certain embodiments, the identified phenotype is selected from electropharyngeogram variant, feeding behavior variant, defecation behavior variant, lifespan variant, electrotaxis variant, chemotaxis variant, thermotaxis variant, mechanosensation variant, movement variant, locomotion variant, pigmentation variant, embryonic development variant, organ system morphology variant, metabolism variant, fertility variant, dauer formation variant, stress response variant, or a combination thereof.

In embodiments, the phenotypic assay is a food race wherein decreased time to reach food, as compared to the control transgenic nematode, indicates pathogenicity of the human clinical variant. In other embodiments, the phenotypic assay is a quantitative reduction of timeseries electrophysiological measurement of pharyngeal pumping. In certain aspects, the quantitative reduction is selected from the mean, median, standard deviation, SEM, coefficient of variation, or cumulative distribution of duration measures between successive excitation or relaxation peaks in the timeseries electrophysiological measurement or the mean, median, standard deviation, SEM of amplitude measures of excitation and relaxation peaks in the timeseries electrophysiological measurement, or the average waveform defined by an interval comprising a consecutive excitation and relaxation pair.

In certain embodiments, the test transgenic animal further comprise an inducible reporter gene operably linked to an inducible promoter. That promoter may be from a gene that is induced by the heterologous gene or variant heterologous gene (assess function of the expresses heterologous gene or variant heterologous gene) or the promoter may be from a gene that is inhibited by the heterologous gene or variant heterologous gene (drug screening). In certain embodiments are methods for assessing function of a human clinical variant, comprising: culturing a test transgenic animal (comprising a clinical variant of the heterologous gene from the validated transgenic animal), wherein the variant heterologous gene is a human clinical variant and wherein the transgenic animal further comprises an inducible promoter operably linked to a reporter gene, wherein the promoter is from a gene induced by expression of the human clinical variant gene; and, observing the inducible report gene expression, whereby human clinical variant genes with altered function are identified as pathogenic or likely pathogenic when the inducible reporter gene is expressed.

In certain other embodiments are methods for screening therapeutic agents to treat altered function of a human clinical variant, comprising placing a test transgenic animal (comprising a clinical variant of the heterologous gene from the validated transgenic animal) in a medium comprising a test compound, wherein the variant heterologous gene is a human clinical variant identified as pathogenic, likely pathogenic, unknown significance or unassigned; incubating the test transgenic animal with the test compound for a period from 2 minutes to seven days; and, performing a screening assay, whereby therapeutic agents are identified from the test compounds when the outcome of the screening assay is deemed positive. In embodiments, the screening assay is a phenotypic screen selected from a measurement of electrophysiology of pharynx pumping, a food race, lifespan extension and contraction assay, movement assay, fecundity assay with egg lay or population expansion, apoptotic body formation, chemotaxis, lipid metabolism assay, body morphology changes, fluorescence changes, drug sensitivity and resistance assays, or a combination thereof. In other embodiments, the test transgenic animal further comprises an inducible promoter operably linked to a reporter gene wherein the promoter is from a gene inhibited in response to expression of the human clinical variant, whereby therapeutic agents are identified when the inducible reporter gene is expressed.

In embodiments, methods comprise placing a present test transgenic nematode, with an identified behavioral or molecular phenotype that is different from an identified phenotype of a control transgenic nematode expressing a wildtype heterologous gene, in a medium comprising a test compound, wherein the variant heterologous gene is a human clinical variant; incubating the test transgenic nematode with the test compound for a period from 2 minutes to seven days; and, performing a phenotypic assay to identify a post-test compound behavioral or molecular phenotype of the test transgenic nematode, whereby therapeutic agents are identified from the test compounds when the post-test compound phenotype is more similar, as compared to the phenotype of the test transgenic nematode, to the phenotype of the control transgenic nematode In certain embodiments, a method for assessing function of a human clinical variant comprises culturing a present test transgenic nematode, wherein the variant heterologous gene is a human clinical variant and wherein the transgenic nematode further comprises an inducible promoter operably linked to a reporter gene, wherein the promoter is from a gene induced by expression of the human clinical variant gene; and, observing the inducible report gene expression, whereby human clinical variant genes with altered function are identified as pathogenic or likely pathogenic when the inducible reporter gene is expressed

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments disclosed herein.

DETAILED DESCRIPTION OF THE INVENTION

Introduction

Figure 1:
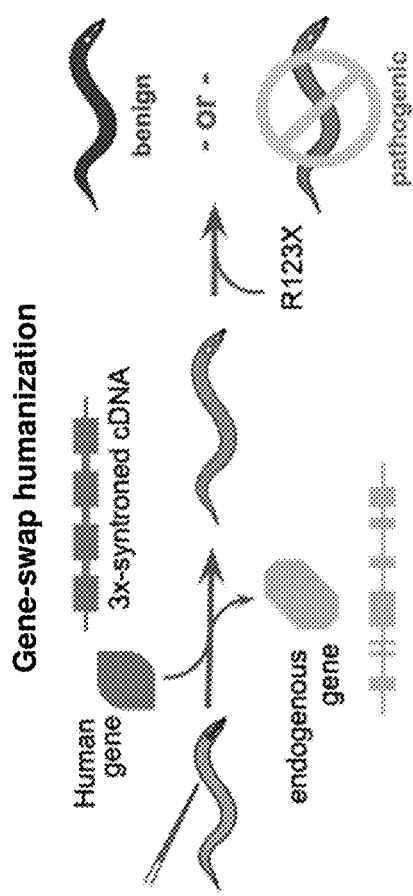
FIG. 1 illustrates a schematic of a gene-swap of a heterogenous gene into a native locus of a host animal replacing the animal ortholog (e.g. *C. elegans* nematode), wherein human exon coding sequences are paired with modified host intron sequences, followed by introduction of a clinical variant via a change in amino acid expression.

Provided herein is a validated transgenic animal system wherein an entire host animal ortholog is replaced with a chimeric heterologous gene, wherein the heterologous gene rescues (or at least partially restores) function of the removed animal ortholog. As used herein, this method of replacing the host animal ortholog with the chimeric heterologous gene, may also be referenced as "gene-swap". As used herein, "chimeric heterologous gene" refers to a sequence comprising heterologous (to the host animal) exon coding sequences interspersed, or paired, with artificial (or modified) host animal intron sequences, wherein the chimeric heterologous gene is optimized for expression in the host animal which may include codon optimization and removal of any aberrant splice donor and/or acceptor sites that were introduced as a function of the chimeric sequences. In embodiments, the heterologous exon coding sequences are "wild type" or from an allele that is reflective of a heterogenous population. In certain embodiments, the heterologous exon coding sequences are from human genes. A "validated" transgenic animal system are those animals that have a phenotypic profile that is deemed to have demonstrated rescue or partial restoration of function of the swapped gene, as compared to a control host animal (e.g., wild type (N2) animal that is genetically identical to the host animal prior to the introduction of the chimeric heterologous gene).

In embodiments, the validated transgenic animal system may be used for assessing function of the expressed heterologous gene.

Provided further is a transgenic animal system for assessing function of a variant heterologous gene, wherein clinical variants, expressed heterologous genes comprising one or more amino acid changes as compared to the wild type heterologous gene, are installed in the heterologous gene via site directed mutagenesis. Clinical variants are typically classified as pathogenic, likely pathogenic, benign, likely benign or a variant of unknown significance (VUS). The system provides a platform that can be used to test the function of those heterologous genes (e.g. human genes), variants of those heterologous genes (e.g. human clinical variants), or as a drug screening platform identifying therapeutic agents or drugs that alter the function of the expressed heterologous genes or for treatment of animals, including humans (e.g. drug candidates specific to the clinical variants of the heterologous genes).

The animals of the invention are "genetically modified" or "transgenic," which means that they have a transgene, or other foreign DNA, added or incorporated, or an endogenous gene modified, including, targeted, recombined, interrupted, deleted, disrupted, replaced, suppressed, enhanced, or otherwise altered, to mediate a genotypic or phenotypic effect in at least one cell of the animal and typically into at least one germ line cell of the animal. In some embodiments, the animal may have the transgene integrated on one allele of its genome (heterozygous transgenic). In other embodiments, animal may have the transgene on two alleles (homozygous transgenic).

In certain embodiments, the transgenic animals are model organisms including, but not limited to, nematodes, zebrafish, fruit fly, *Xenopus*, or rodents, such as mice and rats.

In certain embodiments, the present transgenic animals provide a single gene copy wherein a chimeric optimized cDNA of a heterologous gene, e.g. modified human cDNA, is inserted to replace coding sequences of a *C. elegans* ortholog. The humanized animal is then compared to an animal lacking that *C. elegans* gene, to confirm significant restoration of wild type function. The validated transgenic animal is then modified by installation of a clinical variant and tested in one or more phenotyping assays to detect aberrant function. These transgenic animal models have distinct advantages for testing and exploring variant biology. For example, humanized models circumvent differences in compound binding between humans and other species. And, our preliminary results show that gene-swapped loci may be more sensitive to pathogenic variant activity, as compared to pathogenic variant installation in the *C. elegans* gene. See Examples 1-15.

In embodiments, the chimeric heterologous gene comprises human heterologous exon coding sequences interspersed, or paired, with artificial host nematode intron sequences optimized for expression in the host nematode. In embodiments, the host nematode intron coding sequences are from a highly expressed *C. elegans* gene and may be further modified for optimized expression. Provided herein are transgenic nematodes comprising and expressing a heterologous gene, wherein the host nematode comprises a chimeric heterologous gene comprising heterologous exon coding sequences interspersed with artificial host nematode intron sequences optimized for expression in the host nematode and selected from SEQ ID NO: 2, 3 or 4. In embodiments, the heterologous exon coding sequences are human selected from the human genes of Table 1, Table 4 or Table 5. In other embodiments, the transgenic nematodes comprise a chimeric heterologous gene selected from SEQ ID NO: 1, SEQ ID NO: 44 or SEQ ID NO: 58.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"cDNA" as used herein means the deoxyribonucleic acid sequence that is derived as a copy of a mature messenger RNA sequence and represents the entire coding sequence needed for creation of a fully functional protein sequence.

As used herein, the terms "disrupt," "disrupted," and/or "disrupting" in reference to a gene mean that the gene is degraded sufficiently such that it is no longer functional. In embodiments, the native ortholog gene is replaced with the chimeric heterologous gene effectively disrupting the native host gene.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

As used herein, the term "donor homology" refers to a sequence at a target edit site that is also include in the nucleic acid sequence of a plasmid DNA construct that is necessary to instruct endogenous homologous repair machinery of the cell to create in frame insertion of a transgene sequence. Typically, a plasmid for instructing transgenesis contains a both a left-side and right-side donor homology sequence As used herein, the term "gene editing" refers a type of genetic engineering in which DNA is inserted, replaced, or removed from a genome using gene editing tools. Examples of gene editing tools include, without limitation, zinc finger nucleases, TALEN and CRISPR.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but is not limited to epilepsy, DMD, hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease. "Clinical variants" are used herein, are those genes that lead to a genetic disease wherein expression of the gene results in one or more amino acid changes as compared to wild type allele that does not lead to disease.

A "heterologous gene" as used herein refers to a nucleotide sequence not naturally associated with a host animal into which it is introduced, including for example, exon coding sequences from a human gene introduced, as a chimeric heterologous gene, into a host nematode.

The term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations).

As used herein, the term "homology driven recombination" or "homology direct repair" or "HDR" is used to refer to a homologous recombination event that is initiated by the presence of double strand breaks (DSBs) in DNA (Liang et al. 1998); and the specificity of HDR can be controlled when combined with any genome editing technique known to create highly efficient and targeted double strand breaks and allows for precise editing of the genome of the targeted cell; e.g. the CRISPR/Cas9 system (Findlay et al. 2014; Mali et al. February 2014; and Ran et al. 2013).

As used herein, the term "enhanced homology driven insertion or knock-in" is described as the insertion of a DNA construct, more specifically a large DNA fragment or construct flanked with homology arms or segments of DNA homologous to the double strand breaks, utilizing homology driven recombination combined with any genome editing technique known to create highly efficient and targeted double strand breaks and allows for precise editing of the genome of the targeted cell; e.g. the CRISPR/Cas9 system. (Mali et al. February 2013).

As used herein, the terms "increase," "increased," "increasing," "improved," (and grammatical variations thereof), describe, for example, an increase of at least about 5%, 10%, 15%, 20%, 25%, 35%, 50%, 75%, 80%, 85%, 90%, 95%, 97%), 98%), 99%), or 100% as compared to a control. In embodiments, the increase in the context of a heterogenous gene or clinical variant thereof, is measured and/or determined via phenotypic assay to assess function of the expressed gene.

As used herein, the term "genomic locus" or "locus" (plural loci) is the specific location of a gene or DNA sequence on a chromosome and, can include both intron or exon sequences of a particular gene. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, introns, exons, promoter sequences, terminators, translational regulatory sequences such as ribosome binding sites and internal ribosome entry sites, enhancers, silencers, insulators, boundary elements, 5' or 3' regulatory sequences, replication origins, matrix attachment sites and locus control regions. As used herein "native locus" refers to the specific location of a host gene (e.g., ortholog to the heterologous gene) in a host animal.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. As used herein, "clinical variant" is a disease gene that comprises one or more amino acid changes as compared to wild type and is thus a mutant gene.

A "normal" or "wild type" nucleic acid, nucleotide sequence, polypeptide or amino acid sequence refers to a naturally occurring or endogenous nucleic acid, nucleotide sequence, polypeptide or amino acid sequence that has not undergone a change. As used herein, the wild type sequence may be a disease gene, but does not comprise a mutation leading to a pathogenic phenotype. It is understood there is a distinction between a wild type disease gene (e.g. those without a mutation leading to a pathogenic phenotype and may be an allele reflective of a "normal" heterogenous population) and clinical variants that comprise one or more mutations of those disease genes and that may have a pathogenic phenotype. In embodiments, the normal gene or wild type gene may be the most prevalent allele of the gene in a heterogenous population.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein. In embodiments, function is determined via one or more phenotypic assays wherein a phenotypic profile for the mutant (disease) gene may be generated.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence As used herein, the term "percent sequence similarity" or "percent similarity" refers to the percentage of near-identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent similarity" can refer to the percentage of near-identical amino acids in an amino acid sequence. Near-identical amino acids are residues with similar biophysical properties (e.g., the hydrophobic leucine and isoleucine, or the negatively-charged aspartic acid and glutamic acid).

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA as DNA construct, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%), 98%), 99%), or 100% as compared to a control. In embodiments, the reduction in the context of a heterogenous gene or clinical variant thereof, is measured and/or determined via phenotypic assay to assess function of the expressed gene.

The term "safe harbor" locus as used herein refers to a site in the genome where transgenic DNA (e.g., a construct) can be added whose expression is insulated from neighboring transcriptional elements such that the transgene expression is fully depend on only the introduced transgene regulatory elements. In certain embodiments, the present invention involves incorporation and expression of transgenic DNA includes transgenes within a safe harbor locus.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

As used herein, the phrase "substantially identical," or "substantial identity" and grammatical variations thereof in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%>nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

"Subject" and "patient" as used herein interchangeably refers to any vertebrate, including, but is not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus or rhesus monkey, chimpanzee, etc.) and a human). In some embodiments, the subject may be a human or a non-human. The subject or patient may be undergoing other forms of treatment. In embodiments, the patient is a human wherein a clinical variant is a sequence of a disease gene from the patient.

"Target gene" as used herein refers to any nucleotide sequence encoding a known or putative gene product. As used herein the target gene may be the chimeric heterologous gene, either in normal or wild type form, or as a clinical variant, or the host animal ortholog of the heterologous gene. The target gene may be a mutated gene involved in a genetic disease, also referred to herein as a clinical variant.

"Target nucleotide sequence" as used herein refers to the region of the target gene to which the Type I CRISPR/Cas system is designed to bind.

The terms "transformation," "transfection," and "transduction" as used interchangeably herein refer to the introduction of a heterologous nucleic acid into a cell. Such introduction into a cell may be stable or transient. Thus, in some embodiments, a host cell or host organism is stably transformed with a polynucleotide of the invention. In other embodiments, a host cell or host organism is transiently transformed with a polynucleotide of the invention. "Transient transformation" in the context of a polynucleotide means that a polynucleotide is introduced into the cell and does not integrate into the genome of the cell. By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid and the plastid genome, and therefore includes integration of the nucleic acid construct into, for example, the chloroplast or mitochondrial genome. Stable transformation as used herein can also refer to a transgene that is maintained extrachromosomally, for example, as a mini-chromosome or a plasmid. In certain embodiments, the nucleotide sequences, constructs, expression cassettes can be expressed transiently and/or they can be stably incorporated into the genome of the host organism, such as in a native, non-native locus or safe harbor location.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

The term "3'untranslated region" or "3'UTR" refers to a nucleotide sequence downstream (i.e., 3') of a coding sequence. It generally extends from the first nucleotide after the stop codon of a coding sequence to just before the poly(A) tail of the corresponding transcribed mRNA. The 3' UTR may contain sequences that regulate translation efficiency, mRNA stability, mRNA targeting and/or polyadenylation. In embodiments, the 3' UTR may be native, or non-native in the context of the chimeric heterologous gene sequence.

"Variant" with respect to a peptide or polypeptide that differs in one or more amino acid sequence by the insertion, deletion, or conservative substitution of amino acids as compared to a normal or wild type sequence. The variant may further exhibit a phenotype that is quantitatively distinguished from a phenotype of the normal or wild type expressed gene. In embodiments, clinical variant refers to a disease gene with one or more amino acid changes as compared to the normal or wild type disease gene.

Transgenic Nematodes

The instant transgenic nematode system comprises a host nematode that comprises a chimeric heterologous gene, wherein the entire host nematode ortholog was removed, either prior to or at the same time the chimeric heterologous gene was installed, and wherein the chimeric heterologous gene is installed at the host nematode ortholog native locus. It is not an aspect of the invention for partial removal, or inactivation without removal, of the host animal ortholog. Further, the heterologous genes are eukaryotic; it is not an aspect of the invention for the heterologous gene to be prokaryotic. In embodiments, the host nematode is a *C. elegans, C. briggsae, C remanei, C. tropicalis*, or *P. pacificus*. (Sugi T et al. Genome Editing in *C. elegans* and Other Nematode Species. Int J Mol Sci. 2016 Feb. 26; 17(3):295.

In embodiments, the heterologous gene is selected from a different species of nematode (e.g. parasitic nematode), an avian, mammal or fish. As disclosed in more details in the Examples, the chimeric heterologous gene replaces the entire nematode ortholog gene at the native locus, accordingly the chimeric heterologous gene must have a homolog as an identified ortholog in the host nematode. In one embodiment, the homolog is of substantial quality when sequence identity between heterolog source and host exceeds 70%. In one embodiment, the homolog is of high quality when sequence identity between heterolog source and host exceeds 50%. In other embodiments, the homolog is good when its identity exceeds 35%. In other embodiments, the homolog is adequate when its identity exceeds 20%. In other embodiments, the homolog is poor but acceptable when its identity is less than 20%. See Example 1 for identification of host nematode orthologs; and, Tables 1 and 5 for a pairing of human genes and nematode orthologs.

In alternative embodiments, the heterologous gene is from a parasitic nematode, which are selected from *Trichuris muris, Ascaris lumbricoides, Ancylostoma duodenale, Necator americanus, Trichuris trichiura, Enterobius vermicularis, Strongyloides stercoralis, Trichinella spiralis, Wuchereria bancrofti, Brugia malayi, Brugia timori, Loa loa, Mansonella streptocerca, Onchocerca volvulus, Mansonella perstans, Mansonella ozzardi, Cooperia punctata, Cooperia oncophora, Ostertagia ostertagi, Haemonchus contortus, Ascaris suum, Aphelenchoides, Ditylenchus, Globodera, Heterodera, Longidorus, Meloidogyne, Nacobbus, Pratylenchus, Trichodorus, Xiphinema, Bursaphelenchus, Dirofilaria immitis, Toxocara canis, Toxocara cati, Ancylostoma braziliense, Ancylostoma tubaeforme, Ancylostoma caninum, Dirofilaria repens*, and *Uncinaria stenocephala*.

In certain embodiments, the heterologous gene is a human gene. In certain embodiments, the human gene is a wild type gene. Provided herein is a transgenic nematode system comprising a host nematode comprising a chimeric heterologous gene optimized for expression in the host nematode wherein the heterologous gene replaced a host nematode gene ortholog and the heterologous gene rescues, or at least partially restores, function of the replaced nematode ortholog. Heterologous genes that rescue function of the replaced nematode ortholog are referred to herein as "wild type" heterologous genes.

In other embodiments, the heterologous gene is a human disease gene. As used herein, "disease gene" refers to a gene involved in or implicated in a disease. In certain embodiments provided herein are transgenic nematodes comprising a heterologous gene that is a human wild type disease gene that has replaced the host nematode ortholog at the native locus. See Example 1 and 7. Those human heterologous disease genes represent targets for drug discovery and drugs that rescue function of human clinical variants.

In embodiments, the chimeric heterologous gene rescues, or at least partially restores, function of the removed host nematode ortholog. Rescue or restoration of function, which is measured in a phenotypic assay, identifies those transgenic nematodes that are validated and may be used as a transgenic control animal. As used herein "validated transgenic control nematode" means a transgenic nematode expressing a chimeric heterologous gene in place of the host nematode ortholog, wherein at least partial function is rescued by expression of the heterologous gene. Rescued function can be from 1% to 100% as compared to wild type host nematode, referred to in the examples and figures as N2.

In addition to quantitative rescue effects, rescue can be qualitative as to essential genes, wherein rescue with a heterologous transgene provides sufficient lifespan and fecundity for establishment of a propagating colony.

In embodiments, rescue of function is measured by analyzing, observing or monitoring the transgenic nematodes in a phenotypic assay as compared to wild type host nematodes and/or null variants. See Example 1 and 3. In embodiments, the phenotypic assay is selected from a measurement of electrophysiology of pharynx pumping, a food race, lifespan extension and contraction assay, movement assay, fecundity assay with egg lay or population expansion, apoptotic body formation, chemotaxis, lipid metabolism assay, body morphology changes, fluorescence changes, drug sensitivity and resistance assays, or a combination thereof. There is no limitation as to the phenotypic assay that may be used, including those developed in the future, provided a useful phenotype profile can be generated for assessing function of the installed chimeric heterologous gene. The above are representative phenotype assays, but others may be used to validate the transgenic nematode, as well as for assessing variants of the heterologous genes.

In embodiments, a phenotype profile of the transgenic nematode is identified from the assay wherein the identified phenotype is selected from electropharyngeogram variant, feeding behavior variant, defecation behavior variant, lifespan variant, electrotaxis variant, chemotaxis variant, thermotaxis variant, mechanosensation variant, movement variant, locomotion variant, pigmentation variant, embryonic development variant, organ system morphology variant, metabolism variant, fertility variant, dauer formation variant, stress response variant, or a combination thereof.

In certain embodiments provided herein are validated transgenic control nematodes of the present system, comprising a chimeric heterologous gene optimized for expression in the host nematode wherein the heterologous gene replaced a host nematode gene ortholog and the heterologous gene rescues function of the replaced nematode ortholog. In embodiments, the heterologous gene is a human disease gene.

In embodiments, the transgenic nematodes further comprise an inducible reporter gene operably linked to an inducible promoter. See U.S. Pat. No. 8,937,213, herein incorporated by reference, which disclose use of inducible and constitutive promoters operably linked to reporter genes. Reporter genes are well known in the art and include luminescent and fluorescent proteins that can be expressed in living cells. Well known examples include GFP, mCherry, mTurquoise and mVenus. In certain embodiments the inducible promoter is from a gene induced by the heterologous gene, or the variant heterologous gene. In certain embodiments, the inducible promoter is from a gene inhibited by the variant heterologous gene.

The present validated transgenic nematodes are prepared via homologous recombination at the native locus of the host nematode ortholog wherein the nematode ortholog is replaced with the heterologous gene. This method is advantageous in that it provides a platform for further testing and modifications and provides an improvement over previously disclosed methods that use amino acid substitution for generation of humanized nematodes expressing clinical variants. The use of gene-swap (i.e. heterologous gene replaces the nematode ortholog at the native locus) avoids the expression level issues that are a challenging problem with extrachromosomal array studies. Instead, CRISPR techniques are deployed to directly mutate at native loci. Farboud B and Meyer B J. Dramatic enhancement of genome editing by CRISPR/Cas9 through improved guide RNA design. Genetics. 2015 April; 199(4):959-71; Paix A et al. High Efficiency, Homology-Directed Genome Editing in *Caenorhabditis elegans* Using CRISPR-Cas9 Ribonucleoprotein Complexes. Genetics. 2015 September; 201(1):47-54.

Gene swap involves removal of the native coding sequence of the host nematode (e.g. *C. elegans*) ortholog and replacement with cDNA from the heterologous gene (e.g., human gene), wherein the exon coding sequences of the heterologous gene are paired with, or interspersed with, host nematode intron sequences. The host intron sequences are derived from a highly expressed host gene and may be further modified for expression of the heterologous exon coding sequences. As used herein "chimeric heterologous gene" refers to a sequence of heterologous (to the host animal) exon coding sequences that are paired or interspersed with the host animal intron sequences. Representative modified host nematode intron sequences are selected from SEQ ID NO: 2; SEQ ID NO: 3 and/or SEQ ID NO: 4. In embodiments, the present transgenic nematodes comprise a chimeric heterologous gene comprising one or more of SEQ ID NO: 2; SEQ ID NO: 3 and/or SEQ ID NO: 4. Those sequences, when used with human exon coding sequences have demonstrated good expression in a host nematode. See SEQ ID NO: 1; SEQ ID NO: 44 and SEQ ID NO: 58.

To execute a gene-swap, the coding sequence from heterologous cDNA is optionally adjusted for optimal expression in the host nematode, e.g., *C. elegans*. In addition to the use of host animal intron sequences paired with heterologous exon coding sequences, optimization includes codon optimization for the host animal and removal of any aberrant splice donor and/or acceptor sites that were generated as a result of the chimeric sequence. Accordingly, in embodiments provided herein are transgenic nematodes comprising a chimeric heterologous gene optimized for expression in the host nematode wherein the heterologous gene replaced a host nematode gene ortholog, wherein the chimeric heterologous gene comprises heterologous exon coding sequences interspersed with artificial host nematode intron sequences.

In embodiments, optimization comprises codon optimization (e.g. removal of rare codons), introduction of host intron sequences into the heterologous cDNA and removal of any aberrant splice sites. For codon optimization, rare codon usage must be avoided to enable sufficient levels of protein translation from a mRNA message. For intron sequences, the artificial host intron sequences are added to the codon optimized heterologous cDNA sequence, which results in improved mRNA stability, and a chimeric sequence. Performing those techniques are well known in the art and online tools exist for performing both. Conveniently, codon optimization and identification of aberrant splice sites are achieve with the *C elegans* codon adapter that encodes optimal amino acid sequence (Redemann S et al., *C. elegans* codon Adapter—GGA, Nat Methods. 2011 March; 8(3):250-2) and NextGene2 which adjust splice donor and acceptor sites for optimal performance (Hebesgaard S M et al., Nucleic Acids Res. 1996 Sep. 1; 24(17):3439-52).

Those chimeric sequences, heterologous cDNA optimized, and artificial host intron sequences added may result in a sequences with highly repetitive sequences that prevent gene synthesis by DNA sequence providers. As a result, the sequence may be hand curated to minimize repeat sequence formation and enable synthesis to proceed from suppliers. The need to hand curate sequence content creates a need for removal of aberrant splice site donor and acceptor site. Online tools exist for identify unintentional splice site donor and acceptor sites. Additional hand curated sequence adjustments are made iteratively until on-line software no longer detects aberrant splice site donor and acceptor sites. Because a given optimization may fail to express properly for unforeseen reasons, three sets of expression-optimized human cDNA are frequently made so that at least three attempts at null rescue can be attempted. See Example 1 and FIG. 1.

In embodiments, the intron sequences provided by the *C. elegans* codon Adapter are synthetic introns that are not ideal for expression. However, the synthetic host intron sequences can be modified to meet certain criteria optimal for expression of the heterologous gene. Those criteria include intron sequences, for expression in a host nematode such as *C. elegans*, that are: from a gene highly expressed native *C. elegans* genes; small (less than 80 bp); do not contain stop codons; are divisible by 3; and, have a low hydropathy index. Host intron sequences that do not meet those criteria can be modified by deleting or changing bases. Host intron sequences meeting the above criteria are likely to not negatively affect gene expression or plasmid building and at the same time, even if un-spliced in synthetic DNA, will retain reading frame and code for peptides with low hydrophobicity content. As a result, functional protein is likely even if all the intron sequences fail to splice.

In some embodiments, the intron position is based on the protein structure. Protein structure can be identified by using published data such as X-ray crystallography. An alignment of orthologs and paralogs is performed. Un-conserved regions are mapped to the structure to find loop regions. The target gene is labeled for loop regions. Amino acid pairs are identified in the loop region that can be coded for a good splice donor and acceptor such as KE, KD, QE, QD, EE, ED, KV, QV, and EV. The introns as disclosed above are inserted between the splice donor and acceptor and the sequence is checked for aberrant splicing as disclosed above.

In certain embodiments, the transgenic control nematodes may be prepared by methods other than homologous recombination into the native locus of the nematode, provided the cDNA of the heterologous gene is optimized for expression in the host nematode by codon optimization, addition of host intron sequences to the cDNA sequence of the heterologous gene and removing aberrant splice donor and acceptor sites. Those alternative methods comprise inserting the optimized chimeric heterologous gene via homologous recombination into a native locus of the nematode wherein a nematode gene ortholog is removed, wherein the heterologous gene rescued, or at least partially restored, function of the removed nematode ortholog; or, inserting the optimized heterologous gene into a non-native locus of the nematode; or, inserting the optimized heterologous gene into a random site of the nematode genome; or, adding the optimized heterologous gene as an expression vector wherein the optimized heterologous gene is not integrated into the nematode genome.

In embodiments are provided transgenic test nematodes, which are based on the validated transgenic control nematode and comprise a variant of the heterologous gene. As used herein, "variant heterologous gene" refers to an expressed gene with one or more amino acid changes as compared to the heterologous gene that was used to prepare the validated transgenic control nematode. Accordingly, a transgenic test nematode comprises a transgenic control nematode that is a modified validated transgenic nematode, wherein the expressed heterologous gene comprises one or more amino acid changes providing a variant of the heterologous gene. The transgenic test nematodes may be used for assessing function of the heterologous variant gene and drug discovery. In embodiments, a transgenic test nematode comprises a chimeric variant heterologous gene, comprising heterologous exon coding sequences interspersed with artificial host nematode intron sequences optimized for expression in the host nematode, wherein the exon coding sequences comprise one or more mutations resulting in an amino acid change as compared to a wildtype reference sequence (wild type heterologous gene of transgenic control animal), and wherein the chimeric variant heterologous gene replaced an entire host nematode gene ortholog at a native locus, and wherein the heterologous gene is a eukaryotic gene.

In embodiments, the variant heterologous gene may be introduced by amino acid swap of the transgenic control nematode or gene swap of a variant containing heterologous gene in as replacement of the unc-18 coding sequence. See Example 2 and 5. In embodiments, the variant heterologous gene is a human disease gene comprising one or more amino acid changes as compared to the wild type disease gene. In embodiments, the variant comprises a single amino acid change wherein the change was installed into the integrated heterologous sequence of the transgenic control animal via a co-CRIPSR method. The resulting transgenic animals are transgenic test animals (e.g. nematode or zebrafish). See Example 2. In certain embodiments, the mutations (of the heterologous exon coding sequence) are created from a pool of DNA repair templates each containing one or more mutations. In other embodiments, the variant comprises more than one amino acid change. In certain embodiments, those mutations are created from a pool of DNA repair templates each containing two or more mutations. Variants with more than one amino acid change, as compared to the wild type gene, may be a known clinical variant or a combination of two or more variants of the same gene. The combination of clinical variants in one variant heterologous transgenic test animal may be beneficial for assessing function of variants as to their synergistic, antagonistic, additive etc. function as measured in phenotypic assays.

Like *Drosophila* studies, electrophysiology measurements in *C. elegans* on functional variants can provide a rich and diverse set of phenotyping data. Sorkaç A et al. In Vivo Modelling of ATP1A3 G316S-Induced Ataxia in *C. elegans* Using CRISPR/Cas9-Mediated Homologous Recombination Reveals Dominant Loss of Function Defects. PLoS One. 2016 Dec. 9; 11(12). These published studies were done by making "humanizing" mutations at native loci. A homology alignment is used to determine where conserved positions occur between the human gene and its animal model ortholog. Clinical variants are then mapped to the sequence alignment and, if they occur at a conserved amino acid, the clinical variant can be installed by CRISPR as an amino-acid-swap which substitutes the native amino acid with the amino acid change seen in the patient.

In embodiments, the variant heterologous gene is a human clinical variant. Accordingly, when at least partial rescue of function is achieved with expression of the heterologous gene, the system (comprising validated transgenic nematodes) becomes valid for installation of clinical variants (test transgenic nematodes). Six classes of clinical variants can be installed (Pathogenic, Likely Pathogenic, Uncertain Significance, Likely Benign, Benign, and the unassessed). On average, dbSNP data indicates 80% of known variants are unassessed and nearly half (40%) of the remaining assessed variants are Variants of Uncertain Significance (VUS). (NCBI) Variation Viewer. Installation of known Pathogenic and Benign variants helps determine how conserved are the existing assignments when installed into the human cDNA expressing nematode model. When most of the pathogenic and benign variants give expected activities (e.g., phenotype) in the humanize nematode model the system then is valid for assessment of pathogenicity of VUS and unassigned variants.

In embodiments, methods are provided herein for assessing function of a human clinical variant, comprising the steps of culturing a test transgenic nematode, wherein the variant heterologous gene is a human clinical variant; and, performing a phenotypic screen to identify a phenotype of the test transgenic nematode, wherein a change in phenotype as compared to a control transgenic nematode comprising a wildtype heterologous gene (e.g. corresponding validated transgenic nematode) indicates an altered function of the clinical variant in the test transgenic nematode. The phenotypic screens and identified phenotypes are disclosed above and are the same as those used when validating the transgenic control nematode for rescue of function.

In embodiments, the phenotypic screen is a food race wherein decreased time to reach food, as compared to the control transgenic nematode, indicates pathogenicity of the human clinical variant. In embodiments, the methods further comprise classifying the human clinical variant as pathogenic, likely pathogenic, uncertain significance, likely benign, or benign following the phenotypic screen.

In certain embodiments, the transgenic test nematode comprises an inducible promoter operably linked to a reporter gene, wherein the promoter is from a gene induced by expression of the human clinical variant gene, wherein the method for assessing function of a human clinical variant comprises culturing a test transgenic nematode, wherein the variant heterologous gene is a human clinical variant and, observing the inducible report gene expression, whereby human clinical variant genes with altered function are identified as pathogenic or likely pathogenic when the inducible reporter gene is expressed.

In further embodiments provided herein are methods using the transgenic test nematode system for drug screening. For humanized platforms exhibiting pathogenic activity with a given installed variant, screens of novel and existing compounds can be performed in efforts to find drug candidates with capacity to restore function back towards wild type. In embodiments, the methods for screening therapeutic agents to treat altered function of a human clinical variant, comprises placing a test transgenic nematode in a medium comprising a test compound, wherein the variant heterologous gene is a human clinical variant identified as pathogenic, likely pathogenic, unknown significance or unassigned; incubating the test transgenic nematode with the test compound for a period from 2 minutes to 7 hours; and, performing a screening assay, whereby therapeutic agents are identified from the test compounds when the outcome of the screening assay is deemed positive. An altered phenotype back towards wildtype is conserved positive. The screening assays are phenotypic assays disclosed above, including fluorescent assay wherein transgenic test nematode further comprises an inducible promoter operably linked to a reporter gene wherein the promoter is from a gene inhibited in response to expression of the human clinical variant, whereby therapeutic agents are identified when the inducible reporter gene is expressed. See Example 4.

In embodiments provided herein are methods for screening therapeutic agents to treat altered function of a human clinical variant. Those methods comprise use of a present transgenic test animal. In certain embodiments, those methods comprise placing a present transgenic test nematode, with an identified behavioral or molecular phenotype that is different from an identified phenotype of a control transgenic nematode expressing a wildtype heterologous gene, in a medium comprising a test compound, wherein the variant heterologous gene is a human clinical variant; incubating the test transgenic nematode with the test compound for a period from 2 minutes to seven days; and, performing a phenotypic assay to identify a post-test compound behavioral or molecular phenotype of the test transgenic nematode, whereby therapeutic agents are identified from the test compounds when the post-test compound phenotype is more similar, as compared to the phenotype of the test transgenic nematode, to the phenotype of the control transgenic nematode.

EXAMPLES

The following examples are put forth so as to provide those of ordinary skill in the art with a complete disclosure and description of how to use the embodiments provided herein and are not intended to limit the scope of the disclosure nor are they intended to represent that the Examples below are all of the experiments or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

Example 1: Preparation of Validated Transgenic Nematode with Heterologous Gene as a Transgenic Control Animal Provided herein are transgenic nematodes and methods of preparing same for assessing function of expression of a heterologous gene, wherein the heterologous gene is first optimized for expression in a host nematode creating a chimeric heterologous gene wherein the exon coding sequences are heterologous (e.g. human inserted into nematode) and the intron sequences are sourced from or otherwise optimized for the host animal (e.g. nematode) and then inserted into a native locus of the nematode via homologous recombination resulting in the removal of the nematode ortholog, wherein expression of the heterologous gene rescues function of the replaced nematode ortholog. In certain embodiments, the heterologous gene is a human gene.

By way of example to demonstrate the general principle of significant conservation of function occurs when a human gene replaces an orthologous gene in an animal model, the human cDNA for STXBP1 (syntaxin binding protein 1; a protein implicated in epilepsy) was substituted into the unc-18 ortholog locus in *C. elegans* using the gene-swap humanization method, which is a modified version plasmid-based transgenesis using selection-marker to discover donor homology mediated edits (Dickinson D and Goldstein B. CRISPR-Based Methods for *Caenorhabditis elegans* Genome Engineering. Genetics. 2016 March; 202(3):885-901.). The result is the creation of a STXBP1 transgenic control animal.

It is understood orthologs can be identified using a number of tools, including the DIOPT-DRSC Integrative Ortholog Prediction Tool, BLAST or reciprocal BLAST searches, and methods disclosed in E. Vallender, *Methods* 2009 September; 49(1) 50-55. Genes are good candidates for gene replacement when they have high sequence similarity and/or conserved function. STXBP1/unc-18-sequence identity is 59% and sequence similarity is 75% using DIOPT-DRSC Integrative Ortholog Prediction Tool (Hu et al., BMC Bioinformatics. 2011 Aug. 12:357) See Table 1, below for a partial list of human disease genes and their *C. elegans* orthologs.

Gene Swap involves removal of the native coding sequence of the host nematode *C. elegans* ortholog and replacement with human cDNA from the disease gene (STXBP1). See FIG. 1. To execute a gene-swap the coding sequence from human (or other organism) cDNA needs to be adjusted for optimal expression in *C. elegans*. In embodiments, are provided methods for optimization of heterologous cDNA to create expression-optimized coding sequence using codon optimization, addition of artificial intron sequences, sourced from or optimized for the host animal, and removal of aberrant splice sites. That process results in a chimeric heterologous gene with exon coding sequences from a heterologous gene and intron sequences from the host animal that is then inserted into the native locus of the host animal resulting in expression of the heterologous gene and removal of the host animal ortholog gene. The host animal ortholog gene may be removed first as a knock-out, followed by addition of the heterologous gene at the same location, or as presented in the instant example at the same time via homologous recombination.

The STXBP1 cDNA sequence was optimized for expression in the host nematode (*C. elegans*) via codon optimization, addition of nematode intron sequences and removal of undesirable splice sites. For codon optimization, rare codon usage in the heterologous gene was avoided to enable sufficient levels of protein translation from mRNA message. In the instance of STXBP1, the following expression-optimized cDNA sequence with nematode introns inserted (lower case) was used (SEQ ID NO. 1):

ATGGCTCCTATAGGTTTAAAAGCAGTTGTTGGTGAAAAAATCATGCAC

GACGTCATCAAGAAGGTCAAGAAGAAGGGAGAGTGGAAGGTCCTCGTCGT

CGACCAACTCTCCATGCGTATGCTCTCCTCCTGCTGCAAGATGACCGACA

TCATGACCGAGGGAATCACCATCGTCGAGGACATCAACAAGCGTCGTGAG

CCACTCCCATCCCTCGAGGCCGTCTACCTCATCACCCCATCCGAGAAGTC

CGTCCACTCCCTCATCTCCGACTTCAAGGACCCACCAACCGCCAAGTACC

GTGCCGCCCACGTCTTCTTCACCGACTCCTGCCCAGACGCCCTCTTCAAC

GAGCTCGTCAAGTCCCGTGCCGCCAAGGTCATCAAGACCCTCACCGAGAT

CAACATCGCCTTCCTCCCATACGAGTCCCAAGTCTACTCCCTCGACTCCG

CCGACTCCTTCCAATCCTTCTACTCCCCACACAAGgtacttgagatcctt aaacgcagtcgaaaattggtaattttacagGCCCAAATGAAGAACCCAAT

CCTCGAGCGTCTCGCCGAGCAAATCGCCACCCTCTGCGCCACCCTCAAGG

AGTACCCAGCCGTCCGTTACCGTGGAGAGTACAAGGACAACGCCCTCCTC

GCCCAACTCATCCAAGACAAGCTCGACGCCTACAAGGCCGACGACCCAAC

CATGGGAGAGGGACCAGACAAGGCCCGTTCCCAACTCCTCATCCTCGACC

GTGGATTCGACCCATCCTCCCCAGTCCTCCACGAGCTCACCTTCCAAGCC

ATGTCCTACGACCTCCTCCCAATCGAGAACGACGTCTACAAGTACGAGAC

CTCCGGAATCGGAGAGGCCCGTGTCAAGGAGGTCCTCCTCGACGAGGACG

ACGACCTCTGGATCGCCCTCCGTCACAAGCACATCGCCGAGGTCTCCCAA

GAGGTCACCCGTTCCCTCAAGgtaagttcctccactagaaatatcaggtg ctataattgtgttcagGACTTCTCCTCCTCCAAGCGTATGAACACCGGAG

AGAAGACCACCATGCGTGACCTCTCCCAAATGCTCAAGAAGATGCCACAA

TACCAAAAGGAGCTCTCCAAGTACTCCACCCACCTCCACCTCGCCGAGGA

CTGCATGAAGCACTACCAAGGAACCGTCGACAAGCTCTGCCGTGTCGAGC

AAGACCTCGCCATGGGAACCGACGCCGAGGGAGAGAAGATCAAGGACCCA

ATGCGTGCCATCGTCCCAATCCTCCTCGACGCCAACGTCTCCACCTACGA

CAAGATCCGTATCATCCTCCTCTACATCTTCCTCAAGAACGGAATCACCG

AGGAGAACCTCAACAAGCTCATCCAACACGCCCAAATCCCACCAGAGGAC

TCCGAGATCATCACCAACATGCCCACCTCGGAGTCCCAATCGTCACCGA

CTCCACCCTCCGTCGTCGTTCCAAGCCAGAGCGTAAGgtgagtgatttta aacattatctgtacttaaattataaattctctattcagGAGCGTATCTCC

GAGCAAACCTACCAACTCTCCCGTTGGACCCCAATCATCAAGGACATCAT

GGAGGACACCATCGAGGACAAGCTCGACACCAAGCACTACCCATACATCT

CCACCCGTTCCTCCGCCTCCTTCTCCACCACCGCCGTCTCCGCCCGTTAC

GGACACTGGCACAAGAACAAGGCCCCAGGAGAGTACCGTTCCGGACCACG

TCTCATCATCTTCATCCTCGGAGGAGTCTCCCTCAACGAGATGCGTTGCG

CCTACGAGGTCACCCAAGCCAACGGAAAGTGGGAGGTCCTCATCGGATCC

ACCCACATCCTCACCCCACAAAAGCTCCTCGACACCCTCAAGAAGCTCAA

CAAGACCGACGAGGAGATCTCCTCCTAA

The presence of modified nematode intron sequences added to the codon-optimized cDNA improves mRNA stability. Both codon optimization and addition of nematode intron sequences was achieved using the *C. elegans* codon Adapter (Redemann S et al., *C. elegans* codon Adapter—GGA, Nat Methods. 2011 March; 8(3):250-2) that enabled derivation of a codon-optimized nucleic sequence encoding the desired amino acid sequence and identifies splice donor and acceptor sites with insertion of artificial introns. The output file contains highly repetitive sequence that prevents gene synthesis by most DNA sequence providers. As a result, the sequence was hand curated to minimize repeat sequence formation and enable synthesis to proceed from suppliers.

Additionally, the artificial introns provided by the *C. elegans* Codon Adapter were substituted with modified introns selected from small introns in highly expressed native *C. elegans* genes. The modified introns maintain the coding frame and, if they were translated, the amino acid sequence would not contain stop codons and would have a low hydropathy index. In the humanized STXBP1, the sequences of the modified nematode introns used were 1.
(SEQ ID NO: 2)
gtacttgagatccttaaacgcagtcgaaaattggtaattttacag 2.
(SEQ ID NO: 3)
gtaagttcctccactagaaatatcaggtgctataattgtgttcag
and 3.
(SEQ ID NO: 4)
gtgagtgattttaaacattatctgtacttaaattataaattctctattc
ag.

The need to hand curate sequence content and substitute artificial nematode introns with modified introns creates a need for removal of aberrant splice sites. Accordingly, aberrant splice site donor and acceptor site are removed from the chimeric heterologous cDNA sequence following codon optimization and addition of nematode intron sequences. An online software tool, NetGene2 (Hebesgaard S M et al., Nucleic Acids Res. 1996 Sep. 1; 24(17):3439-52), is used to identify unintentional splice site donor and acceptor sites. Additional hand curated sequence adjustments are made iteratively until on-line software no longer detects aberrant splice site donor and acceptor sites.

The optimized STXBP1 cDNA sequence was obtained as a gene block from IDTDNA, Inc, and sub-cloned into an intermediate plasmid (pNU1347). The Gibson assembly method for enzymatic assembly of DNA molecules (Gibson et al. 2009 *Nat. Methods* May; 6(5):343-5) was used to assemble the creation of an intermediate plasmid. Next, a donor homology plasmid DNA construct was made for gene-targeted precision editing via activation of homologous recombination activity.

Donor homology plasmid for targeted editing is typically made from 5 parts. Parts 1 and 4 are donor homology arms. In general, each homology arm sequence is chosen to flank site of DNA substitution. Next, the donor homology is chosen to be between 750 to 500 base pairs in size and is obtained by PCR of genomic wildtype N2 DNA. Often a quality sgRNA (single guide RNA) site does not occur directly at a start and stop codon. As a result, cleavage site at the 5' end must occur at position distal to the start codon. To avoid interference with promoter elements, the 5' cleavage site chosen to be downstream of the start codon. This cleavage position becomes the bounds for the downstream end of the left-side donor homology arm. From this cleavage site the sequence is scrolled upstream 500 bp where a search for a good PCR primer sequence is initiated.

For STXBP1 gene insertion, the left side donor homology arm used the following synthetic oligonucleotide sequences GAGCTCGGTACCTCGCGAATGCATCTAGATgcatagtacgcagtacagtccc (SEQ ID NO: 5) and CATcgatgcactcacaattaacctgc (SEQ ID NO: 6) to prime PCR amplification on an N2 template DNA. A similar procedure is performed to select the right side donor homology arm, with an alternative requirement that the sgRNA creating its bound occurs before the stop codon, which is a location enabling endogenous performance of 3' UTR elements to be maintained after genome editing. A stop codon can be introduced in the expression-optimized human cDNA prior to the right site donor homology arm. For STXBP1 right side homology arm the following synthetic oligonucleotide sequences ggttgcaggttaattgtgagtgcatcgATGggaAGCcccGG-GAGCacgggtgggATGGCTCCTATAGGTTTA AAAGCAGTT (SEQ ID NO: 7) and GAAGT-TATgcctgcagcgcgacatgtttaaTTTATTAGGAG-GAGATCTCCTCGTCG (SEQ ID NO: 8) were used to prime PCR amplification on N2 template. The result is a "vestigial" sequence element occurring between the human cDNA and the 3' UTR. On the left side donor homology arm, the existing endogenous coding sequence was not vestigial and became integral to STXBP1 expression as it's start codon and intervening sequence is integral to expression of the human cDNA sequence.

If homology alignments and known biology indicate the N-terminus of the human cDNA is likely to be tolerant of extra sequence, the endogenous start codon and translated sequence can be left as a "peptide" tag on the human cDNA. Alternatively, if human cDNA cannot tolerate N term tagging, or if the peptide sequence is hydrophobic, it is best to configure operonic expression with a SL2 splice site, or insert a self-cleaving peptide sequence (P2A, T2A or intein) to occur between the endogenous coding and the human cDNA.

Part 2 for the donor-homology plasmid was a PCR amplification of optimized cDNA for STXBP1 from pNU1347.

Part 3 for the plasmid was a hygR rescue cassette PCR amplified from pNU1298.

Part 5 for the donor-homology plasmid was a plasmid backbone sequence PCR amplified from pUC57 The final hSTXBP1 donor homology plasmid (pNU1469) targeting STXBP1 insertion at the unc-18 locus was assembled from the 5 parts using the Gibson assembly technique.

Following the creation of a donor homology plasmid, a transgenesis mixture was created containing (pNU1469 (hSTXBP1 targeting), sgRNA plasmid pNU1485 (targeting taattgtgagtgcatcgacg site) (SEQ ID NO: 9), sgRNA plasmid pNU1486 (targeting gcactctgTCATATGTCACG site) (SEQ ID NO: 10), pNU1027 (Cas9 expressing). The mixture was injected into gonads of a host *C. elegans* using standard microinjection techniques. (Evans T C. Transformation and microinjection (Apr. 6, 2006). In the *C. elegans* Research Community WormBook. doi/10.1895/wormbook.1.108.1). Injected components used were standard for single copy insertion driven by selection marker for transgenic animal discovery (Frøkjaer-Jensen C et al. Single-copy insertion of transgenes in *Caenorhabditis elegans*. Nat Genet. 2008 November; 40(11):1375-83). Injected animals were introduced to NGM growth plates containing hygromycin (2 mg/ml). 72 hrs after drug exposure, surviving animals were individually recovered as founders to non-selective plates. Once a population was established 24-48 hrs later, the founder animal was screened by PCR for target site insertion. Founder populations were found as hits when they test positive for targeted insertion. Individuals from founder population were isolated for a second round of founder analysis. When a PCR test was found to be positive on an individual as homozygous for targeted insertion, a second-round of founders was selected from first round of founders. After populations were established, PCR was applied to the founder individual to identify a strain as confirmed for desired transgenesis. The result was creation of a humanized hSTXBP1 gene knock-in strain.

Frequently it is prudent to remove the selection marker and enable full activity potential of the transgene by bringing the native sequence 3'UTR immediately after the human transgene sequence. For the confirmed homozygote for hSTXBP1 gene knock-in strain, a knock-out procedure was used to remove the hygR cassette. The hygR cassette region was removed using standard co-CRISPR methods (Kim H et al. A co-CRISPR strategy for efficient genome editing in *Caenorhabditis elegans*. Genetics. 2014 August; 197(4): 1069-80). The hSTXBP1 gene knock-in strain was injected with a co-CRISPR transformation mix (pNU1668odn, sgRNA RNA (targeting GAAGCTCAACAAGACCGACG) (SEQ ID NO: 11), sgRNA RNA (targeting actaGA-CATATGAcagagtg) (SEQ ID NO: 12), CEH2536odn, sgRNA RNA (targeting GCTACCATAGGCACCACGAG) (SEQ ID NO: 13), and cas9 protein). The pNU1668odn was GCTCCTCGACACCCTCAAGAAGCTCAACAAGACC-GATGAAGAAATTTCTTCTTAGcag agtgcggggtaccgaaaagaatcgacaattgacgaa (SEQ ID NO: 14) oligonucleotide sequence which acts as a donor homology instructing precision removal of the hygR cassette from the hSTXBP1 gene knock-in strain. The co-CRISPR regent CEH2536odn was CACTTGAACTTCAATACGGCAA-GATGAGAATGACTGGAAACCGTACCGCATGCGGT GCCTATGGTAGCGGAGCTTCACATGGCTTCAGAC-CAACAGCCTAT (SEQ ID NO: 15) oligo nucleotide sequence which acts as donor homology instructing insertion of a R100C change in dpy-10 which creates Rol heterozygote animals. Injected populations with high numbers of rolling animals were screened by PCR for presence of desired edit. Rol animals were isolated and after population is established, the Rol animal are screened by PCR for loss of hygR cassette. New founder populations were established from the F2 progeny plates testing positive for hygR removal. Plates testing positive as homozygous for hygR removal were selected as selection cassette removed strain. DNA sequencing confirmed the native unc-18 3' UTR occurs immediately after the stop codon of the STXBP1 coding sequence.

Figure 2:
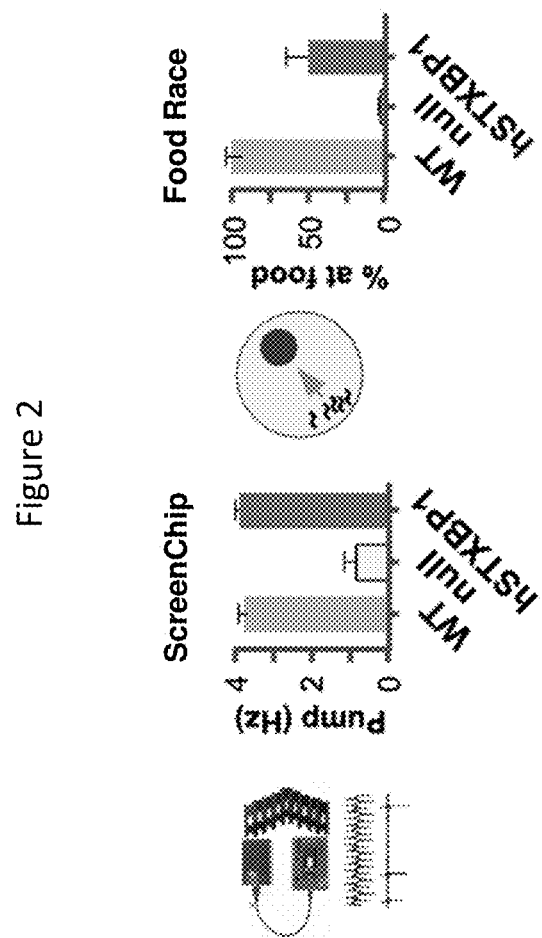
FIG. 2 shows two phenotypic behavior assays (ScreenChip and Food Race) used to observe the behavior phenotype profile of the transgenic nematodes with expression of a heterologous gene STXBP1 (syntaxin binding protein 1) (e.g. transgenic control animal) as compared to wildtype (e.g. non-transgenic wild-type animal) and a null variant (e.g. knock-out control animal).

Unlike the hSTXBP1 gene knock-in strain, the hygR-cassette-removed hSTXBP1 animal exhibited a significant capacity to restore synaptic transmission as measured by the Food Race and ScreenChip assays. See FIG. 2. In embodiments, expression of the heterologous STXBP1 transgene controlled by native unc-18 promoter and 3' UTR sequence was found to rescue function of the removed nematode ortholog, as observed and measured with various phenotypic screens. Provided herein is a validated transgenic control nematode.

The above methods created a transgenic control animal, and which was used to establish a behavior phenotype profile for the transgenic animal expressing the heterologous STXBP1 gene. In embodiments, as exemplified above, the methods used to generate a transgenic control nematode or a humanized control nematode. Those animals, as detailed in Example 2, were used as background animals to generate a test transgenic animal wherein one or more mutations were introduced into the exon coding sequence which results in at least one amino acid change in the expressed protein (i.e. variants of the wildtype heterologous gene). In embodiments, the transgenic control animal comprises a chimeric heterologous gene inserted into a native locus of the host animal wherein the exon coding sequences are heterologous (e.g. human) and the intron coding sequences are modified sequences sourced from the host animal, or a close relative. In the above example, those intron sequences were generated from highly expressed native *C. elegans* genes.

TABLE 1

Human heterologous genes and corresponding nematode orthologs.

| Human Gene | Nematode Gene Ortholog | Human Gene | Nematode Gene Ortholog | Human Gene | Nematode Gene Ortholog |
|---|---|---|---|---|---|
| AARS | aars-2 | ABCA4 | abt-2 | ABCB4 | pgp-9 |
| ABCA3 | abt-4 | ABCB11 | pgp-9 | ABCC2 | mrp-2 |
| ABCC6 | mrp-2 | ARFGEF2 | agef-1 | BRD2 | bet-1 |
| ABCD1 | pmp-4 | ASAH1 | asah-1 | BRIP1 | dog-1 |
| ACADM | acdh-7 | ATL1 | atln-1 | CACNA1A | unc-2 |
| ACTA1 | act-4 | ATP13A2 | catp-5 | CACNA1C | egl-19 |
| ACTA2 | act-4 | ATP1A2 | eat-6 | CACNA1D | egl-19 |
| ACTB | act-4 | ATP1A3 | eat-6 | CACNA1F | egl-19 |
| ACTG1 | act-4 | ATP6V0A2 | unc-32 | CACNA1H | cca-1 |
| ACTN2 | atn-1 | ATRX | xnp-1 | CACNA1S | egl-19 |
| ADA | C06G3.5 | AVPR2 | ntr-1 | CACNB2 | ccb-1 |
| ADAR | adr-2 | BBS7 | osm-12 | CACNB4 | ccb-1 |
| ADSL | adsl-1 | BCKDHA | bckd-1A | CAPN3 | clp-7 |
| AGPAT2 | acl-2 | BEST1 | best-24 | CASK | lin-2 |
| ALDH7A1 | alh-9 | BICD2 | bicd-1 | CAV3 | cav-1 |
| ALDOB | aldo-1 | BLM | him-6 | CBS | cbs-2 |
| ANK1 | unc-44 | BMPR1A | sma-6 | CDKN1B | cki-2 |
| ANK2 | unc-44 | BRCA1 | brc-1 | CDKN1C | cki-2 |
| ANK3 | unc-44 | BRD1 | lin-49 | CFTR | mrp-6 |
| CHAT | cha-1 | COL4A5 | let-2 | DYNC2H1 | che-3 |
| CHD8 | chd-7 | CREBBP | cbp-1 | DYRK1A | mbk-1 |
| CHEK2 | T08D2.7 | CRX | ttx-1 | DYSF | fer-1 |
| CHRNA2 | unc-63 | CRYAB | hsp-12.2 | EGR2 | egrh-1 |
| CHRNA4 | unc-63 | CSRP3 | mlp-1 | EHMT1 | set-11 |
| CHRNA7 | acr-16 | CTNNB1 | hmp-2 | EMC2 | emc-2 |
| CHRNB2 | lev-1 | CTSD | asp-4 | EMC3 | emc-3 |
| CHRND | unc-63 | CUBN | ZC116.3 | EMC6 | emc-6 |
| CHRNE | unc-63 | CYP27A1 | cyp-44A1 | ENPP1 | C27A7.1 |
| CHRNG | lev-1 | CYP4V2 | cyp-31A2 | EP300 | cbp-1 |
| CLCN1 | clh-3 | DDX3X | laf-1 | ERCC2 | xpd-1 |

TABLE 1-continued

Human heterologous genes and corresponding nematode orthologs.

| Human Gene | Nematode Gene Ortholog | Human Gene | Nematode Gene Ortholog | Human Gene | Nematode Gene Ortholog |
|---|---|---|---|---|---|
| CLCNKB | clh-3 | DIAPH1 | cyk-1 | ERCC6 | F53H4.6 |
| CLN3 | cln-3.1 | DMD | dys-1 | ETHE1 | ethe-1 |
| CNGA3 | tax-4 | DNM2 | dyn-1 | FGFR1 | egl-15 |
| CNTN4 | rig-6 | DOCK8 | F46H5.4 | FGFR2 | egl-15 |
| CNTNAP2 | nlr-1 | DPYD | dpyd-1 | FGFR3 | egl-15 |
| COL4A1 | let-2 | DYNC1H1 | dhc-1 | FKBP10 | fkb-4 |
| FKTN | T07D3.4 | GCDH | F54D5.7 | IFIH1 | drh-1 |
| FLNA | fin-1 | GCK | hxk-1 | IGHMBP2 | eri-7 |
| FLNB | fin-1 | GLB1 | bgal-1 | ITGA2B | pat-2 |
| FLNC | fin-1 | GLI2 | tra-1 | JUP | hmp-2 |
| FOXG1 | fkh-2 | GLRA1 | glc-3 | KANK1 | vab-19 |
| FOXP1 | fkh-7 | GOLGA7 | Y57G11C.33 | KCNJ11 | irk-1 |
| FOXP2 | fkh-7 | GOSR2 | memb-1 | KCNJ2 | irk-2 |
| GAA | aagr-2 | GPD1L | gpdh-2 | KCNJ5 | irk-2 |
| GABRA1 | lgc-36 | GRIA3 | glr-2 | KCNMA1 | slo-1 |
| GABRB3 | gab-1 | GRIN1 | nmr-1 | KCNQ1 | kqt-3 |
| GABRG2 | lgc-37 | GRN | pgrn-1 | KCNQ2 | kqt-1 |
| GARS | gars-1 | HADH | F54C8.1 | KCNQ3 | kqt-1 |
| GATA3 | elt-1 | HNF4A | nhr-64 | KCNV2 | exp-2 |
| GATA4 | elt-2 | HPS5 | W09G3.6 | KDM6A | utx-1 |
| GBA | gba-3 | HSD17B4 | dhs-28 | KIF11 | bmk-1 |
| GBA2 | hpo-13 | HSPB1 | hsp-25 | KIF1A | unc-104 |
| KIF1B | unc-104 | MET | F11E6.8 | MYO1A | hum-5 |
| KIF5A | unc-116 | MFSD8 | Y53G8AR.7 | MYO6 | spe-15 |
| KMT2D | set-16 | MGAT1 | gly-14 | NALCN | unc-77 |
| KRAS | let-60 | MPI | ZK632.4 | NF2 | nfm-1 |
| L1CAM | lad-2 | MTOR | let-363 | NKX2-5 | ceh-28 |
| LAMA1 | lam-3 | MYH11 | nmy-1 | NLGN4X | nlg-1 |
| LAMA2 | lam-3 | MYH14 | nmy-1 | NOTCH1 | lin-12 |
| LIPA | lipl-1 | MYH3 | myo-5 | NOTCH2 | lin-12 |
| LMNA | lmn-1 | MYH6 | myo-2 | NOTCH3 | lin-12 |
| LRP2 | lrp-1 | MYH7 | myo-3 | NPC1 | ncr-1 |
| MAN2B1 | aman-1 | MYH7 | myo-3 | NPEPPS | pam-1 |
| MAP2K1 | mek-2 | MYH9 | nmy-1 | NPHS2 | sto-2 |
| MAP2K2 | mek-2 | MYL2 | mlc-1 | NR2E3 | fax-1 |
| MCCC1 | mccc-1 | MYL3 | mlc-5 | NRAS | let-60 |
| MCCC2 | F02A9.4 | MYLK2 | mlck-1 | NSDHL | hsd-2 |
| MEGF10 | ced-1 | MYO15A | hum-4 | OTOF | fer-1 |
| PAH | pah-1 | PNPLA6 | ZK370.4 | PTCHD1 | ptr-2 |
| PANK2 | pnk-1 | POGZ | row-1 | PTPN11 | ptp-2 |
| PAX2 | pax-2 | POLG | polg-1 | RAB7A | rab-7 |
| PAX3 | pax-3 | POU3F4 | ceh-6 | RAD50 | rad-50 |
| PAX6 | vab-3 | PQBP1 | pqbp-1.2 | RARS2 | rars-2 |
| PCCA | pcca-1 | PRICKLE1 | prkl-1 | RBFOX1 | asd-1 |
| PEX6 | prx-6 | PRKAG2 | aakg-1 | REEP1 | T19C3.4 |
| PFKM | pfk-1.1 | PRKG1 | egl-4 | RP1 | F27C1.13 |
| PHEX | nep-2 | PSEN1 | sel-12 | RP1L1 | F27C1.13 |
| PHF8 | jmjd-1.1 | PSMA1 | pas-6 | RP2 | rpi-2 |
| PHKA1 | C14B9.8 | PSMC2 | rpt-1 | RPE65 | bcmo-2 |
| PIK3R1 | aap-1 | PSMC4 | rpt-3 | RPGRIP1 | mks-5 |
| PKD2 | pkd-2 | PSMC5 | rpt-6 | RPS6KA3 | rskn-1 |
| PLA2G6 | ipla-2 | PSMD2 | rpn-1 | RRM2B | rnr-2 |
| PLEC | vab-10 | PSMD3 | rpn-3 | SCNN1B | unc-8 |
| PLP1 | nmgp-1 | PTCH1 | ptc-3 | SDHA | sdha-1 |
| SERPINA1 | srp-2 | SLC2A1 | fgt-1 | SPTA1 | spc-1 |
| SETD1B | set-2 | SLC2A2 | fgt-1 | SPTAN1 | spc-1 |
| SETD5 | set-9 | SLC35C1 | nstp-10 | SPTLC2 | sptl-2 |
| SGCA | sgca-1 | SLC37A4 | F4768.10 | STAT3 | sta-1 |
| SGCG | sgn-1 | SLC3A1 | atgp-2 | STXBP1 | unc-18 |
| SHH | qua-1 | SLC4A1 | abts-1 | SYNE1 | anc-1 |
| SIX3 | ceh-32 | SLC9A6 | nhx-5 | TBC1D24 | tbc-7 |
| SLC12A3 | nkcc-1 | SMAD3 | sma-2 | TBX5 | tbx-2 |
| SLC12A6 | kcc-2 | SMAD4 | sma-4 | TCF4 | hlh-2 |
| SLC17A5 | slc-17.2 | SMARCA2 | swsn-4 | TCIRG1 | vha-6 |
| SLC19A3 | folt-1 | SMARCA4 | swsn-4 | TECTA | T01D3.6 |
| SLC22A5 | Oct-1 | SMC1A | him-1 | TGFB2 | daf-7 |
| SLC25A13 | K02F3.2 | SMPD1 | asm-2 | TGFBR1 | daf-1 |
| SLC25A22 | F55G1.5 | SPAST | spas-1 | TH | cat-2 |
| SLC26A2 | sulp-8 | SPEN | din-1 | TMC1 | tmc-2 |
| SLC26A4 | sulp-8 | SPG7 | ppgn-1 | TMEM216 | mks-2 |
| TMEM67 | mks-3 | TTN | unc-22 | VRK1 | vrk-1 |
| TNNI3 | tni-4 | TTR | R09H10.3 | WAS | wsp-1 |
| TNNT2 | tnt-4 | TUBA1A | mec-12 | WASHC5 | T05E7.3 |
| TPO | pxn-1 | TUBB4A | tbb-4 | WRN | wrn-1 |

TABLE 1-continued

Human heterologous genes and corresponding nematode orthologs.

| Human Gene | Nematode Gene Ortholog | Human Gene | Nematode Gene Ortholog | Human Gene | Nematode Gene Ortholog |
|---|---|---|---|---|---|
| TRPM1 | gon-2 | TYR | tyr-3 | WWOX | dhs-7 |
| TRPM4 | gtl-2 | VPS11 | vps-11 | ZIC2 | ref-2 |
| TRPV4 | ocr-4 | VPS39 | vps-39 | ZMYND11 | bra-1 |

Example 2: Preparation of a Transgenic Test Animal from a Transgenic Control Animals as Nematode with Variant Installed in Either the Native Ortholog Locus or Humanized Transgene Background Provided herein are compositions of gene-edited nematodes as transgenic test animals and methods of preparing same for assessing function of a variant heterologous gene. The test transgenic nematodes are modified transgenic nematodes prepared according to Example 1 wherein the expressed heterologous gene comprises one or more amino acid changes as compared to wild type reference sequence providing a variant of the heterologous gene.

When rescue of function is achieved with chimeric human cDNA install, the system becomes valid for installation of clinical variants. Six classes of clinical variants can be installed (Pathogenic, Likely Pathogenic, Uncertain Significance, Likely Benign, Benign, and the unassessed). On average, dbSNP data from Variation Viewer (Agarwala et al., Nucleic Acids Res. 2018 Jan. 4; 46(D1):D8-D13) indicates 80% of known variants are unassessed and nearly half (40%) of the remaining assessed variants are Variants of Uncertain Significance (VUS).

Installation of known Pathogenic and Benign variants helps determine how conserved are the existing assignments when installed into the human cDNA expressing animal model. When most of the well-established pathogenic and benign variants give expected activities in the humanized animal model the system then is valid for assessment of pathogenicity of VUS and unassigned variants.

A co-CRISPR technique is used to create variant installations as representations of the amino acid changes occurring in patient variants, CRISPR techniques are deployed to directly mutate amino acids at any loci. Kim H et al. A co-CRISPR strategy for efficient genome editing in *Caenorhabditis elegans*. Genetics. 2014 August; 197(4):1069-80; Farboud B and Meyer B J. Dramatic enhancement of genome editing by CRISPR/Cas9 through improved guide RNA design. Genetics. 2015 April; 199(4):959-71; and, Paix A et al. High Efficiency, Homology-Directed Genome Editing in *Caenorhabditis elegans* Using CRISPR-Cas9 Ribonucleoprotein Complexes. Genetics. 2015 September; 201(1):47-54. The clinical variant can be installed by CRISPR as an amino-acid-swap which substitutes the native amino acid with the amino acid change seen in the patient. For making point mutations to install an amino acid change, the homology-mediated mutagenesis of a dpy-10 locus is used to detect which injections have a high transformation potential. Injections are performed with a dpy-10 sgRNA and a dpy-10 oligonucleotide repair template in the injection mix. Also included in the injection mix is a set of sgRNAs targeting a clinical variant editing locus, another repair template instructing for content of clinical variant edit, and Cas9 protein. Typically, 20 animal gonads are injected with approximately 10-50 nl of injection mix. 3-5 days later Jackpot plates are identified as populations with high frequency of Rol phenotype. Rol animals are isolated for population expansion. After egg lay, adults are harvested, and PCR amplified to detect presence of desired edit. The PCR is specifically designed to distinguish between homozygous mutant, homozygous wild-type and heterozygous animals. Animals from populations PCR positive for the mutation are isolated for population expansion and, after egg lay, the adult is PCR tested again to detect presence of homozygosity. Mutations are confirmed by sequencing.

Another method to achieve creation of variant installation is to mutate the donor homology plasmid as described in Example 1 using standard site directed mutagenesis techniques (e.g. Stratagene Quick-Change protocol and kit), or as synthetic plasmid, and then integrate the mutated donor homology plasmid into the genome with CRISPR. In all cases, variant installs are confirmed by PCR, PCR+restriction digest, and/or sequencing, either before or after phenotyping.

A set of hSTXBP1 transgenic test animals were made from the hSTXBP1 transgenic control animal according to Example 1. Three variants installations of established pathogenic alleles were used to created three types of transgenic test animals (the R406H, R292H, and R388X strains). Because these variants occur at conserved positions in unc-18, variant installs were also made in the native unc-18 gene locus. This allowed for the comparison of variant activities between the humanized (hSTXBP1) and native (unc-18) loci. The specific donor homologies and sgRNA sites for variant installs in both the hSTXBP1 and unc-18 loci are listed in the following table.

TABLE 2

| variant (target) | Donor homology ODN | sgRNA |
|---|---|---|
| p.R406H (hSTXBP1) | TCCTCGACGCCAACGTCTCCAC CTACGACAAGATCCACATTAT TCTTCTTTATATTTTTCTTAAA AATGGTATTACTGAGGAGAAC CTCAACAAGCTCATCCAACAC GCCCAA (SEQ ID NO: 16) | CCTCAAGAACGGAATCA CCG (SEQ ID NO: 17) |

TABLE 2-continued

| variant (target) | Donor homology ODN | sgRNA |
|---|---|---|
| p.R406H (unc-18-p.R405H) | TTGATTGACCCAGCCGTGCGG TGTGAAGACCGCCTGCACTTG ATTCTGTTGTACATTCTTTCCA AGAATGGAAT (SEQ ID NO: 18) | ACAACAGAATCAATCTG AGG (SEQ ID NO: 19) TGTACAACAGAATCAAT CTG (SEQ ID NO: 20) |
| p.R292H (hSTXBP1) | TCCTCGACGAGGACGACGACC TCTGGATCGCCCTCCACCATAA ACATATTGCTGAGGTCTCCCA AGAGGTCACCCGTTCCCTCAA Ggta (SEQ ID NO: 21) | CCGTCACAAGCACATCG CCG (SEQ ID NO: 22) |
| p.R292H (unc-18-p.R290H) | TTCTGCTCGATGAGAATGATG ATTTATGGGTTGAAATGCACC ATAAGCACATCGCAGTGGTTT CACAAGAAGTCACAAAGAACT TGAAAAGTTC (SEQ ID NO: 23) | ATGATTTATGGGTTGAAA TG (SEQ ID NO: 24) TGTGACTTCTTGTGAAAC AA (SEQ ID NO: 25) |
| p.R388X (hSTXBP1) | CCGTCGACAAGCTCTGCCGTG TCGAGCAAGACCTCGCTATGG GTACTGATGCTGAAGGTGAAA AAATTAAAGATCCGATGTAAG CCATCGTCCCAATCCTCCTCGA CGCCAACGTCTC (SEQ ID NO: 26) | GCCATGGGAACCGACGCC GA (SEQ ID NO: 27) |
| p.R388X (unc-18-p.R387X) | AAGGTTGAACAAGATTTGAGT ACCGGAATCGACGCCGAGGGA GAGCGTGTCCGTGACGCCATG TGACTCATGGTCCCACTCTTGA TTGACCCAGCCGTGCGGTGTG AAGACCGCCTC (SEQ ID NO: 28) | AGUACCGGAAUCGACGCA GA (SEQ ID NO: 29) ACGGCUGGGUCAAUCAAA AG (SEQ ID NO: 30) |
| p.S42P (unc-18-p.S42P) | GCGCGTGGAATGTTCTCATCGT TGACACCCTAGCCATGCGTAT GCTCCCATCATGTTGTAAGATG CATAACATCATGGAAGgtaattaca cttgatattttaattccttc (SEQ ID NO: 31) | TCGTTGACACCCTAGCCA TG (SEQ ID NO: 32) AAAATGCACAATATTATG GA (SEQ ID NO: 33) |
| p.P462L (unc-18-p.P461L) | atagacgtgtcaatttacagACCGGCCGC AAGAAAACCTGGACTCTCACC AAGAAGGAGCGTCCACATGAG CAAGTTTACCAATCTTCCCGCT GGGTTCCAGTT (SEQ ID NO: 34) | agACCGGCCGCAAGAAGAC G (SEQ ID NO: 35) GAUUGGUAAACUUGCUCG UG (SEQ ID NO: 36) |

Significant behavior phenotypic differences between hSTXBP1 and unc-18 loci were observed when function was assessed on the clinical variants by food race and ScreenChip assays. See Example 3.

Provided herein is a transgenic nematode system for assessing function of an expressed variant heterologous protein, comprising a test transgenic nematode comprising a chimeric heterologous gene comprising heterologous exon coding sequences, wherein the coding sequences comprise one or more mutations resulting in an amino acid change as compared to wildtype, and host nematode intron sequences optimized for expression in a host nematode wherein the chimeric heterologous gene replaced a host nematode gene ortholog at a native locus, wherein the expressed heterologous gene comprises one or more amino acid changes as compared to expressed wild type heterologous gene providing a variant of the heterologous gene.

In certain embodiments provided herein is a humanized transgenic nematode system for assessing function of an expressed human variant protein, comprising a test transgenic nematode comprising a chimeric heterologous gene comprising human exon coding sequences, wherein the coding sequences comprise one or more mutations resulting in an amino acid change as compared to wildtype, and host nematode intron sequences optimized for expression in a host nematode wherein the chimeric heterologous gene replaced a host nematode gene ortholog at a native locus, wherein the expressed heterologous gene comprises one or more amino acid changes as compared to expressed wild type heterologous gene providing a variant of the heterologous gene Example 3: Assessing Function of a Human Clinical Variant by Identifying Phenotype Defects of Transgenic Test Animals Provided herein are methods for assessing function of a human clinical variant utilizing a variant-installed humanized nematode as a transgenic test animal (Example 2) and, as a control for comparison, an unmodified wild-type humanized nematode as a transgenic control animal (Example 1). The methods comprise culturing a transgenic test animal (e.g. nematode), wherein the variant heterologous gene is a human clinical variant; and, performing a phenotypic behavior assay to identify a behavior phenotype of the transgenic test animal, wherein a change in phenotype is observed in comparison to a transgenic control animal. The observation of a relative phenotypic change indicates an altered function of the clinical variant occurs in the transgenic test animal.

Also provided herein is a method for assessing function of human clinical variants utilizing inducible reporter gene expression. That method comprises culturing a transgenic test animal as a nematode, wherein the variant heterologous gene is a human clinical variant and wherein the transgenic nematode further comprises an inducible promoter operably linked to a reporter gene, wherein the promoter is from a gene induced by expression of the human clinical variant gene; and, observing the inducible report gene expression, whereby human clinical variant genes with altered function are identified as pathogenic or likely pathogenic when the inducible reporter gene is expressed. Quantified or qualitative analysis of the expressed reporter gene is an observed phenotype as disclosed herein.

Figure 3:
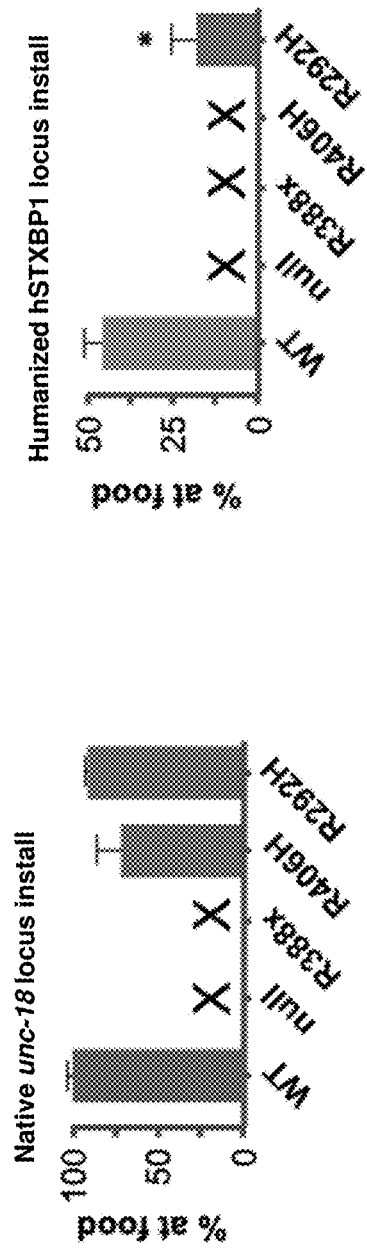
FIG. 3 shows a chemotaxis phenotypic behavior assays (Food Race) used to observe the deviant phenotypes of the transgenic control and transgenic test nematodes wherein the clinical variant was prepared using site directed mutagenesis in either the unc-18 native locus or in the humanized hSTXBP1 strain.

The transgenic test nematodes prepared in Example 2, with the pathogenic clinical variants installed in a humanized locus (R292H, R406H and R388X) were compared to a set of animals prepared using targeted amino acid swap into the native locus (R405H, R290H, R387X). These animals were screened using the food race assay to detect capacity of the test transgenic nematode to exhibit coordinated movement in efforts to perform chemotaxis towards a food source. The assay was performed in 1 hr. For assays at the native locus, most of the N2 animals (no transgene) can reach food and only the R388 variant has a statistically-significant incapacity to reach food. In contrast, the variants installed at the humanized locus all showed significant activity defects relative to transgenic control animals. See FIG. 3. In summary, all pathogenic variant installs into the hSTXBP1 strain exhibited greater levels of deviant activity when compared to installs into the unc-18 locus of the N2 strain.

TABLE 3

| 1 hr food race | amino-acid-swap: variant install in unc-18 native gene | gene-swap: variant install in hSTXBP1 humanized line |
|---|---|---|
| R406H | 80% | 5% |
| R292H | 100% | 50% |
| R388X | 0% | 0% |
| S42P | 50% | No data |
| P462L | 100% | No data |

In some instances, a shorter time point in a behavior phenotype assay can be used to reveal other biological differences. For instance, to detect haploinsufficiency defects in heterozygotes of null alleles of the native unc-18 gene, a 15 and 30 min timepoint allowed better detection of movement defects. See FIG. 4.

Figure 4:
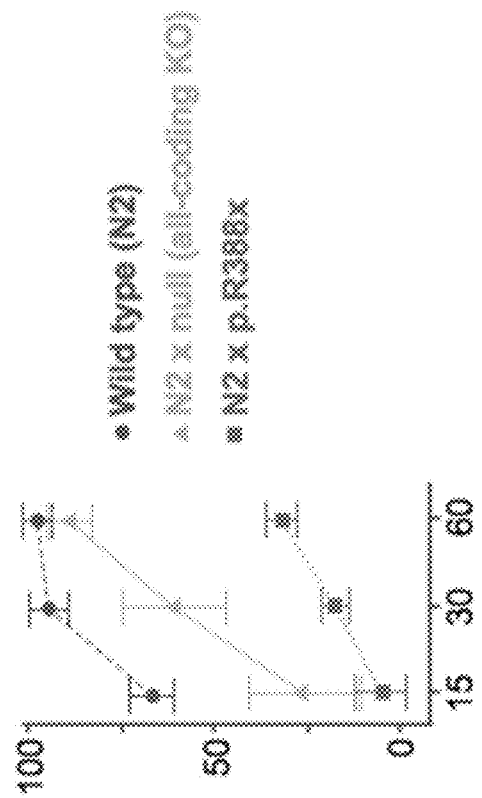
FIG. 4 shows three (3) time points during the Food Race assay of wild type vs a unc-18 gene deletion heterozygote vs a R387X clinical variant heterozygote in the unc-18 locus.

FIG. 4 shows that 15 min provides the highest differential between wild type and the haploinsufficient heterozygotes. Intriguingly the R388x variant has a slower response compared to the full gene KO. The decreased coordinated movement activity in R388x implies the assay is detecting a dominant negative effect. This is a phenomenon that is very difficult to capture ex vivo, cell culture, or rodent animal models. In the nematode system, detection of haploinsufficiency required observations to be made in the developing nervous system of juvenile larval forms (L3-L4), where delayed neuronal development effects are most pronounced. When the same behavior assay was performed on 48 hr old adults and no phenotypic behavior difference was observed. As a result, some of the variables affecting the capacity to observe haploinsufficiency are 1) time to measure from start of race, 2) the age of animal, and 3) the genetic composition of the animal. Other yet-to-be-determined variables (food source, growth media, temperature, etc.) are likely to have pronounced effects on capacity to measure functional variation.

Some of transgenic test nematodes with the clinical variants disclosed above were also tested in a ScreenChip assay, which monitors the electrophysiology of pharyngeal pumping recordings of individual animals as they enter a microfluidic channel. See U.S. Pat. No. 9,723,817, the contents of which are incorporated herein by reference. Electrodes embedded in a microfluidic chip measure the changes in voltage from animals trapped in microfluidic channels. C. elegans pharyngeal pumping causes a large rhythmic electrical output. As a result, the major component of recordings is pharynx pumping activity, which is recorded as an electropharyngeograms (EPG) (Raizen D and Avery L. Electrical activity and behavior in the pharynx of Caenorhabditis elegans. Neuron. 1994 March; 12(3):483-95). Loss of pharynx pumping can be a healthspan measure; EPG rates drop to sporadic or non-existent immediately prior to death. Neuronal defects in serotonergic signaling due to genetic deficiencies (Brock T et al. Precision deletion of the entire coding sequence of the mod-5 locus causes increase in pharyngeal pumping frequency. Micropublication: biology. 2017 July 6), lifespan/healthspan (Russell J et al. Electrophysiological measures of aging pharynx function in C. elegans reveal enhanced organ functionality in older, long-lived mutants. J Gerontol A Biol Sci Med Sci. 2017 Nov. 18) or neurodegeneration (Weeks J et al. Microfluidic EPG Recordings Show Striking Pharyngeal Pumping Phenotype in a C. elegans Alzheimer's Disease Model. Micropublication: biology 2006) can be measured as alterations of standard pumping rate.

The electrophysiology data from a ScreenChip is similar to an electrocardiogram signal. Depolarization and repolarization cycles of the pharynx food-pumping organ create a dominant and rhythmic contributor to the electrophysiology signal. Various sodium, potassium and calcium ion channels are major contributors to the observed electrical flux. Additional contributors are various ATP-driven ion pumps. Presynaptic inputs have a neuromodulatory effect on rhythmic pumping behavior. For instance, loss of presynaptic unc-18 which is needed for coordinated neurotransmitter release results in a decreased pumping frequency when unc-18 is absent from the animal.

Transgenic test nematodes generated by amino acid swap at conserved positions in the unc-18 locus were tested by ScreenChip for alterations in pumping dynamics. An animal was introduced into the sensor region of the ScreenChip microfludics chamber. A 120 second recording of electrophysiology was made. Additional animals were analyzed similarly by serial introduction and analysis in the chamber. On average, multiple animals were assayed to enable increased statistical power (typically n= or >15). Many parameters were extracted from the signal, including frequency, amplitude, interpump interval, and pump duration.

Figure 5:
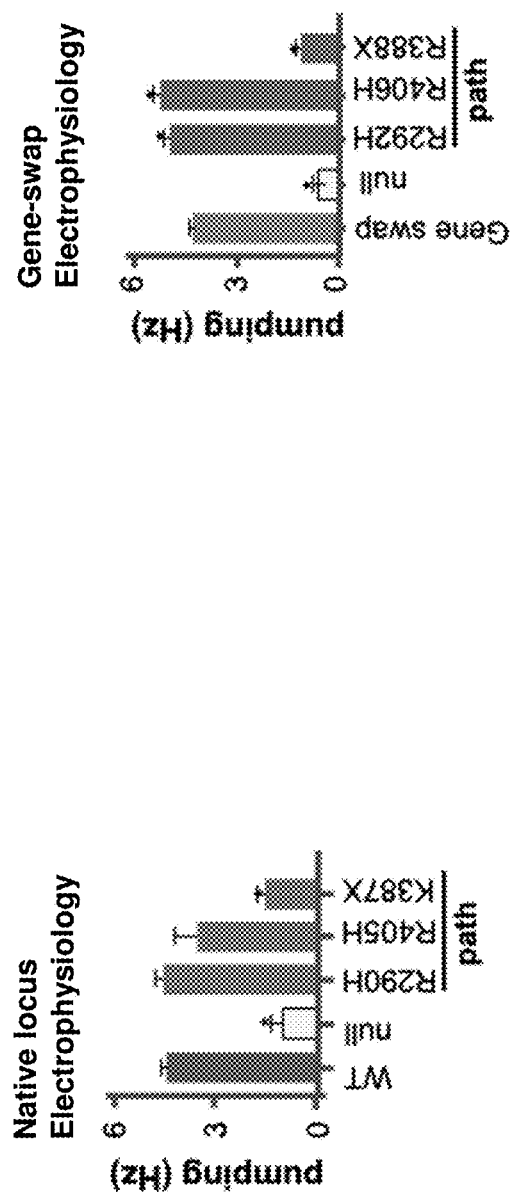
FIG. 5 shows the phenotypic behavior assay (ScreenChip) used to observe the behavior phenotype of transgenic test nematodes (R388X, R406H and R292H) in either the unc-18 native locus or in the humanized hSTXBP1 strain.

Clinical variants installed in native locus of unc-18, in general, did not have a dramatic effect unless they lead to a dramatic compromise of protein coding. For instance, R388X is truncated variation that can express only ⅔ of normal protein coding and its creation as a transgenic test animal resulted in a severely compromised animal as assayed by ScreenChip. The R405H strain also show a statistically significant deficiency of function while R290H strain appear to have wild type behavior. In contrast, clinical variant installs into the humanized hSTBP1 locus all exhibited significant defects. Consistent with the R387X variant in the native unc-18 locus, the R388X variant in hSTBP1 also exhibited deficiency of function. Surprisingly, both the R406H and the R292H variants in hSTXBP1 exhibited a statistically-significant excitatory phenotype. See FIG. 5.

Other phenotypic behavior assays may be used to identify a behavior phenotype of the transgenic test nematode that comprises a clinical variant of a heterologous gene. Those include lifespan assay, brood size assay, egg lay assay, apoptotic assay, chemotaxis assay, body morphology changes, drug sensitivity and resistance assay, or dauer formation, each of which is disclosed below. The transgenic test animals may be tested in any one behavior phenotype assay, or they tested in a panel of assays to determine a behavior phenotype profile for the test transgenic nematode. As detailed in subsequent examples, the behavior phenotype or behavior phenotype profile of each transgenic test nematode may be used to screen for therapeutic agents that alter the behavior phenotype so that it is more similar to the behavior phenotype of the matching transgenic control animal (phenotype rescue). The matching transgenic control animals are those as disclosed in Example 1, wherein the wild-type (or most common normal allele), in chimeric form as disclosed in Example 1, is introduced into the native locus of the nematode replacing the nematode ortholog gene.

The lifespan assay measures the extension and contraction of lifespan of individual animals. As applied to the transgenic test animals of example 2, particular clinical variants installed in the humanized or native gene may result in an altered lifespan phenotype, such as a shorter lifespan with a smaller percentage of a population of worms surviving past three weeks. Lifespan (alternatively "healthspan") is assayed in several ways, including the staining of a population of animals with a dye that fluoresces when animals have died, or by monitoring the movement of a population of worms continuously over a period of weeks.

The brood size assay provides information about the total reproductive potential of a group of worms. As applied to the test transgenic nematode strains of example 2, particular clinical variants that are installed in the humanized or native gene may result in an altered brood size phenotype, such as a decrease brood size, i.e., a smaller number of total progeny on average for a population. This phenotype is assayed in a variety of methods, such as by allowing worms to lay eggs and later counting, via manual or automated methods, the number of resultant progeny.

The egg lay assay provides information about the number of eggs laid in a prescribed period of time, and the temporal pattern of egg laying. As applied to the transgenic test animal of example 2, particular clinical variants that are installed in the humanized and native gene may result in an altered egg laying phenotype, such as a change to the temporal pattern of egg-laying, i.e., a longer interval between bouts of egg laying.

The apoptotic assay provides information about the number of apoptotic corpses in a nematode's body. This can be assayed by exposing the animals to a dye that stains apoptotic corpses and then imaging the location and intensity of the dye. As applied to the transgenic test animals of example 2, particular clinical variants that are installed in the humanized or native gene may result in an altered apoptotic corpse phenotype, such as a change to the number or size of apoptotic corpses detected.

The chemotaxis assay provides information about the physical response of the nematode to chemical stimuli. Worms are placed on an agar arena that has opposing chemicals or volatile point sources. After allowing a gradient to develop, worms are placed in a central location and locomote towards attractive chemicals or away from repulsive chemicals. A chemotaxis index is computed as describes in Wormbook Methods. Hart, Anne C., ed. Behavior (Jul. 3, 2006), *WormBook*, ed. The *C. elegans* Research Community, WormBook, doi/10.1895/wormbook.1.87.1. As applied to the transgenic test animal of example 2, particular clinical variants that are installed in the humanized or native gene may result in an altered chemotaxis index, such as a decrease in the taxis response to a chemoattractant.

The body morphology changes assay provides information about the morphology of the worm, including size and shape of the overall worm as well as particular body structures, such as the gut and intestines, the pharynx, the vulva, and gonad. As applied to the transgenic test animal of Example 2, particular clinical variants that are installed in the humanized or native gene may result in an altered body morphology, such as a decrease in the overall size of the nematode.

The drug sensitivity and resistance assay provide information about the responses of worms to particular drugs and chemical compounds, e.g., aldicarb and ivermectin. Worms are exposed to chemicals for a set period of time and then responses are tabulated for both control and experimental worms. As applied to the transgenic test animals of example 2, particular clinical variants that are installed in the humanized or native gene may result in a sensitivity to a drug, such as a faster paralysis response than control worms when exposed to aldicarb.

The dauer formation assay provides information about rates and timing of entry into the alternative life state of dauer. Following exposure to a dauer inducing pheromone or harsh environmental conditions, L1 worms start a transition to enter dauer which is a long-lived alternative to the normal third larval (L3) life state. In this assay, worms are scored according to whether they are unable to enter the dauer state or are dauer constitutive, i.e., must enter dauer regardless of environmental conditions. As applied to the transgenic test animals of Example 2, particular clinical variants that are installed in the humanized or native gene may result in altered dauer formation, such as a dauer constitutive development.

Example 4: Methods for Screening Therapeutic Agents to Treat Altered Function of a Human Clinical Variant Using a Transgenic Test Animal Provided herein are methods for screening therapeutic agents to treat altered function of a human clinical variant. In embodiments, that method comprises placing a transgenic test nematode, with an identified, or pre-determined, behavior phenotype, or behavior phenotype profile, that is different from an identified, or pre-determined, behavior phenotype of a (matching) transgenic control nematode expressing a wildtype heterologous gene, in a medium comprising a test compound, wherein the variant heterologous gene is a human clinical variant; incubating the test transgenic nematode with the test compound for a period from 0.5 hours to 72 hours; and, performing at least one phenotypic behavior assay identify a post-test compound behavior phenotype of the test transgenic nematode, whereby therapeutic agents are identified from the test compounds when the post-test compound behavior phenotype is more similar, as compared to the behavior phenotype of the test transgenic nematode, to the behavior phenotype of the control transgenic nematode. In other words, test compounds are identified when they rescue the behavior phenotype of the test transgenic nematode.

The test transgenic nematodes of Example 2 comprising a clinical variant, identified as pathogenic or likely pathogenic, can be used to screen therapeutic agents to treat a subject with a particular clinical variant. Therapeutic agents are selected on their ability to rescue a behavior phenotype in any of the phenotypic behavior assays disclosed above or trigger a biosensor response in the test transgenic nematodes.

This is accomplished by identifying the approximate concentration range of effectiveness for each drug tested; ranking the drugs for their relative effectiveness on rescuing each individual gene variant (e.g., behavior phenotype reverts to that of the transgenic control animal); and, measure a dose response curve (DRC) for selected therapeutic agents, to generate quantitative $EC_{50}$ values (the concentration of drug at which a phenotype is altered by 50% of maximal). DRC data would reveal which drug is most effective in remedying a phenotype caused by a variant allele.

By using a whole animal early on in the drug discovery phase, the quality of drug leads is increased—side effects become more apparent and drugs with undesirable properties do not enter the more expensive lead optimization stage.

Example 5: Transgenic Control and Test Nematode Systems and their Use with Clinical Variants Implicated in Autism Spectrum Disorder (ASD); Validation of the Transgenic Systems Via Phenotype Profile Autism gene homologs from select genes of Autism Spectrum Disorder (ASD) are used to prepare validated transgenic nematodes and test transgenic nematodes. The most impactful ASD gene are the SFARI category 1 genes. *C. elegans* orthologs were identified for 21 of 24 genes (Table 4). Ten of the autism genes had strong lethal phenotypes in loss of function alleles of their homolog, of which, 6 had sequence similarity in excess of 40%. Three of the six genes were chosen for exploring in gene humanization formats (KMT5B, PTEN and CHD81.

TABLE 4

| gene-symbol | gene-name | reports | homolog | sequence similarity | function |
|---|---|---|---|---|---|
| CUL3 | Cullin | 13 | cul-3 | 69% | lethal |
| NAA15 | N(alpha)-acetyltransferase | 6 | hpo-29 | 62% | lethal |
| KMT5B | lysine methyltransferase | 8 | set-4 | 56% | lethal |
| TBR1 | T-box protein | 19 | tbx-8 | 55% | lethal |
| PTEN | phosphatase and tensin homolog | 46 | daf-18 | 45% | lifespan/state |
| CHD8 | chromodomain helicase DNA binding protein | 27 | chd-7 | 44% | lethal |
| MYT1L | Myelin transcription factor like | 15 | ztf-11 | 37% | lethal |
| ARID1B | AT rich interactive domain | 33 | let-526 | 35% | lethal |
| ASH1L | Ash1-like protein | 10 | lin-59 | 35% | lethal |
| TRIP12 | Thyroid hormone receptor interactor | 13 | hecd-1 | 34% | lethal |
| DYRK1A | Dual-specificity tyrosine kinase | 32 | mbk-1 | 53% | movement impaired |
| SYNGAP1 | synaptic Ras GTPase activating protein | 40 | gap-2 | 49% | undetected |
| GRIN2B | NMDA receptor | 42 | nmr-2 | 48% | memory defects |
| ANK2 | Ankyrin | 12 | unc-44 | 45% | paralyzed |
| SCN2A | v-gated sodium channel | 49 | unc-77 | 39% | pharynx pumping variant |
| DSCAM | Down syndrome cell adhesion molecule | 7 | igcm-1 | 36% | neuron expressed, absent pheno |
| SHANK3 | SH3 and multiple ankyrin repeat protein | 61 | shn-1 | 35% | pharynx pumping variant |
| POGZ | Pogo transposable element with ZNF domain | 21 | row-1 | 34% | embryonic expressed, absent pheno |
| SETD5 | SET domain containing protein | 21 | set-9 | 34% | extended lifespan |
| KATNAL2 | Katanin p60 subunit | 7 | R09E10.5 | 31% | pharynx expressed, absent pheno |
| KMT2A | Lysine (K)-specific methyltransferase | 14 | F01D4.5 | 26% | neuro and pharynx expressed expressed, absent pheno |
| ADNP | Activity-dependent neuroprotector homeobox | 21 | (n.d)* | (n.d) | (n.d) |
| ASXL3 | Additional sex combs like | 15 | (n.d) | (n.d) | (n.d) |
| RELN | Reelin | 44 | (n.d) | (n.d) | (n.d) |

Humanization is explored for phenotype profiling in autism genes with high homology to *C elegans*. The PTEN gene is chosen because it is expected to act as a positive control. Prior work indicates ectopic expression of the PTEN gene is sufficient to rescue loss of function defects in its ortholog, daf-18 (Liu J and Chin-Sang I D. *C. elegans* as a model to study PTEN's regulation and function Methods. 2015 May; 77-78:180-90). The KMT5B is chosen because an enzymatic function as a lysine methylase function might be sufficient to replace function of its ortholog, set-4. The human sequence of CHD8 is large at 2581 amino acids. Further it has lowest sequence identity of the three genes chosen. It therefore is less likely to rescue function when a CHD8 configuration is inserted in the chd-7 ortholog locus. These genes are important for autism research because a significant number of reports linking it to autism and yet, of the 718 variants, 699 variants remain unassessed. PTEN is important for autism and cancer research and from 341 reported variants there are 197 either unassessed or assigned as Variants of Uncertain Significance (VUS). The smaller KMT5B has recently been shown to be involved in development and autism and of its 273 variants only one is assigned pathogenicity and an another is a VUS.

CHD8.

Gene-swap humanization in *C. elegans* is used to model clinical variants in the CHD8, PTEN, and KMT5B genes. The *C. elegans* ortholog of CHD8 is chd-7. Prior work on chd-7 function indicates that loss-of-function is likely to result in lethality. A 593 bp deletion allele (tm6139) leads to a frame shift (×11) and occurs early in the protein sequence prior to the helicase domain. As a result, a severely truncated loss-of-function null is expected to have occurred. Expression-optimized human cDNA for CHD8 is inserted into the chd-7 locus using left sgRNA site (GCAGATTACACAAT-GATGGG SEQ ID NO: 37) and right sgRNA site (TGCAGAGGATGCTGCAGCCG SEQ ID NO: 38). The long length of CHD8 at 7743 base pairs requires the synthesis of a gene that has at least 6 modified host introns, which are needed to achieve an average intron splicing interval occurring every 1500 bp. In the gene insertion, a vestigial peptide coding for 20 amino acids of chd-7 will remain in the genome. To mitigate the peptide's effect on human transgene function, a T2A self-cleaving peptide is introduced between the coding sequences.

PTEN.

The *C. elegans* ortholog of PTEN is daf-18. Loss of function in daf-18 indicates the gene is critical but not essential for life. Existing deletion alleles (tm5288, tm5119, and ok480) do not eliminate growth and fecundity. Instead variants in daf-18 have a propensity to lead to entry into the alternative life state of dauer. This extended lifespan state has lower fecundity leading to delayed population expansion. The PTEN gene is protein phosphatase of 579 amino acids in length. Only 3 modified host introns are needed for insertion of an expression-optimized human cDNA content as replacement for the daf-18 gene. Left and right side sgRNA site are chosen for gene insertion (GTGCTTGGCA-CATCTGGAGG (SEQ ID NO: 39) and GTGCCCGGAGC-TACATCCAG (SEQ ID NO: 40)). Insertion of human cDNA occurs at the 5th amino acid position of daf-18. A T2A self-cleaving sequence is inserted between amino acid 5 of daf-18 and human PTEN sequence.

KMT5B.

The *C. elegans* ortholog of KMT5B is set-4. Loss of function of set-4 by RNAi or deletion allele (tm1835) result in animal lethality. The KMT5B is a histone H4 lysine methyltransferase and is predicted to modulate the activity of dual-specificity phosphatases. At 885 amino acid in length, an expression-optimized KMT5B will only require the use of 3 modified host intron sequences to satisfy the intron need. Left and right side sgRNA site are chosen for gene insertion (GTCATTGAGTGATCCGAGCG SEQ ID NO: 41) and TTATGATTTAGGATCGTGAG (SEQ ID NO: 42)). Insertion of human cDNA occurs at the 20th amino acid position of set-4. A T2A self-cleaving sequence is inserted between amino acid 20 of set-4 and human KMT5B sequence.

For clinical variants installed in the CHD8 and KMT5B humanized transgenics, the functional deficiency may be so severe as to cause an inability to create the variant as a homozygous animal. Three attempts at homozygosity are made by harvesting self-propagations from 12 progeny isolated from a confirmed heterozygote. After three attempts at homozygosity, the chance that a clinical variant allele has eluded isolation as a homozygote drops to less than 0.001%. As a result, an installed variant that cannot be isolated in a homozygous state is inherently a highly defective and Pathogenic-assignable variant. For more mild variants, a quantifiable phenotypic defect is highly probable if the variant is of Likely Pathogenic capacity. For homozygotes that can propagate, the clinical variants is screened by assays that detect phenotype defects of dauer formation, shortened lifespan, egg lay defects, burst vulva frequency, starvation hypersensitivity, and chemical hypersensitivity to paraquat and selenium. A milestone is achieved when at least one phenotypic assay can measure altered function in a clinical variant relative to its positive control of a wildtype humanize line. The ability to see loss of phenotype in pathogenic variants is expected. Yet, if a known pathogenic variant remains elusive of phenotypic consequence, the environmental conditions of the rescue assay will be screened (temperature, timing of endpoints, food source, growth media, chemical stressors, etc) will be added to the rescue assay in attempt to enhance the phenotypic sensitivity of a given rescue assay. A milestone is achieved when a majority of pathogenic variants exhibit altered phenotypes that are statistically significant for difference from wildtype.

These transgenic test nematodes, comprising clinical variants, can be used in methods to further assess function of the clinical variants and therapeutic agent screening.

Example 6: Additional Validated Control and Transgenic Test Nematode System and Use with Clinical Variants TP53. For the human TP53 gene, the *C elegans* ortholog was established to be the cep-1 gene based on shared molecular functions within the cell. Yet the level of sequence identity is so distant that sequence alignment does not exceed the basal alignment identity between two unrelated sequences. Yet because function is conserved between the proteins, a transgenic strain was made according to Example 1 that replaced the chimeric heterologous gene for the nematode cep-1 ortholog with the coding sequence from human TP53. sgRNA sites were selected at the 5' and 3' side of the cep-1 coding sequence. The 5' sgRNA recognition sequence was ATACCCGATTCGCAGGACAT (SEQ ID NO: 43) in the second exon of cep-1. The 3' sgRNA recognition sequence was aattaggcgattaaaccagg (SEQ ID NO: 44) in the 3'utr of the cep-1 gene. Donor homology arms were amplified from the *C. elegans* genome and designed to have perfect homology with the cut sites. The primers used for amplification were designed using well known and understood techniques. The TP53 sequence was codon optimized according to Example 1. Three modified host introns were added to the sequence. It was optimized for synthetic DNA production and proper splicing as detailed earlier. The unc-119 rescue cassette was included after the coding sequence. This cassette is flanked by two loxP sites and contains 988 bp of the unc-119 promoter from *C. briggsae*, 846 bp of the unc-119 genome coding sequence from *C. briggsae* and 324 bp of the tbb-2 3'utr from *C. elegans*. The orientation of this rescue cassette is in reverse to the cep-1/TP53 gene. These components were cloned in the pUC57 backbone using PCR and Gibson as described earlier and confirmed by DNA sequencing. As in Example 1, an injection mix was made. Microinjections were performed into unc-119 (ed3) III mutant animals. These animals have an uncoordinated movement phenotype which is rescued by the presence of the donor homology plasmid or genome integration. The progeny of the injected animals were screened for movement rescue. Genome integration was confirmed by PCR testing and sequencing as described in Example 1. The resulting transgene is predicted to rescue apoptotic foci defects seen in the cep-1 null animal.

The following genes also are identified targets (e.g. heterologous genes) for gene-swap at a native loci. The table is not exhaustive but is meant to provide exemplar heterologous genes that have appropriate homologs in a host nematode (e.g., C. elegans).

TABLE 5

| Human Gene | Nematode Gene Ortholog | Human Gene | Nematode Gene Ortholog | Human Gene | Nematode Gene Ortholog |
|---|---|---|---|---|---|
| PSEN1 | sel-12 | SOD1 | sod-1 | SMN2 | smn-1 |
| APP | apl-1 | SQSTM1 | sqst-4 | DYNC1H1 | dhc-1 |
| PSEN2 | sel-12 | CHMP2B | C01A2.4 | TRPV4 | osm-9 |
| SORL1 | egg-1 | C9ORF72 | alfa-1 | BICD2 | bicd-1 |
| MAPT | ptl-1 | PON1 | poml-2 | IGHMBP2 | eri-7 |
| IL1B | C44B12.6 | FUS | fust-1 | VRK1 | vrk-1 |
| BACE1 | asp-15 | ANG | — | UBA1 | uba-1 |
| ACE | acn-1 | VCP | cdc-48.1 | ASAH1 | asah-1 |
| TARDBP | tdp-1 | ATXN2 | atx-2 | VAPB | vpr-1 |
| UNC13A | unc-13 | SMN1 | smn-1 | LMNA | lmn-1 |
| LRRK2 | lrk-1, | ZMPSTE24 | fce-1 | LMNA | lmn-1 |
| SNCA | — | RECQL4 | wrn-1 | BLM | him-6 |
| PARK2 | pdr-1 | TP53 | cep-1 | ELK1 | lin-1 |
| PINK1 | pink-1 | MAGI2 | magi-1 | ATP1A3 | eat-6 |
| MAPT | ptl-1 | DISC1 | myo-5 | PTEN | daf-18 |
| GBA | gba-3 | DTNBP1 | dsbn-1 | ERCC6 | csb-1 |
| PARK7 | djr-1.1 | COMT | comt-3 | APP | apl-1 |
| DRD1 | dop-1 | HTR2A | ser-1 | SLC6A3 | dat-1 |
| IGF1R | daf-2 | NRG1 | igeg-1 | CACNA1A | unc-2 |
| MAOB | amx-2 | ATP2A2 | sca-1 | KL | klo-1 |
| WRN | wrn-1 | | | | |

LMNA Gene.

The LMNA gene was chosen because it is a gene contributing to many different diseases, wherein variant groups are known to associated with different diseases. Loss of function in CE ortholog lmn-1 results in a detectable phenotype. Transgenic control animals were created by gene-swap with a chimeric human cDNA. Next transgenic test animals are made as clinical variants installed into the humanized transgenic control strain. Deviant phenotypes observed of the test strains are used to characterized variant pathogenicity, perform drug screen to observe restoration of normal activity, and for discovery of biosensors giving a fluorescent signal when restoration of activity occurs.

Example 7: Control and Test Transgenic Nematodes for Examining Lifespan/Healthspan Pharmacological Interventions as Models of Dementia Frontotemporal Lobe Dementia (FTD) is a neurodegenerative disease characterized by progressive deficits in language, behavior, and executive function resulting from cortical neuron dysfunction and degeneration (Bang J et al. Frontotemporal dementia. Lancet. 2015 Oct. 24; 386 (10004):1672-82). Roughly half of dementia in middle-aged patients is FTD; half is Alzheimer's (Ratnavalli E et al. The prevalence of frontotemporal dementia. Neurology. 2002 Jun. 11; 58(11):1615-21). The genes associated with FTD including MAPT, GRN, C9ORF72, FUS, TARDBP, VCP, CHMP2B, SQSTM1 UBQLN2 and others. Between 10 and 30% of FTD can be ascribed to deleterious dominant alleles in MAPT, GRN, C9ORF72 (Rainero I et al. Recent advances in the molecular genetics of frontotemporal lobar degeneration. Funct Neurol. 2017 January/March; 32(1):7-16; Deleon J et al. Frontotemporal dementia. Handb Clin Neurol. 2018 148:409-430). FTD is often comorbid with ALS, atypical Parkinson's, or other degenerative diseases. In fact, the same alleles that cause FTD can often cause those comorbid diseases, or symptoms of both diseases simultaneously, suggesting that common mechanisms are shared. Because of late onset of FTD and related diseases, accelerated aging is a major factor in disease onset or progression. There is no approved therapy for FTD (Kerchner G et al. Abhorring the vacuum: use of Alzheimer's disease medications in frontotemporal dementia. Expert Rev Neurother. 2011 May; 11(5):709-17); in fact, no effective therapy exists for any late-onset neurodegenerative disorder.

Provided herein are four transgenic nematodes prepared according to Example 1 (wild type humanized nematodes), and clinical variants prepared according to Example 2 and tested in phenotype behavior assays. For model systems exhibiting strong defects in the phenotype behavior assays, test compounds known to extend lifespan/healthspan are examined for a capacity to restore wild type behavior and/or suppress neurodegeneration.

The humanization of the nematodes is carried out with replacement of the nematode ortholog with human MAPT, GRN, C9orf72, and TARDBP gene sequences to create FTD models for screening the efficacy of lifespan/healthspan-extending compounds.

MAPT Gene:

The pd-1 ortholog in C. elegans is replaced with the 4R-containing isoform 2 (NM_005910.5). Replacement sequence for Gene-Swap is a codon-optimized cDNA sequence coding for 441 amino acids with three synthetic introns inserted into the optimized sequence and aberrant splice sites removed. GRN gene: GRN alleles associated with FTD are associated with early stop/frameshift mutations that will reduce GRN function (Mukherjee O et al. HDDD2 is a familial frontotemporal lobar degeneration with ubiquitin-positive, tau-negative inclusions caused by a missense mutation in the signal peptide of progranulin. Ann Neurol. 2006 September; 60(3):314-22; Gass J et al. Mutations in progranulin are a major cause of ubiquitin-positive frontotemporal lobar degeneration. Hum Mol Genet. 2006 Oct. 15; 15(20):2988-3001; van Swieten J and Heutink P. Mutations in progranulin (GRN) within the spectrum of clinical and pathological phenotypes of frontotemporal dementia. Lancet Neurol. 2008 October; 7(10):965-74). The longest length isoform (NP_002078) of 593 amino acids is Gene-Swapped into the pgrn-1 ortholog locus. C9orf72 gene: The molecular lesion associated C9orf72-linked FTD-ALS is associated with increased lengths of GGGGCC hexanucleotide repeats (G4C2) in the C9orf72 first intron (DeJesus-Hernandez M et al. Expanded GGGGCC hexanucleotide repeat in noncoding region of C9ORF72 causes chromosome 9p-linked FTD and ALS. Neuron. 2011 Oct. 20; 72(2):245-56; Renton A et al. A hexanucleotide repeat expansion in C9ORF72 is the cause of chromosome 9p21-linked ALS-FTD. Neuron. 2011 Oct. 20; 72(2):257-68). One G4C2 repeats is inserted into the first intron of C9orf72's alfa-1 ortholog. TARDBP gene: TDP43/TARDBP accumulates into FTD-associated aggregates in pathogenic tissues and mutations in this gene can cause FTD (van Deerlin V et al. TARDBP mutations in amyotrophic lateral sclerosis with TDP-43 neuropathology: a genetic and histopathological analysis. Lancet Neurol. 2008 May; 7(5):409-16; Chen-Plotkin A et al. TAR DNA-binding protein 43 in neurodegenerative disease. Nat Rev Neurol. 2010 April; 6(4):211-20). Isoform 1 at 414 amino acids (NP_031401), the predominant expression product of the TARDBP locus involved in FTD (Harrison 2017), is Gene-Swapped into the tdp-1 ortholog locus. The result is 4 types of humanized transgenic control animals as prepared according to Example 1 (e.g., transgenic control nematode).

A battery of functional phenotype behavior assays, disclosed in detail below, is applied to the transgenic control nematodes to verify rescue of function as a restoration of activity as either intermediate or complete in each assay. When humanized transgenic control nematodes with partial or complete rescue of function are identified, they are then used to install clinical variants in the humanized gene at the native locus of the transgenic nematode.

For each humanized gene, two disease-causing alleles are installed and examined for their impact in phenotyping assays. MAPT gene: The MAPT gene has 408 coding sequence variants of which 26 are possibly pathogenic. For example, the pathogenic clinical variants G272V (Hutton M et al. Association of missense and 5'-splice-site mutations in tau with the inherited dementia FTDP-17. Nature. 1998 Jun. 18; 393(6686):702-5) and P301L (Dumanchin C et al. Segregation of a missense mutation in the microtubule-associated protein tau gene with familial frontotemporal dementia and parkinsonism. Human molecular genetics. (1998); Rizzu P et al. High prevalence of mutations in the microtubule-associated protein tau in a population study of frontotemporal dementia in the Netherlands. Am J Hum Genet. 1999 February; 64(2):414-21) are installed into the MAPT humanized gene. GRN gene: The GRN gene contains 366 molecular variants of which 23 are possibly pathogenic. Two established pathogenic variants, Q125X (Snowden J et al. Progranulin gene mutations associated with frontotemporal dementia and progressive non-fluent aphasia. Brain. 2006 November; 129(Pt 11):3091-102) and R493X (Huey E et al. Characteristics of frontotemporal dementia patients with a Progranulin mutation. Ann Neurol. 2006 September; 60(3):374-80), are installed into the humanized GRN gene. C9orf72 gene: Hexanucleotide repeats [G4C2]36 and [G4C2]60 are inserted into the repeats into the humanized first intron of the C. elegans alfa-1 locus. TARDBP gene: The TARDBP gene has 94 molecular variants of which 21 are possibly pathogenic. Clinical variants G295S (Caroppo P et al. Defining the spectrum of frontotemporal dementias associated with TARDBP mutations. Neurol Genet. 2016 May 26; 2(3)) and A382T (Borghero G et al. A patient carrying a homozygous p.A382T TARDBP missense mutation shows a syndrome including ALS, extrapyramidal symptoms, and FTD. Neurobiol Aging. 2011 December; 32(12):2327) are installed in the humanized TARDBP locus.

Four functional assays and three assays specific to neurodegeneration are deployed to uncover deviant biology. Locomotion defects are assessed with dispersal, swimming, and chemotaxis assays. Neuromuscular defects are assessed using pharynx pumping/electrophysiology (ScreenChip assay system). Neurodegeneration is detected by dye uptake and using neuronal GFP reporter lines. Protein aggregation associated with TDP FTD is detected with a TARDBP::GFP reporter line Locomotion defects of the transgenic nematode system for assessing function of a heterologous gene (transgenic control animals) and the transgenic nematode system for assessing function of a variant heterologous gene (transgenic test animals) are measured using a Dispersal assay, a Swimming locomotion assay and a Food Race assay. For the dispersal assay, animals are placed in the center of a culture dish and spontaneous locomotion is quantified after 1 hour by measuring distance from origin. Uncoordinated/lethargic animals or extremely old animals travel less distance. For the swimming locomotion assay videos of animals swimming in liquid are quantified using CeLEST software (Restif C et al. CeleST: computer vision software for quantitative analysis of C. elegans swim behavior reveals novel features of locomotion. PLoS Comput Biol. 2014 Jul. 17; 10(7): e1003702.); this assay is sensitive to modest perturbations in gait or activity. In each frame, animals are automatically detected, and motion metrics are computationally extracted. The Food Race assay measures speed of chemotaxis towards a food source (Mitchell P et al. A differential role for neuropeptides in acute and chronic adaptive responses to alcohol: behavioral and genetic analysis in Caenorhabditis elegans. PLoS One. 2010 May 3; 5(5):e10422). Animals are placed on one end of plate at a 1 cm distance from edge of food source. At 15, 30, and 60 min timepoints the ratio of animals at food is observed.

Electrical activity (electrophysiology) associated with feeding of transgenic control animals vs transgenic test animals is measured using the ScreenChip system (Nemametrix Inc.).

Neurodegeneration of the clinical variant humanized nematodes as compared to wildtype humanized nematodes is assessed using three assays; dye uptake, GFP reporter lines, and TARDBP aggregation. Dye uptake is used to assess degeneration in glutamatergic sensory neurons in the head and tail of nematodes. A subset of those neurons is sufficiently exposed to the environment for uptake of lipophilic, fluorescent dyes, such as DiD ($C_{67}H_{103}ClN_2O_3S$). Degenerative sensory process retraction or cell death can completely prevent dye uptake for individual neurons (Faber P, Alter J, MacDonald M, Hart A. Polyglutamine-mediated dysfunction and apoptotic death of a Caenorhabditis elegans sensory neuron. Proc Natl Acad Sci USA. 1999 Jan. 5; 96(1):179-84). GFP reporter lines are used to assess neuron death in the nematodes. Transgenic lines expressing GFP in different classes of neurons are readily available in C. elegans and can be used to detect late-onset cell loss in models of neurodegenerative disease. TARDBP aggregation is measured by counting TARDBP-GFP accumulation into puncta/aggregates, similar to the use of fluorescent-tagged polyQ (Lee A et al. A new Caenorhabditis elegans model of human huntingtin 513 aggregation and toxicity in body wall muscles. PLoS One. 2017 Mar. 10; 12(3):e0173644), aggregation propensity of TARDBP (Moreno, F. et al. A novel mutation P112H in the TARDBP gene associated with frontotemporal lobar degeneration without motor neuron disease and abundant neuritic amyloid plaques. Acta Neuropathol Commun. 2015 Apr. 3; 3:19) can be tagged with GFP (Zeineddine R et al. Flow cytometric measurement of the cellular propagation of TDP-43 aggregation. Prion. 2017 May 4; 11(3):195-204) can be used to monitor FTD-associated accumulation (Chou C et al. TDP-43 pathology disrupts nuclear pore complexes and nucleocytoplasmic transport in ALS/FTD. Nat Neurosci. 2018 February; 21(2): 228-239).

The above battery of assays is used to validate and identify pathogenic transgenic nematodes that comprise a clinical variant introduced into a human gene replacing the native locus of the nematode ortholog gene.

Drug Screening:

Lifespan/healthspan-extending compounds are screened on the validated pathogenic clinical variant humanized transgenic nematodes for capacity to slow or reverse dysfunction and/or neurodegeneration in the MAPT, GRN, C9orf72, and TARDBP disease models. The test compounds include aspirin, rapamycin, acarbose, nordihydroguaiaretic acid, protandim, rapamycin, resveratrol, some senolytics, and Thioflavin T. A total of 50 compounds with potential to impact lifespan or healthspan, are tested on the above validated transgenic nematodes. The above validated pathogenic transgenic nematodes comprising a clinical variant of one of MAPT, GRN, C9orf72, and TARDBP are placed in a medium comprising one of the 50 test compounds and incubated from about 30 minutes up to about 72 hours. Following the incubation period, the above battery of phenotypic and functional assays is performed to determine any compounds that positively impact phenotype as compared to control (with no test compound) and/or as compared to wild type humanized transgenic nematodes.

Example 8: Control and Test Transgenic Nematodes as Humanized Animal Model Systems for Assessing Clinical Variant Pathogenicity of Ion Channels Three human genes (SLC6A4, CACNA1A and ATP1A3) are selected as representatives of ion channelopathy targets. Wildtype humanized transgenic nematodes are prepared according to Example 1 to create transgenic control animals. Specifically, the human sequence for the disease gene optimized for expression capacity and swapped in as gene replacement of the native locus of the nematode replacing the nematode ortholog. For each human gene inserted, a set of derivative lines is made; 15 variant lines are made with 5 known pathogenic variants, 5 to benign variants, and 5 variants of uncertain significance (VUS) alleles using CRISPR mediated site-directed mutagenesis insert clinical variants into the gene-swapped locus. Insertion of amino acid changes is done via an oligo-mediated repair process as described in the co-CRISPR technique.

Known pathogenic and benign variants are used as controls and to validate the functional system. Variants of uncertain significance (VUS) are installed to determine if they exhibit pathogenic or benign activity profiles. For the prerequisite conditions, if a strong knockout phenotype is detected, a humanized rescue construct is created and tested for capacity to restore normal function. The phenotypic consequence of the installed variants is quantified using various phenotyping assays.

As disclosed in Example 1, CRISPR transgenesis is used to humanize a native locus via gene-swap replacement into the native locus of C. elegans animal model. The first gene, SLC6A4, is a target of selective serotonin inhibitors and has a defined role in mediating depression (Zhu J et al. Serotonin Transporter Gene Polymorphisms and Selective Serotonin Reuptake Inhibitor Tolerability: Review of Pharmacogenetic Evidence. Pharmacotherapy. 2017 Jun. 27.), bipolar disorder (Sugawara H et al. Hypermethylation of serotonin transporter gene in bipolar disorder detected by epigenome analysis of discordant monozygotic twins. Transl Psychiatry. 2011 Jul. 26; 1:e24.), and schizophrenia (Peitl V et al. Depressive symptoms in schizophrenia and dopamine and serotonin gene polymorphisms. Prog Neuropsychopharmacol Biol Psychiatry. 2017 Jul. 3; 77:209-215.). The SLC6A4 cDNA is inserted as a gene swap replacement of mod-5 ortholog locus (65% sequence similarity). The next gene, CACNA1A, is associated with neurological disease of ataxia (Giunti P et al. Molecular mechanism of Spinocerebellar Ataxia type 6: glutamine repeat disorder, channelopathy and transcriptional dysregulation. The multifaceted aspects of a single mutation. Front Cell Neurosci. 2015 Feb. 16; 9:36.) and epilepsy (Prontera P et al. Epilepsy in hemiplegic migraine: Genetic mutations and clinical implications. Cephalalgia. 2017 Januray 1:333102416686347.). The CACNA1A cDNA is inserted as a gene swap of unc-2 ortholog locus (52% sequence similarity). The ATP1A3 gene is associated with rapid-onset dystonia-parkinsonism (Brashear A et al. ATP1A3-Related Neurologic Disorders. GeneReviews—National Center for Biotechnology Information. Feb. 22, 2018), ataxia (Schirinzi T et al. Childhood Rapid-Onset Ataxia: Expanding the Phenotypic Spectrum of ATP1A3 Mutations. Cerebellum. 2018 Feb. 3.), alternating hemiplegia (Pavlidis E et al. Alternating hemiplegia of childhood and a pathogenic variant of ATP1A3: a case report and pathophysiological considerations. Epileptic Disord. 2017 Jun. 1; 19(2):226-230.), and CAOS-Episodic Cerebellar Ataxia (25895915). The ATP1A3 cDNA is inserted as a gene swap of the eat-6 locus (84% sequence similarity). In all three cases, the human sequence of the disease gene replaces a native nematode ortholog gene locus by CRISPR-based gene swap insertion. Finally, the capacity to rescue function is measured in a set of three phenotyping assays, such as the Food Race assay.

Validated wild type humanized transgenic nematodes are used to install clinical variants (benign and pathogenic) and variants of uncertain significance (VUS). As disclosed above, 15 variant lines are made comprising 5 to known pathogenic variants, 5 to benign variants and 5 to Variants of uncertain significance (VUS). The five known pathogenic variants and five benign variants serve as controls in the phenotyping screening assays. The variants are validated in phenotypic screening assays, such as food race and ScreenChip, (e.g., pathogenic variants demonstrate loss of function as compared to wildtype and benign demonstrate comparable function to wild type). Next, variants of uncertain significance (VUS) are screening in the phenotypic assays and compared to the pathogenic variants, benign variants and wildtype. This example uses humanized animal models as a biologically relevant system for rapid phenotype profiling of clinical variants of uncertain function.

Hence, provided herein is a transgenic nematode system for assessing function, or characterizing a VUS, of a variant heterologous gene and methods of use. The transgenic nematode system comprises a host nematode comprising a heterologous gene optimized for expression in the host nematode wherein the heterologous gene replaced a host nematode gene ortholog and the heterologous gene rescues function of the replaced nematode ortholog. In that instance the host transgenic nematode comprises a wildtype heterologous gene. Also provided herein is a transgenic nematode system comprising variant heterologous gene wherein the expressed heterologous gene comprises one or more amino acid changes providing a variant of the heterologous gene. The variants may be classified as pathogenic, likely pathogenic, benign, likely benign or a variant of unknown significance. Further provided herein is a method for characterizing the variants of unknown significance comprising performing a phenotypic screen to identify a phenotype of the test transgenic nematode, wherein a change in phenotype as compared to a control transgenic nematode comprising a wildtype heterologous gene indicates an altered function of the clinical variant in the test transgenic nematode.

Example 9: Assessing the Function of the Human CACNB4 Gene and Clinical Variants in a Transgenic Nematode The human cDNA for CACNB4 (Calcium Voltage-Gated Channel Auxiliary Subunit Beta 4; a protein implicated in epilepsy) was substituted into the ccb-1 ortholog locus in C. elegans using the gene-swap humanization method. CACNB4/ccb-1-sequence identity is 63% and sequence similarity is 78%. (Hu et al., BMC Bioinformatics. 2011 Aug. 12:357).

The human CACNB4 (hCACNB4) cDNA sequence was optimized for expression in the host nematode (*C. elegans*) via codon optimization, addition of modified host intron sequences and variant splice site determination as detailed in Example 1. In the instance of CACNB4 the following expression-optimized cDNA sequence with introns (lower case) was used (SEQ ID NO: 45):

ATGTCCTCCTCCTCCTACGCCAAGAACGGAACCGCCGACGGACCACAC
TCCCCAACCTCCCAAGTCGCCCGTGGAACCACCACCCGTCGTTCCCGTCT
CAAGCGTTCCGACGGATCCACCACCTCCACCTCCTTCATCCTCCGTCAAG
GATCCGCCGACTCCTACACCTCCCGTCCATCCGACTCCGACGTCTCCCTC
GAGGAGGACCGTGAGGCCATCCGTCAAGAGCGTGAGCAACAAGCCGCCAT
CCAACTCGAGCGTGCCAAGTCCAAGCCAGTCGCCTTCGCCGTCAAGACCA
ACGTCTCCTACTGCGGAGCCCTCGACGAGGACGTCCCAGTCCCATCCACC
GCCATCTCCTTCGACGCCAAGGACTTCCTCCACATCAAGgtgagtgattt
taaacattatctgtacttaaattataaattctctattcagGAAAAATACA
ACAACGACTGGTGGATCGGACGTCTCGTCAAGGAGGGATGCGAGATCGGA
TTCATCCCATCCCCACTCCGTCTCGAGAACATCCGTATCCAACAAGAGCA
AAAGCGTGGACGTTTCCACGGAGGAAAGTCCTCCGGAAACTCCTCCTCCT
CCCTCGGAGAGATGGTCTCCGGAACCTTCCGTGCCACCCCAACCTCCACC
GCCAAGCAAAAGCAAAAGGTCACCGAGCACATCCCACCATACGACGTCGT
CCCATCCATGCGTCCAGTCGTCCTCGTCGGACCATCCCTCAAGGGATACG
AGGTCACCGACATGATGCAAAAGgtaaataattatacattcgatgataaa
tttatgcgtactattttcagGCCCTCTTCGACTTCCTCAAGCACCGTTT
CGACGGACGTATCTCCATCACCCGTGTCACCGCCGACATCTCCCTCGCCA
AGCGTTCCGTCCTCAACAACCCATCCAAGCGTGCCATCATCGAGCGTTCC
AACACCCGTTCCTCCCTCGCCGAGGTCCAATCCGAGATCGAGCGTATCTT
CGAGCTCGCCCGTTCCCTCCAACTCGTCGTCCTCGACGCCGACACCATCA
ACCACCCAGCCCAACTCATCAAGACCTCCCTCGCCCCAATCATCGTCCAT
GTCAAAGTCTCCTCCCCAAAGgttaaatgtacaaacaactatttgaaaga
ttactcacccgattattcagGTCCTCCAACGTCTCATCAAGTCAAGAGGT
AAGTCCCAGTCAAAACACCTCAACGTCCAGCTGGTCGCCGCAGATAAATT
AGCCCAATGCCCACCAGAGATGTTCGACGTCATCCTCGACGAGAACCAAC
TCGAGGACGCCTGCGAGCACCTCGGAGAGTACCTCGAGGCCTACTGGCGT
GCCACCCACACCACCTCCTCCACCCCAATGACCCCACTCCTCGGACGTAA
CCTCGGATCCACCGCCCTCTCCCCATACCCAACCGCCATCTCCGGACTCC
AATCCCAACGTATGCGTCACTCCAACCACTCCACCGAGAACTCCCCAATC
GAGCGTCGTTCCCTCATGACCTCCGACGAGAACTACCACAACGAGCGTGC
CCGTAAGTCCCGTAACCGTCTCTCCTCCTCCTCCCAACACTCCCGTGACC
ACTACCCACTCGTCGAGGAGGACTACCCAGACTCCTACCAAGACACCTAC
AAGCCACACCGTAACCGTGGATCCCCAGGAGGATACTCCCACGACTCCCG
TCACCGTCTCTAA Artificial host intron sequences used in this construct include SEQ ID NO 46:
gtaaataattatacattcgatgataaatttatgcgtactattttcag
and SEQ ID NO: 47
gttaaatgtacaaacaactatttgaaagatttctcacccgattttttcag The optimized hCACNB4 cDNA sequence was obtained as a gene block from IDTDNA, Inc. It was cloned into an intermediate plasmid (pNU1891) which contained the homology arms and Hygromycin resistance cassette using Gibson assembly (Gibson et al. Enzymatic assembly of DNA molecules up to several hundred kilobases 2009 *Nat. Methods* May; 6(5):343-5). The intermediate plasmid (pNU1891) was made in a 5-step process following the protocol of Example 1, with appropriate selection of primer and sgRNA cut site sequences.

Part 1 is the plasmid backbone. Parts 2 and 5 are homology arms amplified from N2 wild-type genomic DNA. The left homology arm was 1548 bp and contains the ccb-1 promoter. This was designed so the plasmid would allow for expression of hCACNB4 as an array if the gene swap transgenic was unable to be isolated. The left homology arm has perfect homology for the sgRNA cut site of CTGCGGAAAGCCATCTAGCG SEQ ID NO: 45 which will allow for insertion of hCACNB4 after the starting Methionine in ccb-1. The right homology arm has perfect homology for the sgRNA cut site of ATGTCACATCAATATGAAAG SEQ ID NO: 46 which is in the last exon of ccb-1. Part 3 for the intermediate is the eft-3 3'UTR. eft-3 is the translation elongation factor 1-alpha homolog in *C. elegans* and is a highly expressed gene. In this construct the eft-3 3'UTR is used instead of the native ccb-1 3'UTR. Part 4 is a hygromycin B Resistance (hygR) cassette PCR amplified from pNU1298. The hygR cassette is 2368 bp and contains the rps-8 promoter, hygromycin B phosphotransferase gene, and the tbb-2 3'UTR. When the hygromycin B resistance gene is expressed in transgenic *C. elegans* animals are able to survive Hygromycin B treatment while non-transgenic *C. elegans* animals are not able to survive (Radman I, Greiss S, Chin J W. Efficient and rapid *C. elegans* transgenesis by bombardment and hygromycin B selection. PLoS One. 2013 Oct. 9; 8(10):e76019).

The intermediate plasmid (pNU1891) is assembled from the 5 parts using the Gibson assembly technique. The hCACNB4 codon optimized sequence was provided as a GeneBlock from IDTDNA, Inc and the sequence inserted using Gibson assembly in frame after the left homology arm and before the eft-3 3'UTR of the intermediate plasmid. The final plasmid (pNU1892) was confirmed by sequencing.

Following insertion of the optimized cDNA hCACNB4 sequence in a plasmid for homologous recombination with the host nematode ortholog, a transgenesis mixture containing (pNU1892 (hCACNB4 donor homology plasmid), sgRNA plasmid pNU1889 (targeting CTGCGGAAAGCCATCTAGCG site (SEQ ID NO: 48)), sgRNA plasmid pNU1890 (targeting ATGTCACATCAATATGAAAG site (SEQ ID NO: 49)), pNU1027 (Cas9 expressing) was injected into gonads of the host *C. elegans* using standard microinjection techniques, using protocols detailed in Example 1, animals propagated and founders identified. After populations were established, a series of PCR tests were applied to the founder individual (NMX18) to identify a strain as confirmed for desired transgenesis. Integration of the inserted sequence is confirmed by PCR from the inserted sequence, across the left and right homology arms, and into the native genome. A PCR tests was also performed to detect extrachromosomal arrays and the wild-type sequence and it was found that the NMX18 founder did not contain extrachromosomal arrays or the wild-type sequence, and instead was found confirmed for contain the desired integration into the genome.

Figure 6B:
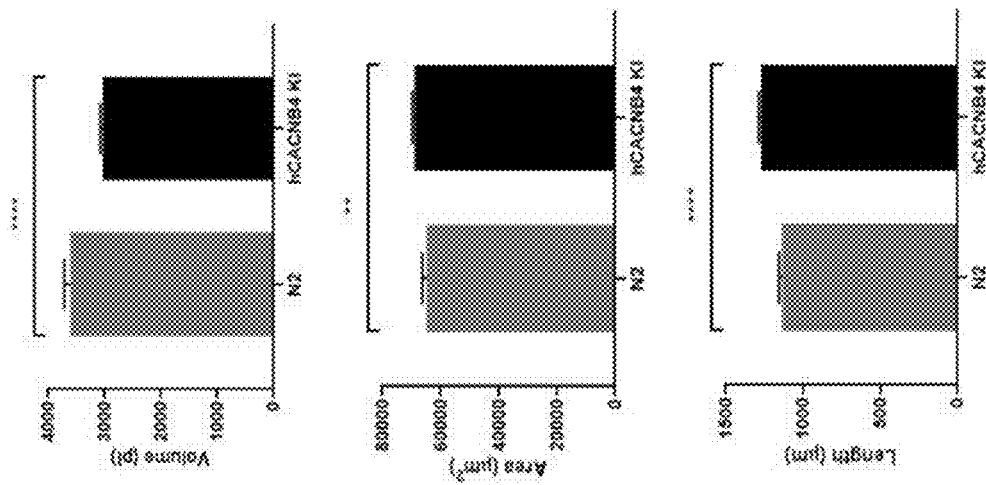
FIG. 6B shows the phenotypic behavior assay (ScreenChip) used to observe the behavior phenotype of transgenic test nematodes hCACNB4 as compared to non-transgenic nematodes (N2).
Figure 6A:
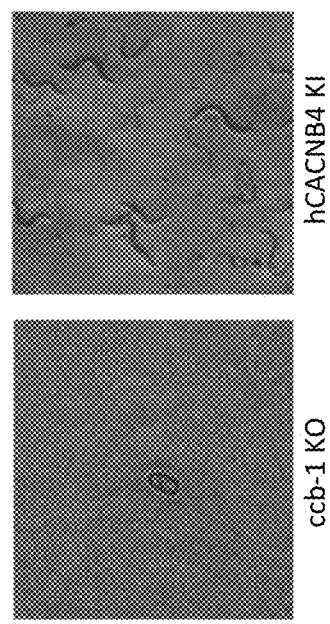
FIG. 6A shows nematodes that are homozygous for the ccb-1 deletion arrest during embryonic development and do not develop to adulthood (left panel), while insertion of human CACNB4 into the ccb-1 was used demonstrated reverse of lethality (right panel).

Phenotypic assays were used to validate the transgenic control nematode (e.g. containing and expressing the hCACNB4 gene) using N2 (wild type worms) and KO (e.g. the nematode ortholog, ccb-1) as controls. Phenotypic characterization and comparison to N2 and the ccb-1 KO (VC37) were performed. Animals that are homozygous for the ccb-1 deletion arrest during embryonic development and do not develop to adulthood. Insertion of human CACNB4 into the ccb-1 was used to test for reverse of lethality. See FIG. 6A. Some phenotypic differences were observed between wild-type (N2) and hCACNB4 individuals. hCACNB4 worms pumped at a slower rate, with longer pumps and a longer interval between pumps. See FIG. 6B. This was measured using the ScreenChip System (NemaMetrix, Inc) on synchronized worm populations. Electrophysiological data for pharyngeal pump frequency, pump duration and pump interval were obtained for 84-204 worms of all genotypes using the ScreenChip system over 4-7 experimental days. First-day adults were incubated in 10 mM 5HT for 20 minutes prior to EPG recordings commencing. Experiments were conducted between 21-23° C. Data were analyzed using NemAnalysis v. 1485, 1588, 1649 and 1662. These different versions represent in-house changes to imaging features within the NemAnalysis software suite and not the EPG analysis algorithm. Statistical tests were conducted on the mean pumping frequency (Hz), mean inter-pump duration (ms) and mean inter-pump interval (ms) for each strain, calculated from the mean value obtained for each worm. Prior to statistical analysis, D'Agostino-Pearson omnibus normality tests were used to test whether data had a Gaussian distribution. The comparison between the mean pumping duration of hCACNB4 and N2 worms was made with a two-tailed t-test following a Y=1/Y transformation. Remaining EPG data were non-normal and could not be transformed; consequently, statistical comparisons were conducted using a two-tailed Mann-Whitney U test. All statistical tests for this phase of the experiment were conducted using GraphPad Prism v. 7.04. Other options for analyzing data may include use of stepwise-regression models to control for confounding factors.

Figure 6D:
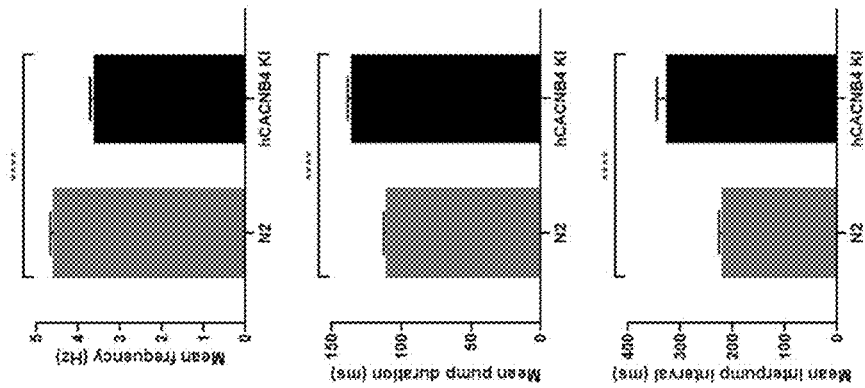
FIG. 6D shows physical measurement of the N2 wildtype and hCACNB4 nematodes, wherein N2 worms were larger in volume but had less surface area and were shorter than hCACNB4 strain. This indicates that N2 worms were stockier and had a larger diameter, while hCACNB4 worms were thinner and more elongated.
Figure 6C:
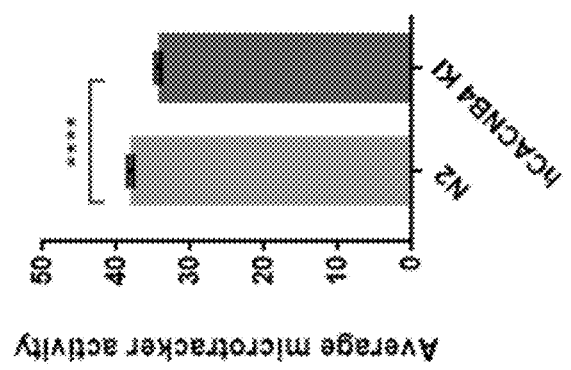
FIG. 6C shows the phenotypic behavior assay (WMicrotracker) used to observe population-level locomotory activity, wherein the hCACNB4 strain exhibited a substantial decrease in motility when compared to N2 worms.

The hCACNB4 strain also exhibited a substantial decrease in motility when compared to N2 worms. See FIG. 6C. Population-level locomotory activity was observed using a WMicrotracker device (Phylumtech, S.A.). The WMicrotracker quantifies activity by observing interruptions in an infrared beam over an hour of observation. We used 30-70 animals per well and ran 4-8 wells for each strain tested on each day. Each strain was assayed on four separate days. On each experimental day, the total number of animals assayed per strain ranged from 350-700. Paired data were collected for N2 animals and hCACNB4 KI (NMX18). Average movement data were tested for normality using a D'Agostino-Pearson omnibus normality test and analyzed using a one-way ANOVA with a Dunnett's multiple comparison post-hoc test.

N2 worms were larger in volume but had less surface area and were shorter than hCACNB4 strain. See FIG. 6D. This indicates that N2 worms were stockier and had a larger diameter, while hCACNB4 worms were thinner and more elongated. Synchronized video recordings were captured using in conjunction with ScreenChip data, enabling a visual examination of pumping behavior. We used an automated algorithm, NemaSize (NemaMetrix, Inc.), to analyze worm area, size and volume. Briefly, the algorithm uses a series of standard image analysis packages to normalize and smooth the worm, a transform to enhance the contrast at the edges, and a skeletonization to find the length of the worm. The skeleton is then used to refine the contour to compute area, and the channel dimensions and contour are used to compute volume. Statistical tests were conducted on size parameters calculated for a subset of first-day adult individuals from each genotype over 5-8 experimental days. Prior to statistical analysis, D'Agostino-Pearson omnibus normality tests were used to test whether data had a Gaussian distribution. Differences in volume, area and length between hCACNB4 and N2 animals were subsequently calculated using either a two-tailed t or two-tailed Mann-Whitney U test.

Because a significant phenotypic difference occurred between the humanized worm (Transgenic Control Nematode) and the knockout, clinical variants were installed into the hCACNB4 locus to generate Transgenic Test Nematodes. The hCACNB4 line was modified by the introduction of amino acid changes to reflect patient alleles. The three that were completed are C104F, Q204Kfs, and HYP484R where the amino acids H484, Y485, and P486 were deleted and an R inserted. Additionally, we created a M219V variant which is thought to be a benign mutation in hCACNB4. For the amino acids were swap into the hCACNB4 locus, the co-CRISPR method as detailed in Example 2 was used to make transgenics. The specific donor homology and sgRNA sites are listed in the following table.

TABLE 6 hCACNB4 variant construction details

| variant | Donor homology ODN | sgRNA |
|---|---|---|
| C104F | CCAGTCGCCTTCGCCGTCAAG ACCAACGTCTCCTATTTCGGC GCTCTTGACGAGGACGTCCCA GTCCCATCCACCGCCATCTCC SEQ ID NO: 50 | AAGACCAACGTCTCCTACTG SEQ ID NO: 51 CTACTGCGGAGCCCTCGACG SEQ ID NO: 52 |
| Q204Kfs (deletion of g nucleotide resulting in KKstop amino acid sequence change) | CGGAGAGATGGTCTCCGGAAC CTTCCGTGCCACCCCGACTTCT ACTGCTAAACAGAAGAAAAA GTAACGGAGTACATTCCTCCT TACGACGTCGTCCCATCCATG CGTCCAGTCGTCCT SEQ ID NO: 53 | CTTGGCGGTGGAGGTTGGGG SEQ ID NO: 54 GATGGGACGACGTCGTATGG SEQ ID NO: 55 |

TABLE 6-continued hCACNB4 variant construction details

| variant | Donor homology ODN | sgRNA |
| --- | --- | --- |
| M219V | AGCAAAAGCAAAAGGTCACC GAGCACATCCCACCATATGAT GTTGTTCCTTCTGTCCGCCCTG TTGTTCTTGTTGGACCATCCCT CAAGGGATACGAGGTCACCG ACA SEQ ID NO: 56 | CCTTGAGGGATGGTCCGACG SEQ ID NO: 57 |
| HYP484R | CCGTAAGTCCCGTAACCGTCT CTCCTCCTCCTCCCAGCATTCT CGCGATCGTCTAGTTGAGGAG GACTACCCAGACTCCTACCAA GACACCTAC SEQ ID NO: 58 | GTGGTCACGGGAGTGTTGGG SEQ ID NO: 59 CCACTACCCACTCGTCGAGG SEQ ID NO: 60 |

Figure 7A:
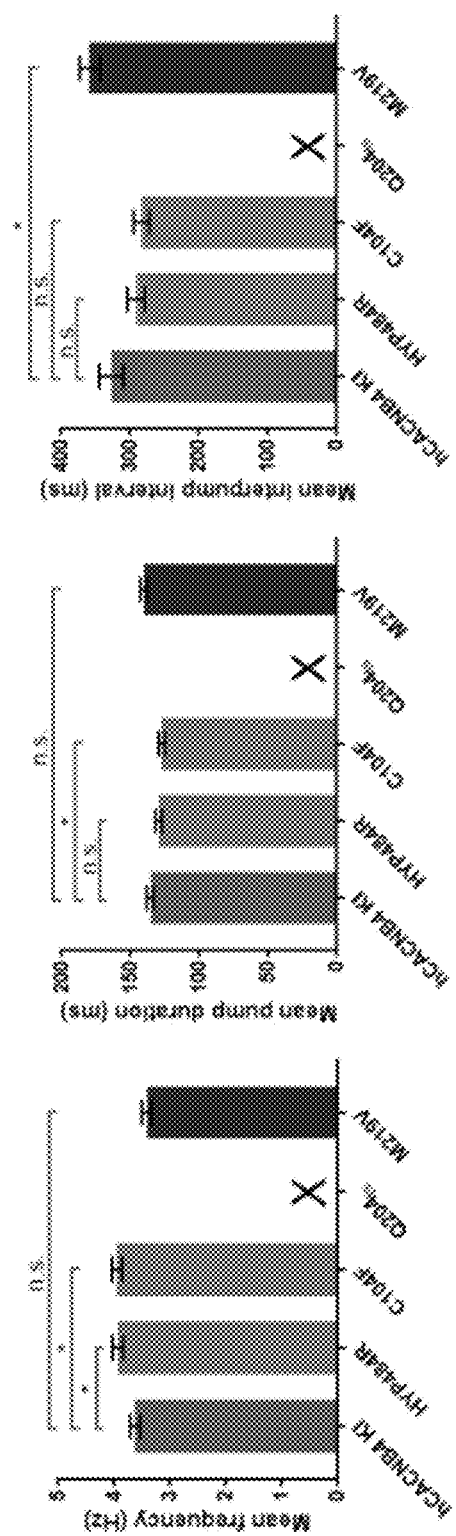
FIG. 7A shows the phenotypic behavior assay (ScreenChip) used to obverse behavior phenotype profile of clinical variants of hCACNB4 (HYP484R, Q204Kfs, C104F, and M219V), wherein the Q204Kfs variant was lethal and no homozygous animals could be generated, the HYP484R and C104F variants exhibited a significantly increased pumping frequency relative to the humanized CACNB4 wild-type, and M219V exhibited a different pattern; there was no increase in pumping frequency relative to the humanized CACNB4 wild-type.
Figure 7B:
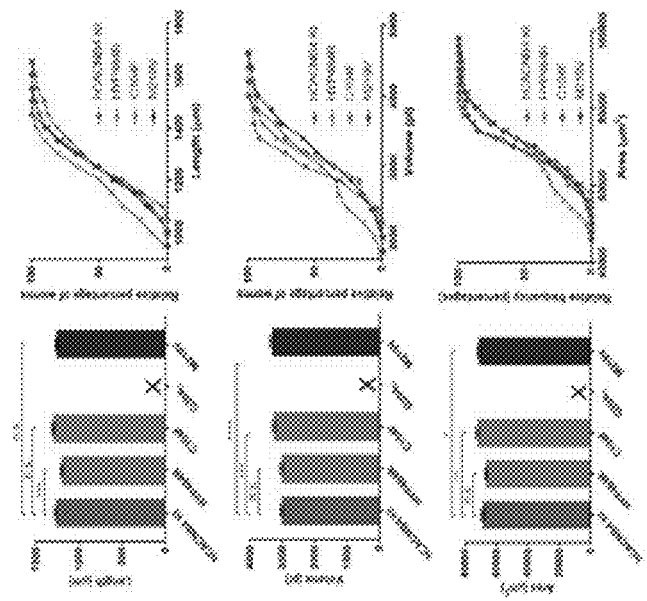
FIG. 7B shows cumulative frequency plots from the ScreenChip phenotypic assay, which revealed distinct behaviors in the relative percentage of worms at different pumping frequencies.
Figure 7C:
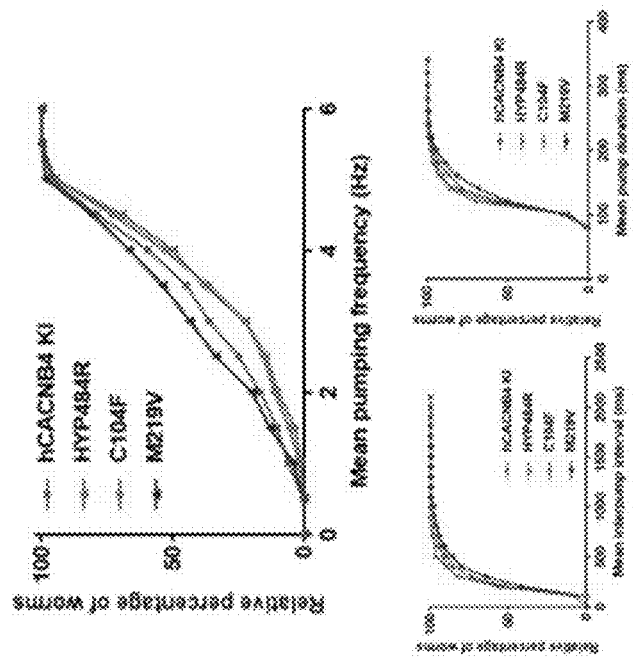
FIG. 7C shows physical measurements of the transgenic control nematode (hCACNB4) as compared to the clinical variants (transgenic test nematodes), wherein the HYP484R variant was significantly shorter than hCACNB4, while C104F and M219V were larger in both volume and area.

After creation and confirmation by sequencing, a phenotypic profile for each line was created by measuring the electrophysiology and size as detailed above. The Q204Kfs variant was lethal and no homozygous animals could be generated. The HYP484R and C104F variants exhibited a significantly increased pumping frequency relative to the humanized CACNB4 wild-type. See FIG. 7A. M219V exhibited a different pattern; there was no increase in pumping frequency relative to the humanized CACNB4 wild-type. Cumulative frequency plots revealed distinct behaviors in the relative percentage of worms at different pumping frequencies. See FIG. 7B. The HYP484R variant was significantly shorter than hCACNB4, while C104F and M219V were larger in both volume and area. See FIG. 7C. These phenotypic characterizations led us to conclude that the C104F, Q204Kfs, and HYP484R variants are pathogenic while the M219V variant is benign.

Example 10: Assessing the Function of the Human KCNQ2 Gene and Clinical Variants in a Transgenic Nematode The human cDNA for KCNQ2 was substituted into the kqt-1 ortholog locus. 5 configurations of human coding sequence were tested (See Table 7). By way of example, nucleotide sequence coding for the pNU1949 was used.

```
SEQ ID NO: 61:
ATGGTACAAAAGTCCAGAAATGGTGGAGTTTACCCGGGTCCATCTGGTGA

AAAAAAATTGAAAGTAGGATTTGTCGGCCTCGACCCTGGAGCGCCGGACA

GTACCAGAGATGGCGCGCTGTTGATCGCTGGTTCGGAGGCACCGAAACGA

GGAAGTATTCTCAGTAAGCCTCGTGCGGGAGGTGCCGGCGCTGGAAAACC

GCCTAAAAGAAATGCCTTTTACAGAAAGCTGCAGAACTTCTTGTATAATG

TGCTGGAACGACCGAGAGGCTGGGCATTTATTTATCACGCCTACGTTTTC

TTGCTTGTTTTCTCCTGCCTTGTGTTGAGTGTTTTCTCCACCATAAAGA

ATACGAAAAAGTTCCGAGGGTGCTCTTTACATCCTCGAAATTGTCACCA

TCGTGGTGTTCGGAGTGGAATACTTTGTTAGAATTTGGGCCGCTGGCTGC

TGCTGCCGATACCGAGGCTGGCGAGGTCGTCTGAAATTTGCTCGAAAACC

GTTCTGTGTCATCGACATTATGGTTCTGATCGCAAGTATTGCTGTCTTGG

CGGCGGGATCTCAGGGCAATGTGTTTGCAACCTCGGCCCTTAGATCCCTC
```

-continued
```
CGATTTTTACAAATCCTCCGTATGATCCGTATGGACCGACGTGGTGGAAC

TTGGAAACTTCTTGGATCCGTCGTCTACGCCCACTCCAAGgtgagtgatt ttaaacattatctgtacttaaattataaattctctattcagGAACTCGTC

ACCGCCTGGTACATCGGATTCTTGTGTCTTATCCTGGCATCGTTTCTTGT

TTACTTGGCCGAAAAGGGTGAAAACGATCACTTTGACACATATGCCGATG

CGTTGTGGTGGGCTTGATCACTCTTACGACAATTGGATATGGTGACAAG

TATCCGCAGACATGGAATGGTAGACTTCTTGCTGCCACCTTCACCCTGAT

CGGTGTCAGTTTCTTCGCCCTCCCAGCTGGCATCCTGGGCTCAGGTTTTG

CGCTGAAGGTCCAAGAGCAGCACCGACAAAAACACTTTGAAAAGCGACGT

AACCCTGCCGCTGGTTTGATTCAATCCGCTTGGAGATTCTACGCTACGAA

CTTGTCTCGTACCGATCTGCACTCTACCTGGCAATACTACGAAAGAACGG

TAACAGTGCCGATGTATTCGTCCCAAACTCAAACTTACGGAGCTTCAAGA

CTGATTCCACCGCTGAACCAGCTGGAGCTGTTGCGAAACCTTAAATCAAA

ATCTGGCCTGGCTTTCCGAAAGGATCCTCCTCCGGAGCCTTCGCCTTCTA

AGGGAAGTCCTTGCAGAGGCCCGCTTTGCGGTTGCTGCCCAGGACGTTCC

TCCCAAAAGgtaaataattatacattcgatgataaatttatgcgtactat ttttcagGTCTCCCTCAAGGACCGTGTCTTCTCCTCCCCGAGAGGCGTAG

CAGCCAAGGGAAAGGGAAGTCCACAAGCACAAACTGTTCGAAGATCGCCT

TCAGCGGACCAATCATTGGAAGACTCGCCATCAAAGGTGCCTAAATCCTG

GTCCTTTGGTGACCGTTCGAGAGCAAGACAGGCCTTCCGTATCAAGGGTG

CGGCATCTCGACAGAATTCGGAAGAAGCTTCACTCCCAGGCGAGGACATC

GTGGACGACAAATCTTGTCCGTGTGAATTTGTGACCGAAGACCTCACTCC

GGGTTTGAAAGTGTCTATCAGAGCGGTGTGCGTGATGAGATTCCTCGTCT

CCAAGCGTAAATTCAAGGAATCCTTGCGACCGTATGACGTTATGGACGTT

ATCGAACAATACTCAGCTGGACATTTGGATATGCTTTCGCGTATCAAGTC

CCTCCAAAGTAGAGTGGACCAAATTGTTGGCAGAGGACCTGCAATCACCG

ACAAGGACAGAACGAAGGGTCCTGCGGAAGCCGAGCTGCCTGAGGACCCA

TCAATGATGGGTAGATTGGGCAAGGTTGAAAAACAAGTTTTGAGTATGGA

GAAGAAACTGGACTTTCTTGTCAATATCTATATGCAAAGAATGGGAATCC
```

-continued
CTCCTACGGAGACCGAGGCCTACTTCGGAGCCAAGgttaaatgtacaaac aactatttgaaagattttctcacccgattttttcagGAGCCCGAGCCAGC

CCCTCCATACCACTCACCAGAAGACTCACGTGAACACGTTGACAGACACG

GTTGCATTGTGAAAATTGTTCGTTCTTCGTCCTCGACGGGTCAGAAAAAC

TTCTCAGCACCACCTGCTGCCCCTCCTGTCCAATGCCCTCCGTCAACTAG

TTGGCAACCGCAAAGTCATCCGCGTCAGGGCCATGGTACGAGTCCAGTAG

GCGATCACGGCTCGTTGGTGCGAATCCCGCCTCCTCCTGCCCACGAGAGA

TCATTGTCTGCCTACGGTGGCGGCAATCGAGCATCTATGGAGTTCCTGAG

ACAAGAAGACACCCCAGGATGCAGACCGCCAGAGGGTAACCTTCGTGACT

CTGACACGTCCATTTCAATCCCTTCAGTTGACCACGAAGAACTCGAGAGA

TCCTTCAGTGGATTTTCCATCTCTCAATCTAAAGAAAATCTGGATGCCCT

CAACTCATGTTATGCGGCGGTCGCACCGTGTGCAAAGGTTCGTCCTTACA

TCGCGGAGGGAGAGAGTGACACAGACAGTGACCTGTGCACGCCTTGCGGA

CCGCCGCCACGATCAGCTACCGGAGAAGGCCCTTTCGGTGATGTGGGATG

GGCAGGCCCTCGAAAATAA

TABLE 7

Plasmids made with synthetic hKCNQ2 inserts.

| | synthetic size | introns | CAI | Transgenic made |
|---|---|---|---|---|
| pNU1909 | 6905 | 4 | 0.9 | |
| pNU1949 | 2778 | 4 | 0.27 | yes |
| pNU1950 | 2727 | 3 | 0.28 | yes |

TABLE 7-continued

Plasmids made with synthetic hKCNQ2 inserts.

| | synthetic size | introns | CAI | Transgenic made |
|---|---|---|---|---|
| pNU1911 | 2718 | 2 | 0.6 | yes |
| pNU1921 | 2433 | 4 | 0.6 | |

The construction of all KCNQ2 strains was similar to the detail provided for CACNB4 in Example 9. In brief, synthetic DNA sequence was obtained from synthetic supplier with eft-3 3' UTR sequence, which was spliced to a downstream selection marker (hygR) and then flanked up and downstream by flanking donor homology arms with final assembly into plasmid backbone. CRISPR-mediated transgenesis was performed to insert the plasmid sequence containing the synthetic DNA as a gene replacement of the nematodes orthologous kqt-1 gene sequence. Candidate transgenics isolated by selection marker were homozygosed and verified by PCR/DNA-sequencing.

Figure 8A:
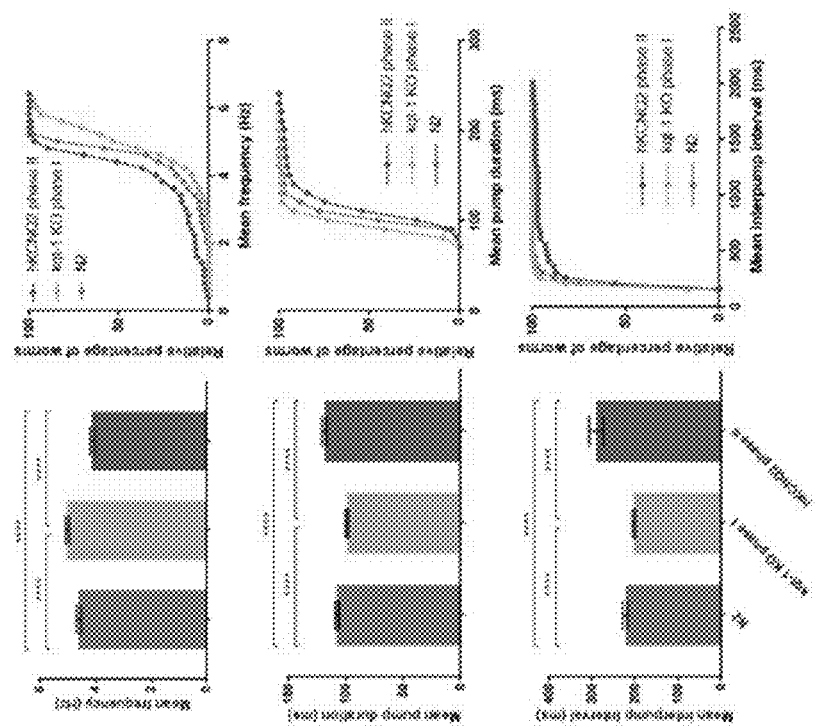
FIG. 8A shows the phenotypic behavior assay (ScreenChip) used to obverse behavior phenotype profile for N2 wild type nematodes, kqt-1 knock-out (KO) nematodes and hKCNQ2 installed into the kqt-1 native locus of the nematode to determine rescue capacity of the human ortholog to provide a validated transgenic control nematode. The kqt-1 KO worms pumped significantly faster than wildtype (N2) individuals, with a significantly shorter mean pump duration and inter-pump interval. The hKCNQ2 knock-in reversed the KO phenotype. The hKCNQ2 KI worms pumped less frequently than kqt-1 KO and N2 individuals.
Figure 8B:
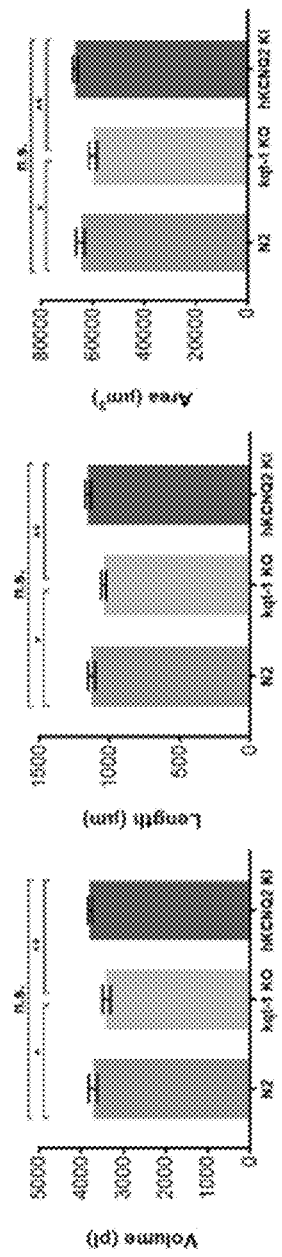
FIG. 8B shows physical measurements of the N2 wild type nematodes, kqt-1 knock out nematodes and the transgenic nematode comprising hKCNQ2, wherein the hKCNQ2 knock-in reversed the KO phenotype, bringing the size back to wildtype levels.

Phenotypic characterization and comparison to N2 and the kqt-1 KO (NMX6 and NMX7) were performed. Phenotypic measurement of rescue capacity involved use of the ScreenChip and NemaSize assays, which can detect deviant phenotypes in kqt-1 knockout strains. The kqt-1 KO worms pumped significantly faster than wildtype (N2) individuals, with a significantly shorter mean pump duration and interpump interval. See FIG. 8A. The hKCNQ2 knock-in reversed the KO phenotype. The hKCNQ2 KI worms pumped significantly slower than kqt-1 KO and N2 individuals. See FIG. 8A. The kqt-1 KO showed a modest, yet significant reduction in overall size. See FIG. 8B. The hKCNQ2 knock-in reversed the KO phenotype, bringing the size back to wildtype levels.

Variant installs as per Table 8, were done by performing CRISPR-base site directed mutagenesis in the humanized line (strain NMX21). All variants were verified by PCR/DNA-sequencing.

TABLE 8 hKCNQ2 variant construction details

| variant | Donor homology ODN | sgRNA |
|---|---|---|
| R198Q | GGCGGGATCTCAGGGCAATGT GTTTGCAACCTCGGCTCTCCA ATCTCTTCGTTTCCTCCAGATT CTTCGTATGATCCGTATGGAC CGACGTGGTGGAACTTGGA (SEQ ID NO: 62) | TCGGAGGGATCTAAGGGCCG (SEQ ID NO: 63) GGTCCATACGGATCATACGG (SEQ ID NO: 64) |
| R201C | GGCGGGATCTCAGGGCAATGT GTTTGCAACCTCGGCTCTCCG TTCTCTTTGCTTCCTCCAGATT CTTCGTATGATCCGTATGGAC CGACGTGGTGGAACTTGGA (SEQ ID NO: 65) | TCGGAGGGATCTAAGGGCCG (SEQ ID NO: 66) GGTCCATACGGATCATACGG (SEQ ID NO: 67) |
| L243V | ttataaattctctattcagGAACTCGTCAC CGCCTGGTATATTGGCTTTCT TGCGTCATTCTCGCATCGTTTC TTGTTTACTTGGCCGAAAAGG GTGAAA (SEQ ID NO: 68) | CAAGAATCCGATGTACCAGG (SEQ ID NO: 69) AGTAAACAAGAAACGATGCC (SEQ ID NO: 70) |
| T274M | GGGTGAAAACGATCACTTTGA CACATATGCCGATGCCCTTTG GTGGGGACTTATCATGCTCAC TACTATCGGATACGGAGATAA GTACCCACAAACATGGAATGG TAGACTTCTTGCTGCCACCTTC AC (SEQ ID NO: 71) | AGTCTACCATTCCATGTCTG (SEQ ID NO: 72) CAAGCCCCACCACAACGCAT (SEQ ID NO: 73) |

TABLE 8-continued hKCNQ2 variant construction details

| variant | Donor homology ODN | sgRNA |
|---|---|---|
| G290S | cTTACGACAATTGGATATGGT GACAAGTATCCGCAGACTTGG AACTCCCGTCTCTTGGCCGCG ACATTCACCCTGATCGGTGTC AGTTTCTTCGCCCTCCCA (SEQ ID NO: 74) | AGTCTACCATTCCATGTCTG (SEQ ID NO: 75) GACACCGATCAGGGTGAAGG (SEQ ID NO: 76) |
| A294V | cTTACGACAATTGGATATGGT GACAAGTATCCGCAGACTTGG AACGGCCGTCTCTTGGTCGCG ACATTCACCCTGATCGGTGTC AGTTTCTTCGCCCTCCCA (SEQ ID NO: 77) | AGTCTACCATTCCATGTCTG (SEQ ID NO: 78) GACACCGATCAGGGTGAAGG (SEQ ID NO: 79) |
| L351V | ACGTAACCCTGCCGCTGGTTT GATTCAATCCGCTTGGCGTTTT TATGCCACCAATGTCTCCCGC ACTGACCTGCACTCTACCTGG CAATACTACGAAAGAACGGTA (SEQ ID NO: 80) | CGTAGCGTAGAATCTCCAAG (SEQ ID NO: 81) TTGCCAGGTAGAGTGCAGAT (SEQ ID NO: 82) |
| N780T | TGAGACAAGAAGACACCCCA GGATGCAGACCGCCAGAAGG AACTCTCCGTGACTCTGACAC GTCCATTTCAATCCCTTCAGTT G (SEQ ID NO: 83) | TCACGAAGGTTACCCTCTGG (SEQ ID NO: 84) TGGACGTGTCAGAGTCACGA (SEQ ID NO: 85) |

Figure 9A:
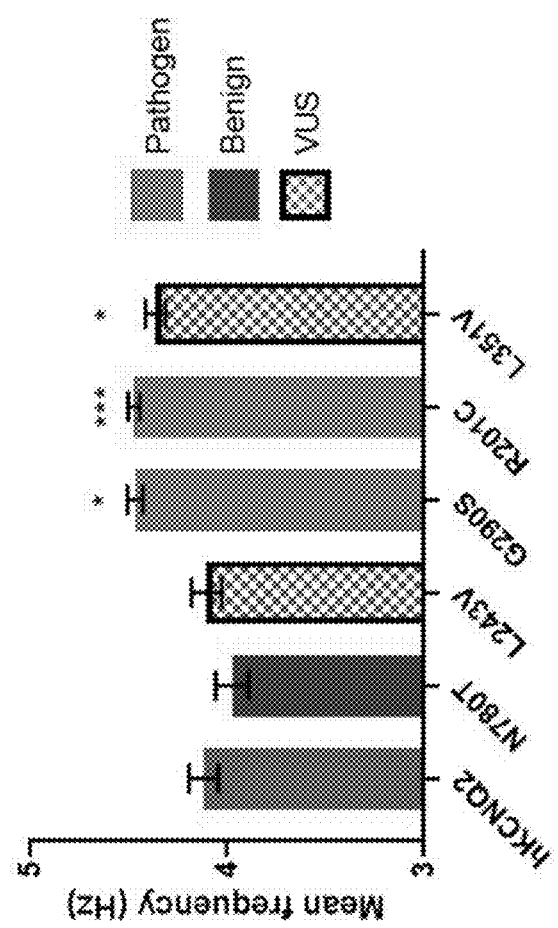
FIG. 9A shows the phenotypic behavior assay (ScreenChip) used to obverse behavior phenotype profile for five clinical variants (R201C, G290S, L351V, N780T, and L243V) installed in the hKCNQ2 wherein three (R201C, G290S, L351V) showed loss of function behavior relative to transgenic control nematode (hKCNQ2) as evidenced by a higher pumping frequency. The benign variant N780T and the L243V variant were no different in pumping frequency from the transgenic control nematode.
Figure 9B:
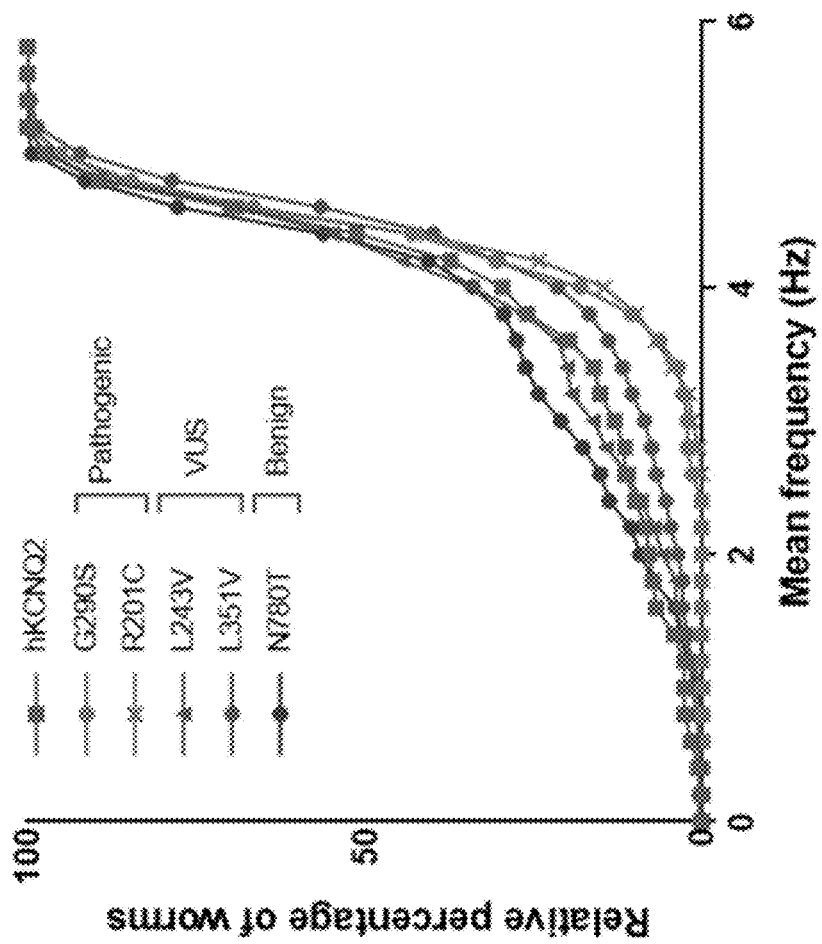
FIG. 9B shows a cumulative distribution of pumping frequency plot data were binned into 0.4 Hz bins and plotted according to the percentage of worms in the dataset that pumped at or below a certain pumping frequency (as indicated on the x-axis).
Figure 10:
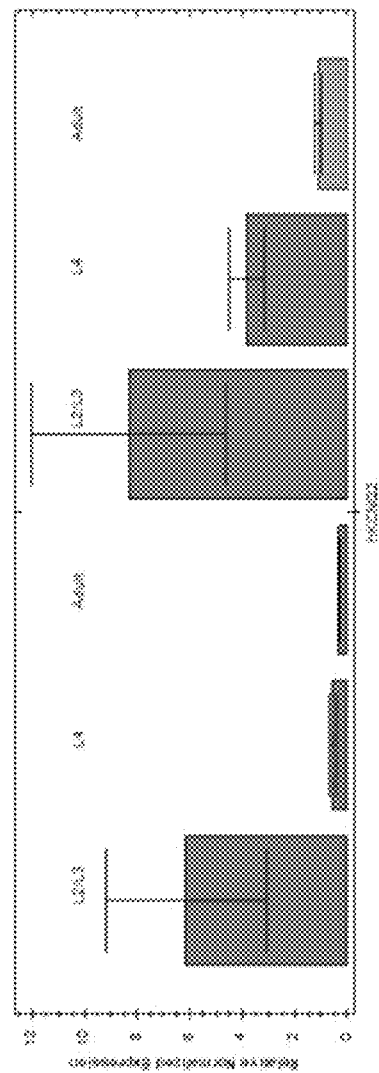
FIG. 10 shows RNA was harvested from nematodes at stages L2/L3, L4, and first day adult. cDNA was prepared using iScript Reverse Transcription Supermix for RT-qPCR and expression was measured by QPCR with SsoAdvanced Universal SYBR Green Supermix. KCNQ2 expression was normalized to two *C. elegans* genes

Phenotypic detection of the presence of deviant behaviors was performed with the ScreenChip and NemaSize assays. The R201C, G290S, and L351V variants showed loss of function behavior relative to wt rescue construct as evidenced by a higher pumping frequency. The benign variant N780T and the L243V variant were no different in pumping frequency from the wt rescue line. See FIG. 9A. Additional variants R198Q and A294V were also tested and showed a higher pumping frequency indicating pathogenicity. Only the R201C variant had a significantly lower volume and smaller area relative to wt rescue construct. No difference in size was observed for the L243V, G290S, L351V, and N780T variants.

Example 11: Generation of Multiple Human KCNQ2 Clinical Variants in a Transgenic Nematode To create multiple variants from one set of microinjections, a multiplex method of CRISPR/Cas9 gene editing was developed. The humanized hKCNQ2 worms (NMX21) were injected with a mix as detailed in Table 9.

TABLE 9

Injection mix.

| | Names | Volume (ul) |
|---|---|---|
| Cas9 5 ug/ul | | 1 |
| sgRNA 1 | WYN0062 | 1.65 |
| sgRNA 2 | WYN0063 | 1.65 |
| dpy-10 sgRNA | | 0.7 |
| ODN (500 ng total) - 1.11 ul of each ODN pooled | CEH9284 CEH9285 CEH9286 CEH9287 CEH9288 CEH9289 CEH9196 CEH9197 NMX0243 | 1 |
| co-CRISPR dpy-10 ODN (500 ng) | CEH2536 | 1 |
| water for a final volume of 10 ul | | 3 |

The injection mix was designed to create 9 distinct mutations as outlined in Table 10.

TABLE 10

Reagent sequences used in this example.

| Name | Purpose | Sequence |
|---|---|---|
| WYN0062 | sgRNA | AGTCTACCATTCCATGTCTG (SEQ ID NO: 86) |
| WYN0063 | sgRNA | GACACCGATCAGGGTGAAGG (SEQ ID NO: 87) |
| CEH9284 | ODN for A294G | TTACGACAATTGGATATGGTGACAAGTATCCGCA GACGTGGAACGGAAGGTTGTTGGGAGCTACGTTC ACCCTGATCGGTGTCAGTTTCTTCGCCCTCCCA (SEQ ID NO: 88) |

TABLE 10-continued

Reagent sequences used in this example.

| Name | Purpose | Sequence |
|---|---|---|
| CEH9285 | ODN for R291S | TTACGACAATTGGATATGGTGACAAGTATCCGCA GACGTGGAACGGATCATTGTTGGCAGCGACGTTC ACCCTGATCGGTGTCAGTTTCTTCGCCCTCCCA (SEQ ID NO: 89) |
| CEH9286 | ODN for G290V | TTACGACAATTGGATATGGTGACAAGTATCCGCA GACGTGGAACGTGCGTTTGTTGGCAGCGACGTTC ACCCTGATCGGTGTCAGTTTCTTCGCCCTCCCA (SEQ ID NO: 90) |
| CEH9287 | ODN for G290D | TTACGACAATTGGATATGGTGACAAGTATCCGCA GACGTGGAACGACCGTTTGTTGGCAGCGACGTTC ACCCTGATCGGTGTCAGTTTCTTCGCCCTCCCA (SEQ ID NO: 91) |
| CEH9288 | ODN for T287N | TTACGACAATTGGATATGGTGACAAGTATCCGCA GAACTGGAACGGACGTTTGTTGGCAGCGACGTTC ACCCTGATCGGTGTCAGTTTCTTCGCCCTCCCA (SEQ ID NO: 92) |
| CEH9289 | ODN for T287I | TTACGACAATTGGATATGGTGACAAGTATCCGCA GATCTGGAACGGACGTTTGTTGGCAGCGACGTTC ACCCTGATCGGTGTCAGTTTCTTCGCCCTCCCA (SEQ ID NO: 93) |
| CEH9196 | ODN for G290S | cTTACGACAATTGGATATGGTGACAAGTATCCGCA GACTTGGAACTCCCGTCTCTTGGCCGCGACATTCA CCCTGATCGGTGTCAGTTTCTTCGCCCTCCCA (SEQ ID NO: 94) |
| CEH9197 | ODN for A294V | cTTACGACAATTGGATATGGTGACAAGTATCCGCA GACTTGGAACGGCCGTCTCTTGGTCGCGACATTC ACCCTGATCGGTGTCAGTTTCTTCGCCCTCCCA (SEQ ID NO: 95) |
| NMX0243 | ODN for L292P | TTACGACAATTGGATATGGTGACAAGTATCCGCA GACTTGGAACGGCCGTCCATTGGCCGCGACATTC ACCCTGATCGGTGTCAGTTTCTTCGCCCTCCCA (SEQ ID NO: 96) |

Sixty-three (63) animals were injected with a mix and incubated at 25° C. F1 animals were observed for the dpy-10 heterozygous rolling phenotype 4 days after injection. 15 Jackpot plates (over 10 rollers) were observed. 272 F1 animals with the rolling co-CRISPR phenotype were isolated from 15 Jackpot plates. After laying progeny, F1 animals were harvested and DNA was isolated using the NemaMetrix Worm Lysis kit. PCR using the primers NMX0244/0246 to amplify 770 bp around the region to be edited. Restriction enzyme (RE) digest was performed with AccI at 37° C. for 1 hour, followed by an inactivation step of 80° C. for 20 min, and visualized by gel electrophoresis. The AccI site will be present only in the wild-type animals and not in the accurately edited animals. Results of the RE digest are described in Table 11.

TABLE 11

Restriction enzyme digest results.

| | Number of F1s (% of F1s) |
|---|---|
| Homozygous wt (no uncut band present) | 61 (24.3%) |
| Heterozygous (cut and uncut band present) | 116 (42.6%) |
| Homozygous mut (no cut band present) | 76 (27.9%) |

Restriction enzyme digested PCR samples were purified by Omega MagBind cleanup beads. Sanger sequencing was performed by Sequetech. Results of the sequencing are described in Table 12.

TABLE 12

Sequencing results.

| Variant | Number observed (% edit frequency) | Number of homozygous F1s found |
|---|---|---|
| T287I | 25 (15.5%) | 3 |
| T287N | 18 (11.2%) | 6 |
| G290D | 23 (14.3%) | 7 |
| G290S | 16 (9.9%) | 3 |
| G290V | 14 (8.7%) | 4 |
| R291S | 24 (14.9%) | 8 |
| L292P | 14 (8.7%) | 7 |
| A294G | 8 (5%) | 1 |
| A294V | 19 (11.8%) | 9 |
| WT | 61 | |
| Other | 49 | |

From the F1s, 23% were wild-type (un-edited), 18% were an incorrect edit, and 59% contained a correct edit.

Example 12: Using the 3'UTR to Modify Expression in Humanized Animal Models

The untranslated region on the 3' end of the of mRNA product (3'UTR) is known to have complex regulatory roles in native and transgenic systems across many organisms, including humans and *C. elegans*. This regulatory role was used to provide more exquisite control of gene expression and create a system of "tunable" expression using gene editing to insert one of a library of 3'UTRs with known effects on expression.

For purposes of efficiently selecting successful edits, heterologous gene constructs were made with a short 3'UTR from a highly expressed C. elegans gene (eft-3), followed by a hygromycin (HygR) resistance gene, with the native 3'UTR displaced further down the DNA strand. Once the lines were established as homozygotes, CRISPR techniques were used to remove the short-inserted UTR and the HygR cassette and restored the native UTR of the C. elegans heterolog to the humanized transcript. The sgRNA and ODN sequences are listed in Table 13.

TABLE 13

Reagents for 3'UTR restoration in hSTXBP1 and KCNQ2.

| Name | Purpose | Sequence |
|---|---|---|
| SG00266 | sgRNA-hSTXBP1 | (SEQ ID NO: 10) |
| SG00267 | sgRNA-hSTXBP1 | ACTAGACATATGACAGAGTG (SEQ ID NO: 97) |
| CEH7275 | ODN-hSTXBP1 | (upper case hSTXBP1, lower case native unc-18 3'UTR) (SEQ ID NO: 13) |
| WYN0049 | sgRNA-hKCNQ2 | CAACAATGAAGATGGACTGG (SEQ ID NO: 98) |
| WYN0050 | sgRNA-hKCNQ2 | GATTCTACTCCATTGAACAA (SEQ ID NO: 99) |
| CEH7275 | ODN-hKCNQ2 | AAAATAAGCGGCCGCCCCTCCCCAGAAGTC CTCCAACAATGGTCCCGGTACTTCAAGTTGT TAAaacatat (upper case hKCNQ2, upper case bold non-coding residual sequence, lower case kqt-1 native 3'UTR) (SEQ ID NO: 100) |

The humanized STXBP1 animals, the eft-3, and the HygR cassette were uncoordinated with severe motor impairment. Once the native (unc-18) 3'UTR was restored to its normal position relative to the gene, the lines with the hSTXBP1 transgene rescued the unc-18 knockout phenotype and motor function was restored. In the case of hKCNQ2, restoration of the native 3'UTR of the C. elegans heterolog increased the expression of the transgene throughout the worm lifespan. See FIG. 11. The sgRNA and ODN sequences used to create the 3'UTR restoration by CRISPR/Cas9 are listed in Table 13.

Changing the 3'UTR from eft-3 to the native 3'UTR for both STXBP1 and KCNQ2 increased function and or expression. To expand the capacity to use different 3' UTRs to turn expression, a library of 3'UTRs is made from literature searches, online databases, and experimental evidence. CRISPR/Cas9 editing techniques are used to insert different 3' UTRs immediately after the transgene stop codon. Different lines are compared for capacity to rescue gene function. 3' UTRs giving optimal rescue of gene function are used as backgrounds for installation of clinical variants. Variants can be installed into an under rescued line for gain-of-function assessment or installed into an over rescued line for loss-of-function assessment.

Example 13: Maintaining Heterozygotes

Some diseases have a high proportion of autosomal dominance for contribution to diseases. The result is only one copy of a variant is sufficient to manifest phenotypic deviant behavior. The most accurate model of disease is to maintain a heterozygous either at the natural locus or as two genes with one gene at a new "synthetic" locus. There are two ways to maintain heterozygosity.

First method to maintain heterozygosity is to create two different copies on each chromosome wherein one copy is wild type configuration and the second sister chromosome has a variant content configuration. Each copy is maintained trans-generationally by use of two different markers (fluorescent, antibiotic resistant, etc.). One method to create the heterozygous animal is to make two separate lines (variant in one line and wildtype in other line). Genetic crosses are performed to bring both alleles into same animal (the heterozygote). The heterozygote is maintained by exposure conditions that select for both markers (dual fluorescent/dual antibiotic resistance). This is a natural locus heterozygote which will be necessary to utilize for conditions where pure haploinsufficiency is the main driver to variant phenotypic output.

The second method for maintaining heterozygosity uses a second synthetic safe-harbor locus which does not need selection markers for its maintenance. Instead, the synthetic locus is used for either the heterologous wild type gene or clinical variant thereof. For instance, a transgene of the target gene containing all the appropriate material for expression is brought into a synthetic locus. The original homolog locus is typically modified to contain the same coding content as the synthetic locus except for the variant change in question. The resulting animal has equal expression of heterologous clinical variant and wild type control. This use of a synthetic locus to create heterozygote locus is useful for exploring dominant negative effects but is less likely to be useful for variant behavior that is solely dependent on haploinsufficiency.

Example 15: Assessing the Function of the Heterologous Genes and Clinical Variants in Gene Edited Transgenic Zebrafish For genes of low homology between zebrafish and human, the most favorable approach for accurate capture of variant biology requires introduction of human gene either in trans or at a native locus. The coding sequence for the human gene is optimized for expression in Zebrafish by methods detailed in Example 1: optimization of codons, introduction of zebrafish intron coding sequences (e.g., from highly expressed zebrafish gene), and optimization of splicing (e.g., removal of aberrant splice sites introduced by creation of the chimeric heterologous gene). Native locus insertion of the chimeric heterologous gene can be performed with current methods (e.g., CRISPR) to insert an entire chimeric human transgene at the start codon of an ortholog site. Alternatively, a chimeric human transgene is inserted randomly (e.g., Tol2 mediated gene insertion) or at an established safe harbor site. Once a transgene is inserted the original sequence can be disrupted, if necessary, by a second round of targeted gene segment deletions via CRISPR or similar methods.

In one example, the insertion of human transgene content is done in trans by, first, insertion of an appropriate promoter, a good Cas9 sgRNA site, and part of a fluorescent marker. Next, a second transgenesis is done to insert a human coding sequence and the remainder of the fluorescent marker in a configuration that restores fluorescence. In another embodiment, the promoter, a transposon site (e.g., phiC) and part of a fluorescent marker is used in a first transgenesis procedure, which is followed by a second transgenesis procedure that restores full-length functional fluorophore.

In a second example, the insertion of human transgene content is done in cis by inserting all or part of human sequence at the animals native ortholog locus using CRISPR-techniques, or similar methods.

Example 16: Assessing the Function of the Heterologous Genes and Clinical Variants in Transient Transgenic Zebrafish If insertion of human transgene or segment thereof is not practical, RNA-based transgene expression can be used to assess variant function.

In one example, a gene knock out of a target ortholog is obtained from either genetic stock centers or is made with gene knock-out techniques (e.g., CRISPR-based gene deletion). Next, a humanizing transgene mRNA coding for the human ortholog sequence is obtained and used to rescue function. In another example, a morpholino RNAi is used to knock down expression of a target ortholog gene and a humanizing mRNA is introduced to rescue gene function. Once rescue of function is achieved, genetic variants are inserted into the humanizing RNA sequence and defects of rescue capacity are measured and quantified.

By way of example to demonstrate the general principle a knockout line for the Zebrafish stxbp1a gene is created by CRISPR/Cas9. sgRNAs targeting early in the coding sequence, exon 3, were used to create cuts in the sequence coding for amino acids 38 and 45 (sgRNA sequences: TAGTGGACCAGCTCAGCATG (SEQ ID NO: 101) and GATATCAGTCATTTTGCAGC (SEQ ID NO: 102)). Zebrafish lines with germline transmitting mutations that lead to an early stop are selected. Embryos are injected with human mRNA for STXBP1 or Zebrafish mRNA for Stxbp1a and rescue of movement and lethality is measured and compared with mCherry mRNA injected controls. Variant mutations are introduced into the plasmid with the STXBP1 mRNA expression construct. mRNA with the variants are produced and injected into the knockout zebrafish lines. Movement and lethality phenotypes are measured and compared to the wildtype human mRNA control. This is a rapid method for variant assessment using a vertebrate system.

We claim:

1. A transgenic nematode system for assessing function of a chimeric heterologous gene, comprising:
   a host nematode comprising a chimeric heterologous gene comprising heterologous exon coding sequences interspersed with artificial host nematode intron sequences optimized for expression in the host nematode, wherein:
   the heterologous exon coding sequences are from a eukaryotic gene,
   the chimeric heterologous gene replaces an entire host nematode gene ortholog at a native locus,
   wherein the artificial host nematode intron sequences improve mRNA stability of expression of the chimeric heterologous gene; and
   the expression of the chimeric heterologous gene at least partially restores function of the replaced nematode ortholog providing a validated transgenic nematode.

2. The system of claim 1, wherein the eukaryotic gene is a human gene.

3. The system of claim 1, wherein the chimeric heterologous gene is codon optimized for the nematode and does not contain aberrant splice donor and/or acceptor sites.

4. The system of claim 1, wherein the host nematode is *C. elegans*.

5. The system of claim 1, wherein the heterologous exon coding sequences are wildtype sequences.

6. The system of claim 1, wherein the heterologous exon coding sequences comprise one or more mutations resulting in at least one amino acid change.

7. A method of preparing a transgenic nematode system of claim 1, comprising:
   a) optimizing a heterologous gene coding sequence for expression in a host nematode comprising selecting host optimized codons, adding artificial host nematode intron sequences between exon coding sequences of the heterologous gene, and removing aberrant splice donor and/or acceptor sites to provide a chimeric heterologous gene sequence; and,
   b) inserting the chimeric heterologous gene sequence via homologous recombination into a native locus of the host nematode wherein the chimeric heterologous gene replaces an entire nematode ortholog gene at the native locus, and wherein expression of the chimeric heterologous gene at least partially restores function of the replaced nematode ortholog, wherein the heterologous exon coding sequences are from a eukaryotic gene.

8. The method of claim 7, further comprising introducing one or more mutations in the heterologous exon coding sequences resulting in at least one amino acid change.

9. The method of claim 8, wherein the mutation corresponds to a human disease gene clinical variant.

10. The method of claim 8, wherein the mutations are created from a pool of DNA repair templates each containing one or more mutations.

11. A transgenic nematode system for assessing function of a chimeric heterologous gene according to claim 1, comprising:
   a host nematode comprising a chimeric heterologous gene comprising heterologous exon coding sequences interspersed with artificial host nematode intron sequences optimized for expression in the host nematode wherein the chimeric heterologous gene replaces an entire host nematode gene ortholog at a native locus and expression of the chimeric heterologous gene at least partially restores function of the replaced nematode ortholog providing a validated transgenic nematode, wherein the heterologous exon coding sequences are selected from a single human gene selected from the group consisting of:

AARS, ABCA4, ABCB4, GABRB3, SIX3, PRKAG2, NLGN4X, WASHC5, ABCA3, ABCB11, ABCC2, GABRG2, SLC12A3, PRKG1, NOTCH1, WRN, ABCC6, ARFGEF2, BRD2, GARS, SLC12A6, PSEN1, NOTCH2, WWOX, ABCD1, ASAH1, BRIP1, GATA3, SLC17A5, PSMA1, NOTCH3, ZIC2, ACADM, ATL1, CACNA1A, GATA4, SLC19A3, PSMC2, NPC1, ZMYND11, ACTA1, ATP13A2, CACNA1C, GBA, SLC22A5, PSMC4, NPEPPS, CUL3, ACTA2, ATP1A2, CACNA1D, GBA2, SLC25A13, PSMC5, NPHS2, NAA15, ACTB, ATP1A3, CACNA1F, KIF1B, SLC25A22, PSM D2, NR2E3, KMT5B, ACTG1, ATP6V0A2, CACNA1H, KIF5A, SLC26A2, PSM D3, NRAS, TBR1, ACTN2, ATRX, CACNA1S, KMT2D, SLC26A4, PTCH1, NSDHL, PTEN, ADA, AVPR2, CACNB2, KRAS, TMEM67, SLC2A1, OTOF, CHD8, ADAR, BBS7, CACNB4, L1CAM, TNNI3, SLC2A2, PTCHD1, MYT1L, ADSL, BCKDHA, CAPN3, *LAMA*1, TNNT2, SLC35C1, PTPN11, ARID1B, AGPAT2, BEST1, CASK, *LAMA*2, TPO, SLC37A4, RAB7A, ASH1L, ALDH7A1, BICD2, CAV3, LIPA, TRPM1, SLC3A1, RAD50, TRIP12, ALDOB, BLM, CBS, LMNA, TRPM4, SLC4A1, RARS2, DYRK1A, ANK1, BMPR1A, CDKN1B, LRP2, GRIN1, SLC9A6, RBFOX1, SYNGAP1, ANK2, BRCA1, CDKN1C, MAN2B1, GRN, SMAD3, REEP1, GRIN2B, ANK3, BRD1, CFTR, MAP2K1, HADH, SMAD4, RP1, ANK2, CHAT, COL4A5, DYNC2H1, MAP2K2, HNF4A, SMARCA2, RP1L1, SCN2A, CHD8, CREBBP, DYRK1A, MCCC1, HPS5, SMARCA4, RP2, DSCAM, CHEK2, CRX, DYSF, MCCC2, HSD1764, SMC1A, RPE65, SHANK3, CHRNA2, CRYAB, EGR2, MEGF10, HSPB1, SMPD1, RPGRIP1, POGZ, CHRNA4, CSRP3, EHMT1, PAH, MET, SPAST, RPS6KA3, SETD5, CHRNA7, CTNNB1, EMC2, PANK2, MFSD8, SPEN, RRM2B, KATNAL2, CHRNB2, CTSD, EMC3, PAX2, MGAT1, SPG7, SCNN1B, KMT2A, CHRND, CUBN, EMC6, PAX3, MPI, TTN, SDHA, ADNP, CHRNE, CYP27A1, ENPP1, PAX6, MTOR, TTR, SPTA1, ASXL3, CHRNG, CYP4V2, EP300, PCCA, MYH11, TUBA1A, SPTAN1, RELN, CLCN1, DDX3X, ERCC2, PEX6, MYH14, TUBB4A, SPTLC2, PSEN1, CLCNKB, DIAPH1, ERCC6, PFKM, MYH3, TYR, STAT3, APP, CLN3, DMD, ETHE1, PHEX, MYH6, VPS11, STXBP1, PSEN2, CNGA3, DNM2, FGFR1, PHF8, MYH7, VPS39, SYNE1, SORL1, CNTN4, DOCKS, FGFR2, PHKA1, MYH7, KCNQ1, TBC1D24, MAPT, CNTNAP2, DPYD, FGFR3, PIK3R1, MYH9, KCNQ2, TBX5, IL1 B, COL4A1, DYNC1H1, FKBP10, PKD2, MYL2, KCNQ3, TCF4, BACE1, FKTN, GCDH, IFIH1, PLA2G6, MYL3, KCNV2, TCIRG1, ACE, FLNA, GCK, IGHMBP2, PLEC, MYLK2, KDM6A, TECTA, TARDBP, FLNB, GLB1, ITGA2B, PLP1, MYO15A, KIF11, TGFB2, UNC13A, FLNC, GLI2, JUP, SERPINA1, PNPLA6, KIF1A, TGFBR1, LRRK2, FOXG1, GLRA1, KANK1, SETD1B, POGZ, MYO1A, TH, SNCA, FOXP1, GOLGA7, KCNJ11, SETD5, POLG, MYO6, TMC1, PARK2, FOXP2, GOSR2, KCNJ2, SGCA, POU3F4, NALCN, TMEM216, PINK1, GAA, GPD1L, KCNJ5, SGCG, PQBP1, NF2, VRK1, MAPT, GABRA1, GRIA3, KCNMA1, SHH, PRICKLE1, NKX2-5, WAS, GBA, PARK7, DRD1, IGF1R, MAOB, WRN, SOD1, SQSTM1, CHMP2B, C90RF72, PON1, FUS, ANG, VCP, ATXN2, SMN1, ZMPSTE24, RECQL4, TP53, MAGI2, DISC1, DTNBP1, COMT, HTR2A, N RG1, ATP2A2, SM N2, DYNC1H1, TRPV4, BICD2, IGHMBP2, VRK1, UBA1, ASAH1, VAPB, LM NA, ELK1, ATP1A3, PTEN, ERCC6, APP, SLC6A3, CACNA1A, and, KL.

12. A transgenic nematode system for assessing function of a chimeric heterologous gene according to claim 1, comprising:
a host nematode comprising a chimeric heterologous gene comprising heterologous exon coding sequences interspersed with artificial host nematode intron sequences optimized for expression in the host nematode wherein the chimeric heterologous gene replaced an entire host nematode gene ortholog at a native locus and expression of the heterologous gene at least partially restores function of the replaced nematode ortholog providing a validated transgenic nematode, wherein the chimeric heterologous gene sequence is selected from SEQ ID NO: 1, SEQ ID NO: 45, or SEQ ID NO: 61.

\* \* \* \* \*